US011564914B2

(12) United States Patent
Trindade Da Silva et al.

(10) Patent No.: US 11,564,914 B2
(45) Date of Patent: Jan. 31, 2023

(54) METHODS OF TREATING BONE LOSS

(71) Applicants: THE REGENTS OF THE UNIVERSITY OF CALIFORNIA, Oakland, CA (US); Carlos Antonio Trindade Da Silva, Uberlandia (BR)

(72) Inventors: Carlos Antonio Trindade Da Silva, Uberlandia (BR); Buce D. Hammock, Davis, CA (US); Fawaz G. Haj, Davis, CA (US); Ahmed Bettaieb, Knoxville, TN (US); Ahmet Bora Inceoglu, Davis, CA (US)

(73) Assignees: THE REGENTS OF THE UNIVERSITY OF CALIFORNIA, Oakland, CA (US); Carlos Antonio Tindade Da Silva, Uberlandia (BR)

( * ) Notice: Subject to any disclaimer, the term of this patent is extended or adjusted under 35 U.S.C. 154(b) by 403 days.

(21) Appl. No.: 16/308,672

(22) PCT Filed: Jun. 8, 2017

(86) PCT No.: PCT/US2017/036552
§ 371 (c)(1),
(2) Date: Dec. 10, 2018

(87) PCT Pub. No.: WO2017/214394
PCT Pub. Date: Dec. 14, 2017

(65) Prior Publication Data
US 2020/0306232 A1 Oct. 1, 2020

Related U.S. Application Data

(60) Provisional application No. 62/348,144, filed on Jun. 10, 2016.

(51) Int. Cl.
A61K 31/4468 (2006.01)
A61P 19/08 (2006.01)
A61K 9/00 (2006.01)
C12N 15/113 (2010.01)

(52) U.S. Cl.
CPC ........ A61K 31/4468 (2013.01); A61K 9/0014 (2013.01); A61K 9/0053 (2013.01); A61K 9/0056 (2013.01); A61P 19/08 (2018.01); C12N 15/1137 (2013.01); C12N 2310/14 (2013.01)

(58) Field of Classification Search
CPC .............. A61K 31/4468; A61K 9/0014; A61K 9/0053; A61K 9/0056; A61P 19/08; C12N 15/1137; C12N 2310/14
See application file for complete search history.

(56) References Cited

U.S. PATENT DOCUMENTS

2006/0073213 A1* 4/2006 Hotamisligil .......... A61K 31/13
424/600
2011/0269831 A1 11/2011 Hammock et al.
2012/0315283 A1* 12/2012 Panigraphy ............. A61P 25/00
424/158.1

OTHER PUBLICATIONS

Guan et al., "Epoxyeicosanoids suppress osteoclastogenesis and prevent ovariectomy-induced bone loss", The FASEB Journal, Mar. 2015, pp. 1092-1101 vol. 29, No. 3.
International Search Report for PCT/US2017/036552 dated Dec. 15, 2017, 5 pages.
Kawai et al., "B and T lymphocytes are the primary sources of RANKL in the bone resorptive lesion of periodontal disease", American Journal of Pathology, Sep. 2006, pp. 987-998, vol. 169, No. 3.
Papadopouli et al., "Role of OPG/RNKL/RANK axis on the vasculature", Apr. 2008, pp. 497-506, vol. 23, No. 4.
Written Opinion of the International Searching Authority for PCT/US2017/036552 dated Dec. 15, 2017, 7 pages.
Bartold et al., Periodontitis: a host-mediated disruption of microbial homeostasis. Unlearning learned concepts, Periodontology 2000, Jun. 2013, vol. 62, No. 1, pp. 1-20.
Bettaieb et al., Soluble Epoxide Hydrolase Pharmacological Inhibition Ameliorates Experimental Acute Pancreatitis in Mice, Mol Pharmacol, Aug. 2015, vol. 88, pp. 281-290.
Bettaieb et al., Soluble Epoxide Hydrolase Deficiency or Inhibition Attenuates Diet-induced Endoplasmic Reticulum Stress in Liver and Adipose Tissue, The Journal of Biological Chemistry, May 17, 2013, vol. 288, No. 20, pp. 14189-14199.
Cao et al., Endoplasmic Reticulum Stress Interacts With Inflammation in Human Diseases, Journal of Cellular Physiology, 2016, vol. 231, pp. 288-294.
Capdevila et al., Liver microsomal cytochrome P-450 and the oxidative metabolism of arachidonic acid, Proc. Natl. Acad. Sci. USA, Sep. 1981, vol. 78, No. 9, pp. 5362-5366.
Chacos et al., The Reaction of Arachidonic Acid Epoxides (Epoxyeicosatrienoic Acids) with a Cytosolic Epoxide Hydrolase, Archives of Biochemistry and Biophysics, Jun. 1983, vol. 223, pp. 639-648.
Chiamvimonvat et al., The Soluble Epoxide Hydrolase as a Pharmaceutical Target for Hypertension, J Cardiovasc Pharmacol™, Sep. 2007. vol. 50, No. 3, pp. 225-237.
Domon et al., Up-regulation of the endoplasmic reticulum stress-response in periodontal disease, Clinica Chimica Acta, 2009, vol. 401, pp. 134-140.
Eke et al., Prevalence of Periodontitis in Adults in the United States: 2009 and 2010, J Dent Res, 2012, vol. 91, No. 10, pp. 914-920.
Flemmig, Periodontitis, Ann Periodontol, Dec. 1999, vol. 4, pp. 32-38.

(Continued)

Primary Examiner — Genevieve S Alley
(74) Attorney, Agent, or Firm — Mintz, Levin, Cohn, Ferris, Glovsky & Popeo, P.C.

(57) ABSTRACT

Provided are compositions and methods for preventing, mitigating, decreasing, inhibiting and/or reversing bone loss and/or increasing and/or promoting bone regeneration and remodeling and/or preventing, mitigating, decreasing, inhibiting and/or reversing periodontitis and/or periodontal disease in a subject by administering to the subject an effective amount of an inhibitor of soluble epoxide hydrolase (sEH).

23 Claims, 8 Drawing Sheets

Specification includes a Sequence Listing.

(56) References Cited

OTHER PUBLICATIONS

Haeggstrom et al., Advances in eicosanoid research, novel therapeutic implications, Biochemical and Biophysical Research Communications, 2010, vol. 396, pp. 135-139.
Hajishengallis et al., The Keystone-Pathogen Hypothesis, Nat Rev Microbiol, Oct. 2012, vol. 10, No. 10, pp. 717-725.
Harris et al., Inhibition of soluble epoxide hydrolase attenuates hepatic fibrosis and endoplasmic reticulum stress induced by carbon tetrachloride in mice, Toxicol Appl Pharmacol, Jul. 15, 2015, vol. 286, No. 2, pp. 102-111.
Hasturk et al., Resolvin E1 Regulates Inflammation at the Cellular and Tissue Level and Restores Tissue Homeostasis In Vivo, The Journal of Immunology, 2007, vol. 179, pp. 7021-7029.
Imig, Epoxides and Soluble Epoxide Hydrolase in Cardiovascular Physiology, Physiol Rev., Jan. 2012, vol. 92, No. 1, pp. 101-130.
Inceoglu et al., Analgesia mediated by soluble epoxide hydrolase inhibitors is dependent on cAMP, Proc Natl Acad Sci USA, Mar. 22, 2011, vol. 108, No. 12, pp. 5093-5097.
Inceoglu et al., Endoplasmic Reticulum Stress in the Peripheral Nervous System is a Significant Driver of Neuropathic Pain, Proc Natl Acad Sci USA, Jul. 21, 2015, vol. 112, No. 29, pp. 9082-9087.
Kang et al., *Aggregatibacter actinomycetemcomitans* Infection Enhances Apoptosis In Vivo through a Caspase-3-Dependent Mechanism in Experimental Periodontitis, Infection and Immunity, Jun. 2012, vol. 80, No. 6, pp. 2247-2256.
Kung et al., Increased Classical Endoplasmic Reticulum Stress Is Sufficient to Reduce Chondrocyte Proliferation Rate in the Growth Plate and Decrease Bone Growth, PLoS One, Feb. 18, 2015, pp. 1-21, 10:e0117016.
Lacey et al., Osteoprotegerin Ligand is a Cytokine that Regulates Osteoclast Differentiation and Activation, Cell, Apr. 17, 1998, vol. 93, pp. 165-176.
Levy et al., Resolution of Inflammation in Asthma, Clin Chest Med, Sep. 2012, vol. 33, No. 3, pp. 559-570.
Liu et al., Pharmacokinetic optimization of four soluble epoxide hydrolase inhibitors for use in a murine model of inflammation, British Journal of Pharmacology, 2009, vol. 156, pp. 284-296.
Liu et al., Inhibition of soluble epoxide hydrolase enhances the anti-inflammatory effects of aspirin and 5-lipoxygenase activation protein inhibitor in a murine model, Biochem Pharmacol, Mar. 15, 2010, vol. 79, No. 6, pp. 880-887.
Marnett, The COXIB Experience: A Look in the Rearview Mirror, Annual Review of Pharmacology and Toxicology, 2009, vol. 49, pp. 265-290.
Morisseau et al., Potent urea and carbamate inhibitors of soluble epoxide hydrolases, Proc. Natl. Acad. Sci. USA, Aug. 1999, vol. 96, pp. 8849-8854.
Morisseau et al., Impact of Soluble Epoxide Hydrolase and Epoxyeicosanoids on Human Health, Annual Review of Pharmacology and Toxicology, 2013, vol. 53, pp. 37-58.
Morisseau et al., Naturally occurring monoepoxides of eicosapentaenoic acid and docosahexaenoic acid are bioactive antihyperalgesic lipids, J Lipid Res, 2010, vol. 51, pp. 3481-3490.
Napimoga et al., Exogenous Administration of 15d-$PGJ_2$-Loaded Nanocapsules Inhibits Bone Resorption in a Mouse Periodontitis Model, the Journal of Imunology, 2012, vol. 189, pp. 1043-1052.
Napimoga et al., Quercetin Inhibits Inflammatory Bone Resorption in a Mouse Periodontitis Model, Journal of Natural Products, Nov. 18, 2013, vol. 76, pp. 2316-2321.
Node et al., Anti-inflammatory Properties of Cytochrome P450 Epoxygenase-Derived Eicosanoids, Science, Aug. 20, 1999, vol. 285, pp. 1276-1279.
Norwood et al., Epoxyeicosatrienoic acids and soluble epoxide hydrolase: potential therapeutic targets for inflammation and its induced carcinogenesis, Am J Transl Res, 2010, vol. 2, No. 4, pp. 447-457.
Okada et al., Identification and Distribution of Immunocompetent Cells in Inflamed Gingiva of Human Chronic Periodontitis, Infection and Immunity, Jul. 1983, vol. 41, No. 1, pp. 365-374.
Ortega-Gomez et al., Resolution of inflammation: an integrated view, EMBO Molecular Medicine, 2013, vol. 5, pp. 661-674.
Rose et al., 1-Aryl-3-(1-acylpiperidin-4-yl)urea Inhibitors of Human and Murine Soluble Epoxide Hydrolase: Structure-Activity Relationships, Pharmacokinetics, and Reduction of Inflammatory Pain, J Med Chem, Oct. 14, 2010, vol. 53, No. 19, pp. 7067-7075.
Schmelzer et al., Soluble epoxide hydrolase is a therapeutic target for acute inflammation, Proc. Natl. Acad. Sci. USA, 2005, vol. 102, No. 28, pp. 9772-9777.
Schmelzer et al., Enhancement of antinociception by coadministration of nonsteroidal anti-inflammatory drugs and soluble epoxide hydrolase inhibitors. Proc. Natl. Acad. Sci. USA, Sep. 12, 2006, vol. 103, No. 37, pp. 13646-13651.
Serhan et al., Novel Anti-lnflammator—Pro-Resolving Mediators and Their Receptors, Curr Top Med Chem, 2011, vol. 11, No. 6, pp. 629-647.
Spector, Arachidonic acid cytochrome P450 epoxygenase pathway, J Lipid Res, Apr. 2009, 50 Supp (suppl)I:S52-56.
Van Dyke, Proresolving lipid mediators: potential for prevention and treatment of periodontitis, Journal of Clinical Periodontology, 2011, 38 Suppl 11:119-125.
Viswanathan et al., Involvement of CYP 2C9 in Mediating the Proinflammatory Effects of Linoleic Acid in Vascular Endothelial Cells, Journal of the American College Nutrition, 2003, vol. 22, No. 6, pp. 502-510.
Williams et al., 20-HETE: A New Target for the Treatment of Hypertension, J Cardiovasc Pharmacol, Oct. 2010, vol. 56, No. 4, pp. 336-344.
Yamada et al., Endoplasmic reticulum stress response and bone loss in experimental periodontitis in mice, Journal of Periodontal Research, 2015, vol. 50, pp. 500-508.
Ostermann et al., Oral treatment of rodents with soluble epoxide hydrolase inhibitor 1-(1-propanoylpiperidin-4-yl)-3-[4-(trifluoromethoxy)phenyl]urea (TTPU): Resulting drug levels and modulation of oxylipin pattern, Prostaglandins & Other Lipid Mediators, 2015, vol. 121, pp. 131-137.

\* cited by examiner

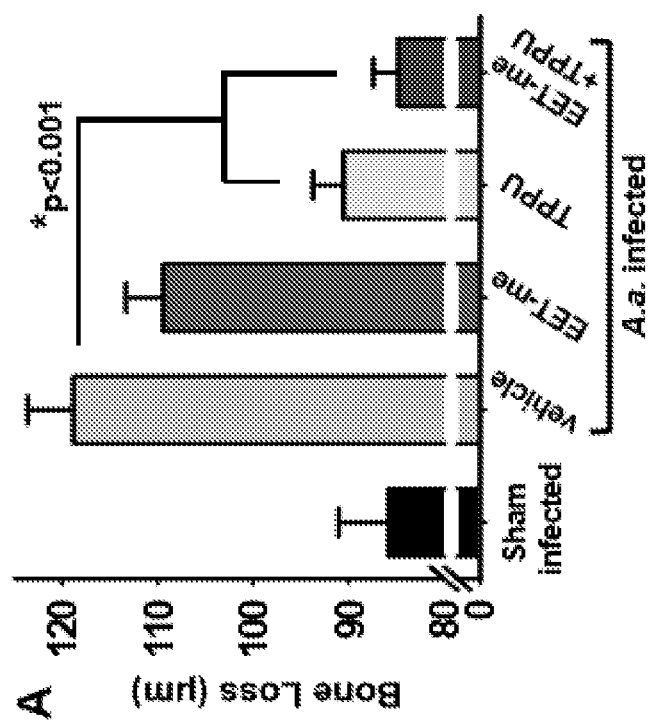
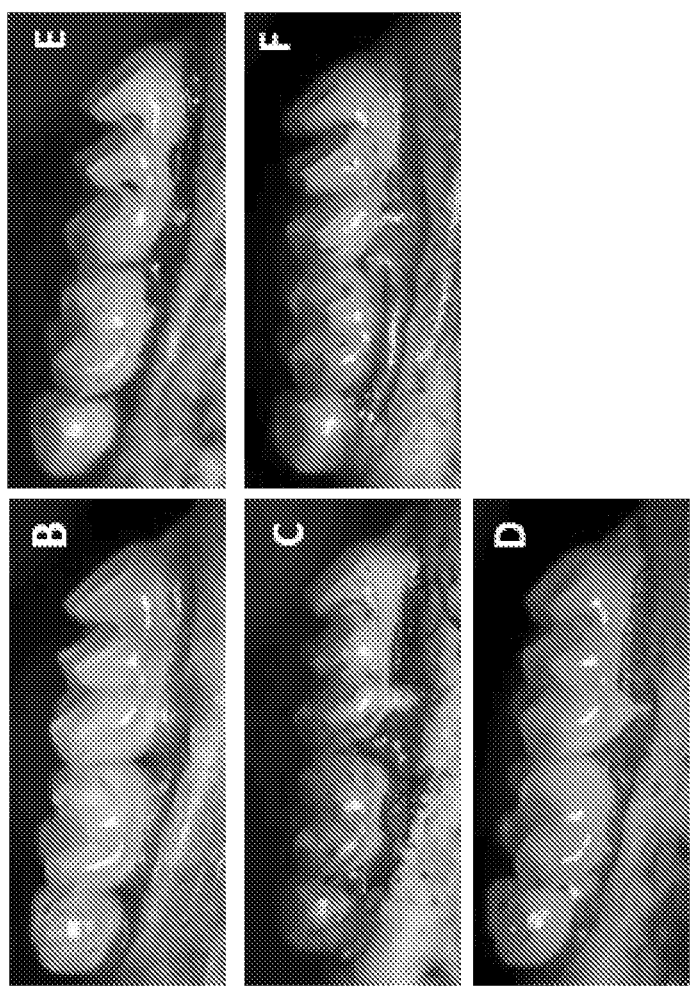
Fig. 2A-F

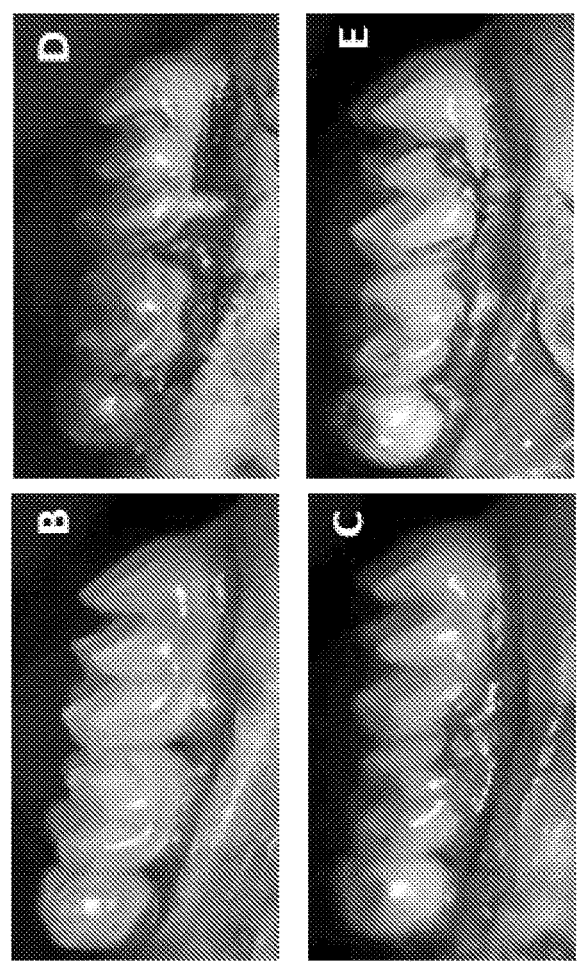
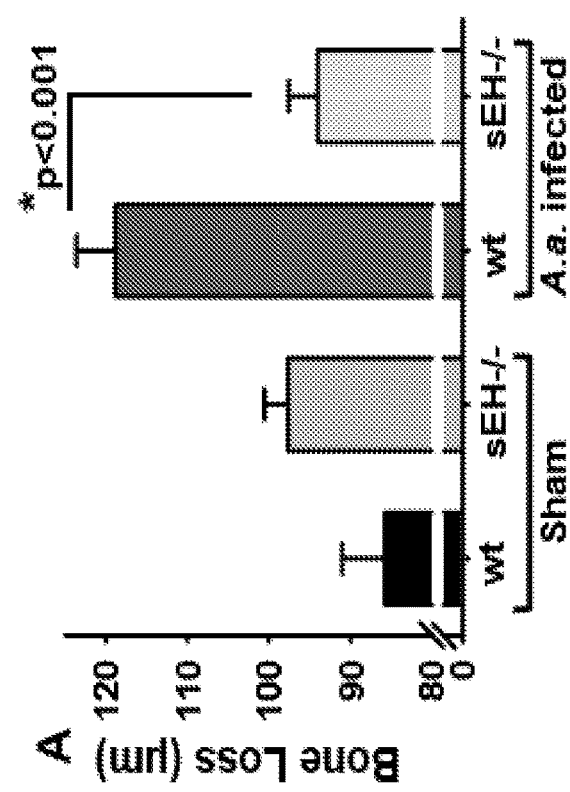
Fig. 4A-E

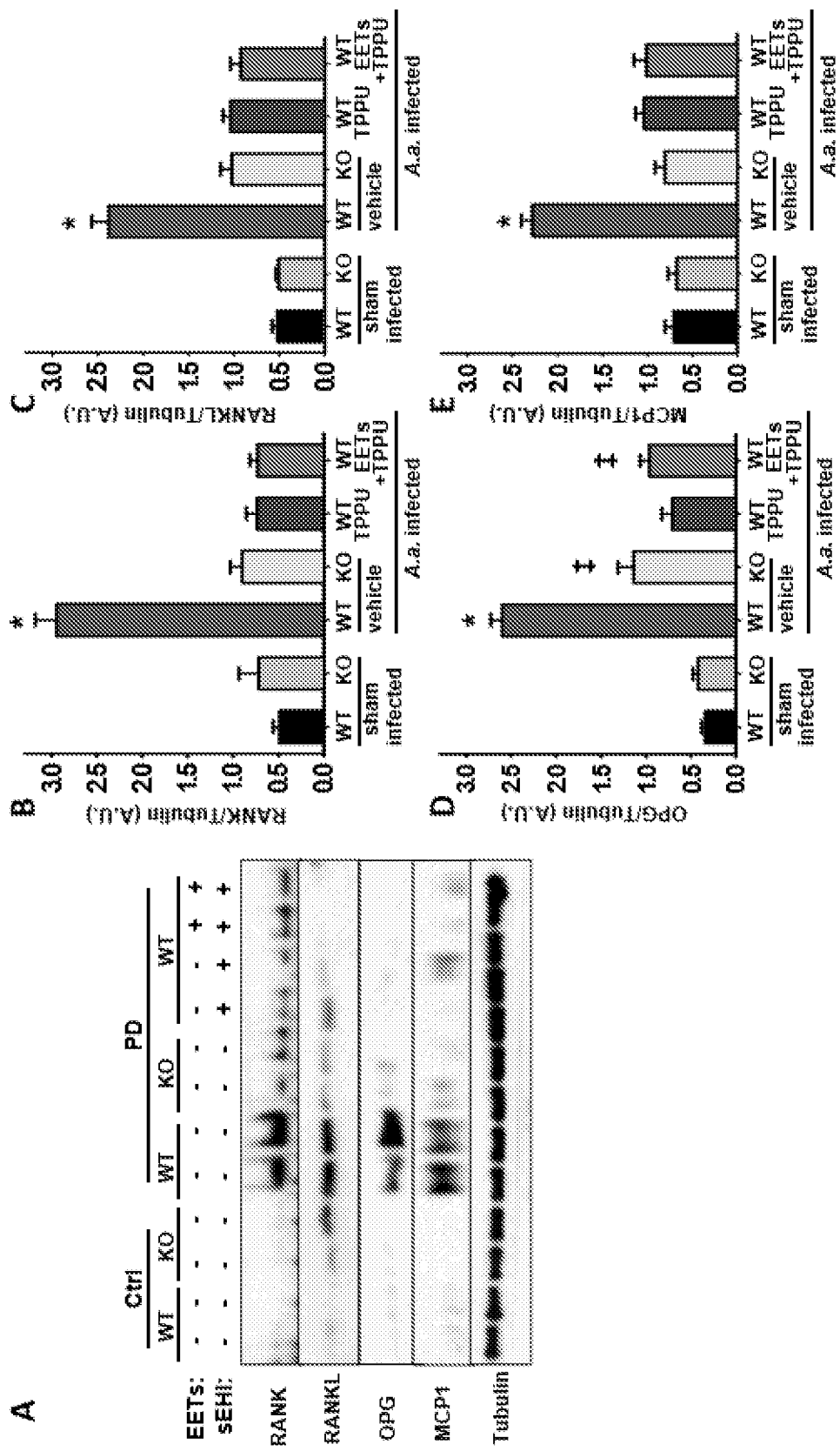
Fig. 5A-E

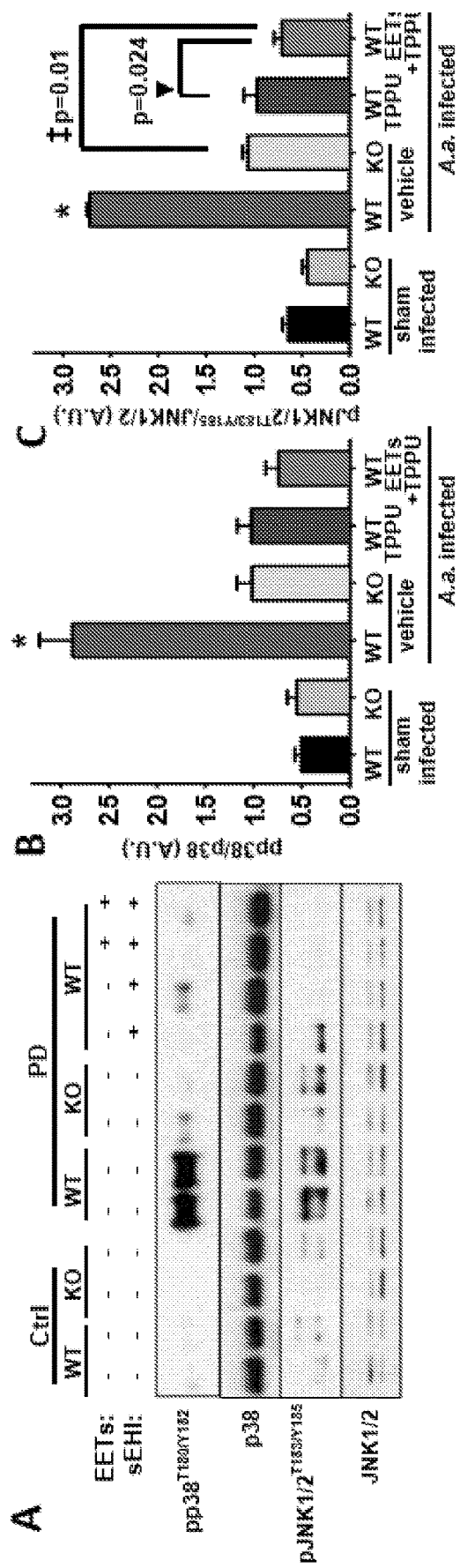
*Fig. 6A-C*

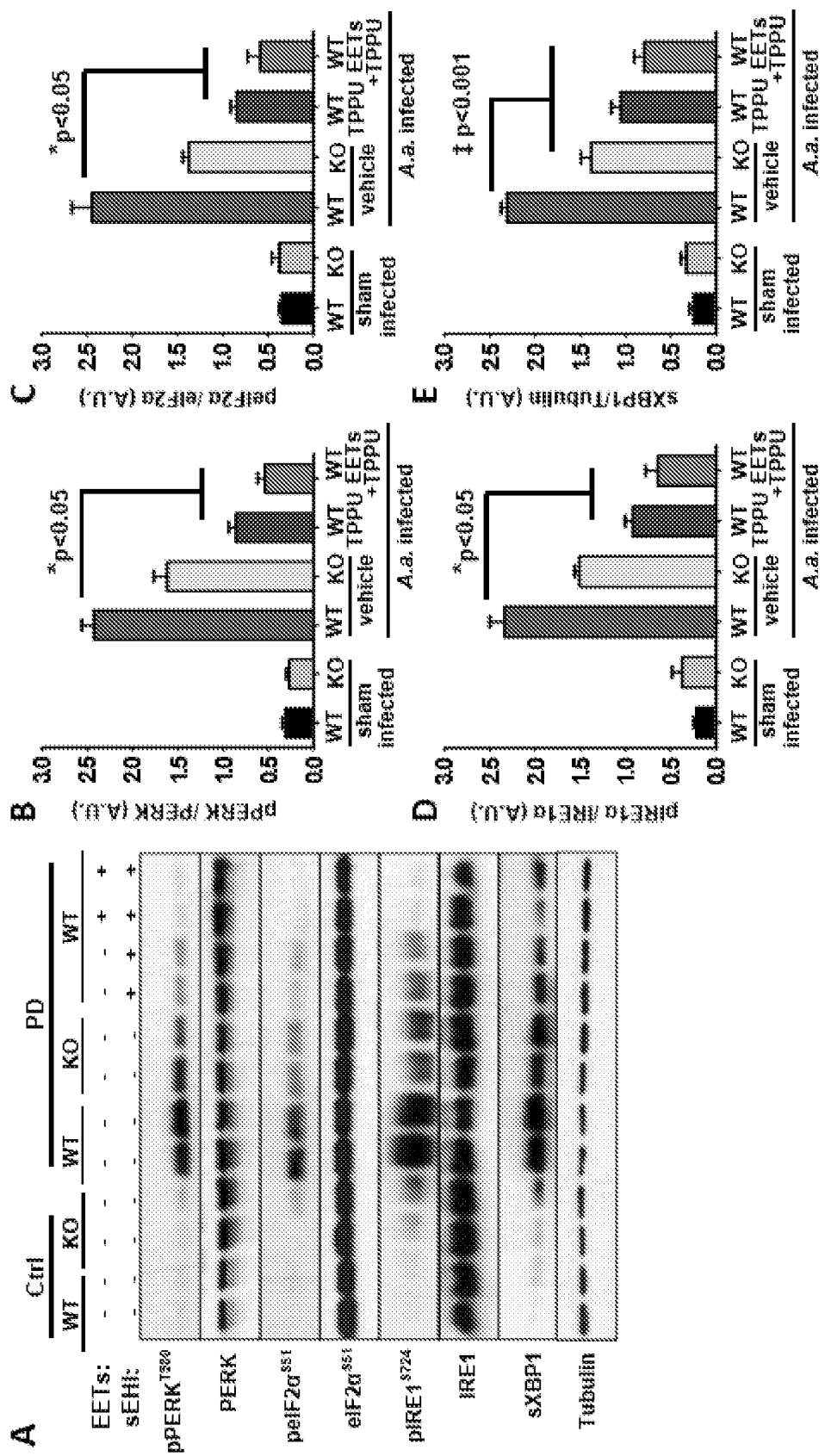
*Fig. 7A-E*

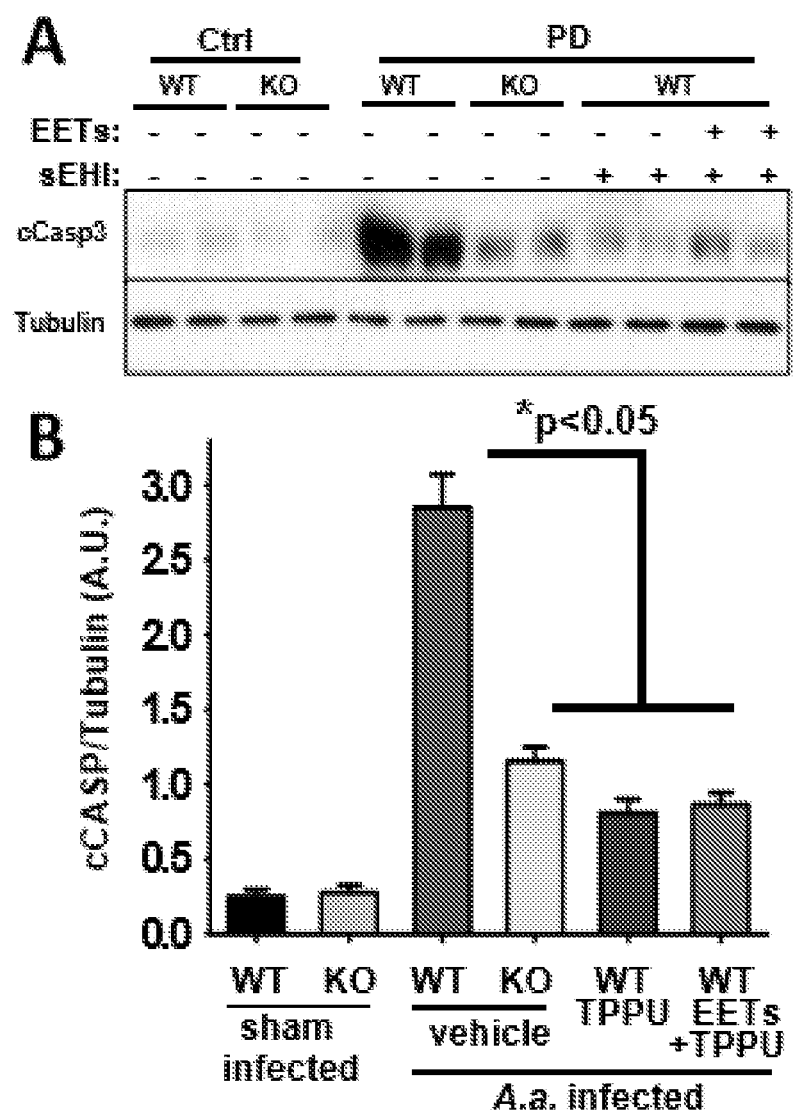
Fig. 8A-B

METHODS OF TREATING BONE LOSS

CROSS-REFERENCE TO RELATED APPLICATIONS

This application claims the benefit under 35 U.S.C. § 119(e) of U.S. Provisional Patent Application No. 62/348,144, filed on Jun. 10, 2016, which is hereby incorporated herein by reference in its entirety for all purposes.

STATEMENT OF GOVERNMENTAL SUPPORT

This work was supported in part by NIEHS/Superfund Research Program Grant Nos. R01ES002710, P42ES004699, ES025598-01A1 and 1K99ES024806; NIH Grant Nos. R01DK090492 and R01DK095359 and NIH/NIDDK Grant No. R00DK100736. The Government has certain rights in this invention.

BACKGROUND

Periodontitis is a chronic inflammatory disease of the supporting tissues of the teeth with progressive attachment loss and bone destruction (Flemmig, 1999). Dysbiosis is thought to be one of the major drivers of this condition. Imbalance in the periodontal microbiota, more specifically the relative abundance of individual species of bacteria was hypothesized to affect the host-microbe interactions, ultimately leading to destructive inflammation and bone loss (Hajishengallis et al., 2012). However, more recent findings bring up the possibility that overgrowth of bacteria may be a resulting outcome rather than the cause of periodontitis. Thus, it is likely that the host response to bacteria that leads to the tissue changes noted in gingivitis and periodontitis is the root cause (Bartold and Van Dyke, 2013).

In chronic osteolytic inflammatory diseases such as periodontitis, the failure of endogenous resolution pathways seem to lead to tissue destruction and conversely, augmentation of these natural defensive mechanisms can be an effective approach to control these diseases (Van Dyke, 2011). Resolution of inflammation is now widely accepted as an active process, in which endogenous antiinflammatory and pro-resolving mechanisms actively mediate wound healing and tissue regeneration as opposed to fibrosis and scarring (Levy et al., 2012; Ortega-Gomez et al., 2013). More recent studies provide supporting evidence for this concept, where endogenous control of inflammation directly improves bone healing and regeneration and suppresses the flow of destructive inflammatory infiltrate into the tissue (Hasturk et al., 2007; Napimoga et al., 2012).

Arachidonic acid (ARA) is an omega-6 polyunsaturated fatty acid constituting the phospholipid domain of most cell membranes. It is released by phospholipases such as cytoplasmic PLA2 and is metabolized into eicosanoids through three main routes, via prostaglandin-endoperoxide synthase/cyclooxygenases (PTGS/COX), lipoxygenases (LOX), and via the cytochrome P450s (CYP), resulting in prostanoids leukotrienes and hydroxy-eicosatetraenoic acids (HETE) and epoxyeicosatrienoic acids (EETs). The CYP enzymes that utilize ARA as a substrate mainly produce EETs and the ω-hydroxyl metabolites 19- and 20-HETE. ARA is metabolized to four biologically active EET regioisomers, the 5,6-EET, 8,9-EET, 11,12-EET, and 14,15-EET. All EETs are then further metabolized into less active dihydroxy-eicosatrienoic acids (DHETs) by the enzyme soluble epoxide hydrolase (sEH, EC 3.3.2.10)(Morisseau and Hammock, 2013).

Existing drugs target the cyclooxygenase (COX) and lipoxygenase (LOX) branches of the ARA cascade (Marnett, 2009; Haeggstrom et al., 2010). These branches largely synthesize proinflammatory mediators such as the prostanoids and leukotrienes. Most recently discovered branch, the cytochrome P450 branch, however, has not been adequately exploited as a pharmaceutical target. This branch produces both anti- and to lesser degree pro-inflammatory metabolites, including the 19- and 20-hydroxy-eicosatetraenoic acids (19- and 20-HETE) (Williams et al., 2010). Notably, antiinflammatory epoxy fatty acids such as EETs, and EDPs (EpDPEs) are produced by cytochrome P450s (Spector, 2009; Imig, 2012). EETs seem to promote the resolution of inflammation, rather than prevent, in a manner similar to that exhibited by mediators in the LOX pathway (Serhan et al., 2011). EETs reduce inflammation, but are also analgesic, anti-fibrotic and anti-hypertensive, acting in both paracrine and autocrine fashion (Spector, 2009; Bettaieb et al., 2015; Harris et al., 2015). However, the in vivo instability of EETs because of their rapid metabolism by sEH impeded understanding the roles of these lipid mediators until the development of potent and orally available sEH pharmacological inhibitors became available (Chacos et al., 1983; Morisseau et al., 1999).

SUMMARY

In one aspect, provided are methods of preventing, mitigating, decreasing, inhibiting and/or reversing bone loss and/or bone resorption and/or increasing and/or promoting bone regeneration and remodeling in a subject in need thereof. In another aspect, provided are methods of preventing, mitigating, decreasing, inhibiting and/or reversing periodontitis and/or periodontal disease in a subject in need thereof. In another aspect, provided are methods of preventing, mitigating, decreasing, inhibiting and/or reversing vascular calcification in a subject in need thereof. In a further aspect, provided are methods of preventing, mitigating, decreasing, inhibiting and/or reversing tumor-induced osteoclastogenesis in a subject in need thereof. In a further aspect, provided are methods of preventing, decreasing and/or inhibiting the activation and/or expression of RANK (Receptor Activator of Nuclear Factor κB), RANKL (RANK ligand) and/or monocyte chemoattractant protein-1 (MCP-1) in a subject in need thereof.

In varying embodiments, the methods comprise administering to the subject an agent that increases the production and/or level of epoxygenated fatty acids. In some embodiments, the agent that increases the production and/or level of epoxygenated fatty acids comprises one or more epoxygenated fatty acids. In some embodiments, the epoxygenated fatty acids are selected from the group consisting of cis-epoxyeicosantrienoic acids ("EETs"), epoxides of linoleic acid, epoxides of eicosapentaenoic acid ("EPA"), epoxides of docosahexaenoic acid ("DHA"), epoxides of the arachidonic acid ("AA"), epoxides of cis-7,10,13,16,19-docosapentaenoic acid, and mixtures thereof. In some embodiments, the agent that increases the production and/or level of epoxygenated fatty acids increases the production and/or levels of cis-epoxyeicosantrienoic acids ("EETs"). In varying embodiments, the methods comprise administering to the subject an effective amount of an inhibitor of soluble epoxide hydrolase (sEH). In varying embodiments, the inhibitor of sEH comprises an inhibitory nucleic acid that specifically targets soluble epoxide hydrolase ("sEH"). In varying embodiments, the inhibitory nucleic acid is selected from the group consisting of short interfering RNA (siRNA), short hairpin RNA (shRNA), small temporal RNA (stRNA), and micro-RNA (miRNA). In varying embodiments, the inhibitor of sEH comprises a primary pharmacophore selected from the group consisting of a urea, a carbamate, and an amide. In varying embodiments, the inhibitor of sEH comprises a cyclohexyl moiety, aromatic moiety, substituted aromatic moiety or alkyl moiety attached to the pharmacophore. In varying embodiments, the inhibitor of sEH comprises a cyclohexyl ether moiety attached to the pharmacophore. In varying embodiments, the inhibitor of sEH comprises a phenyl ether or piperidine moiety attached to the pharmacophore. In varying embodiments, the inhibitor of sEH comprises a polyether secondary pharmacophore. In varying embodiments, the inhibitor of sEH has an IC50 of less than about 100 µM, e.g. less than about 50 µM, 40 µM, 30 µM, 25 µM, 20 µM, 15 µM, 10 µM, 5 µM, 3 µM, 2 µM, 1 µM, 100 nM, 10 nM, 1.0 nM, or even less.

In varying embodiments of the methods, the inhibitor of sEH is selected from the group consisting of:
a) 3-(4-chlorophenyl)-1-(3,4-dichlorphenyl)urea or 3,4,4'-trichlorocarbanilide (TCC; compound 295);
b) 12-(3-adamantan-1-yl-ureido) dodecanoic acid (AUDA; compound 700);
c) 1-adamantanyl-3-{5-[2-(2-ethoxyethoxy)ethoxy]pentyl}urea (AEPU; compound 950);
d) 1-(1-acetypiperidin-4-yl)-3-adamantanylurea (APAU; compound 1153);
e) trans-4-[4-(3-Adamantan-1-yl-ureido)-cyclohexyloxy]-benzoic acid (tAUCB; compound 1471);
f) cis-4-[4-(3-Adamantan-1-yl-ureido)-cyclohexyloxy]-benzoic acid (cAUCB; compound 1686);
g) 1-(1-methylsulfonyl-piperidin-4-yl)-3-(4-trifluoromethoxy-phenyl)-urea (TUPS; compound 1709);
h) trans-4-{4-[3-(4-Trifluoromethoxy-phenyl)-ureido]-cyclohexyloxy}-benzoic acid (tTUCB; compound 1728);
i) 1-trifluoromethoxyphenyl-3-(1-propionylpiperidin-4-yl) urea (TPPU; compound 1770);
j) 1-(1-ethylsulfonyl-piperidin-4-yl)-3-(4-trifluoromethoxy-phenyl)-urea (TUPSE; compound 2213);
k) 1-(1-(cyclopropanecarbonyl)piperidin-4-yl)-3-(4-(trifluoromethoxy)phenyl)urea (CPTU; compound 2214);
l) trans-N-methyl-4-[4-(3-Adamantan-1-yl-ureido)-cyclohexyloxy]-benzamide (tMAUCB; compound 2225);
m) trans-N-methyl-4-[4-((3-trifluoromethyl-4-chlorophenyl)-ureido)-cyclohexyloxy]-benzamide (tMTCUCB; compound 2226);
n) cis-N-methyl-4-{4-[3-(4-trifluoromethoxy-phenyl)-ureido]-cyclohexyloxy}-benzamide (cMTUCB; compound 2228);
o) 1-cycloheptyl-3-(3-(1,5-diphenyl-1H-pyrazol-3-yl)propyl)urea (HDP3U; compound 2247);
p) trans-2-(4-(4-(3-(4-trifluoromethoxy-phenyl)-ureido)-cyclohexyloxy)-benzamido)-acetic acid (compound 2283);
q) N-(methylsulfonyl)-4-(trans-4-(3-(4-trifluoromethoxy-phenyl)-ureido)-cyclohexyloxy)-benzamide (compound 2728);
r) 1-(trans-4-(4-(1H-tetrazol-5-yl)-phenoxy)-cyclohexyl)-3-(4-(trifluoromethoxy)-phenyl)-urea (compound 2806);
s) 4-(trans-4-(3-(2-fluorophenyl)-ureido)-cyclohexyloxy)-benzoic acid (compound 2736);
t) 4-(4-(3-(4-(trifluoromethoxy)-phenyl)-ureido)-phenoxy)-benzoic acid (compound 2803);
u) 4-(3-fluoro-4-(3-(4-(trifluoromethoxy)-phenyl)-ureido)-phenoxy)-benzoic acid (compound 2807);
v) N-hydroxy-4-(trans-4-(3-(4-(trifluoromethoxy)-phenyl)-ureido)-cyclohexyloxy)-benzamide (compound 2761);
w) (5-methyl-2-oxo-1,3-dioxol-4-yl)methyl 4-((1r,4r)-4-(3-(4-(trifluoromethoxy)-phenyl)-ureido)-cyclohexyloxy)-benzoate (compound 2796);
x) 1-(4-oxocyclohexyl)-3-(4-(trifluoromethoxy)-phenyl)-urea (compound 2809);
y) methyl 4-(4-(3-(4-(trifluoromethoxy)-phenyl)-ureido)-cyclohexylamino)-benzoate (compound 2804);
z) 1-(4-(pyrimidin-2-yloxy)-cyclohexyl)-3-(4-(trifluoromethoxy)-phenyl)-urea (compound 2810); and
aa) 4-(trans-4-(3-(4-(difluoromethoxy)-phenyl)-ureido)-cyclohexyloxy)-benzoic acid (compound 2805).

In varying embodiments of the methods, the subject is a human, a canine or a feline. In some embodiments, the subject is exhibiting symptoms of bone loss. In some embodiments, the subject is exhibiting symptoms of osteoporosis. In some embodiments, the subject is exhibiting symptoms of periodontal disease. In some embodiments, the subject is receiving cancer chemotherapy. In some embodiments, the subject is in cancer remission. In some embodiments, the agent that increases the production and/or level of epoxygenated fatty acids is administered orally, buccally, transmucosally or topically. In some embodiments, the agent that increases the production and/or level of epoxygenated fatty acids is administered to the oral cavity.

In varying embodiments, the methods further comprise co-administering an inhibitor of endoplasmic reticular (ER) stress. In varying embodiments, the inhibitor of ER stress acts as a molecular chaperone that facilitates correct protein folding and/or prevents protein aggregation and/or acts to enhance autophagy. In varying embodiments, the inhibitor of ER stress modifies protein folding, regulates glucose homeostasis and/or reduces lipid overload. In some embodiments, the inhibitor of endoplasmic reticular stress performs one or more of the following: a) prevents, reduces and/or inhibits phosphorylation of PERK (Thr980), Ire1α (Ser727), eIF2α (Ser51), p38 and/or JNK1/2; b) prevents, reduces and/or inhibits cleavage of ATF6 and/or XBP1; and/or c) prevents, reduces and/or inhibits mRNA expression of BiP, ATF4 and/or XBP1. In some embodiments, the inhibitor of endoplasmic reticular stress is selected from the group consisting of 4-phenyl butyric acid ("PBA"), 3-phenylpropionic acid (3-PPA), 5-phenylvaleric acid (5-PVA), 6-phenylhexanoic acid (6-PHA), butyrate, tauroursodeoxycholic acid, trehalose, deuterated water, docosahexaenoic acid ("DHA"), eicosapentaenoic acid ("EPA"), vitamin C, arabitol, mannose, glycerol, betaine, sarcosine, trimethylamine-N oxide, DMSO and mixtures thereof. In some embodiments, the inhibitor of endoplasmic reticular stress is selected from the group consisting of 4-phenyl butyric acid (4-PBA), 3-phenylpropionic acid (3-PPA), 5-phenylvaleric acid (5-PVA), 6 phenylhexanoic acid (6-PHA), esters thereof, pharmaceutically acceptable salts thereof, and mixtures thereof. In some embodiments, one or both of the agent that increases the production and/or level of epoxygenated fatty acids and the inhibitor of endoplasmic reticular stress are administered at a subtherapeutic dose.

In another aspect, provided are oral compositions comprising an agent that increases the production and/or level of epoxygenated fatty acids. In varying embodiments, the oral composition is selected from the group consisting of a toothpaste, a mouthwash, an oral gel, an oral varnish, and an oral mucoadhesive. In some embodiments, the agent that increases the production and/or level of epoxygenated fatty acids comprises one or more epoxygenated fatty acids. In some embodiments, the epoxygenated fatty acids are selected from the group consisting of cis-epoxyeicosantrienoic acids ("EETs"), epoxides of linoleic acid, epoxides of eicosapentaenoic acid ("EPA"), epoxides of docosahexaenoic acid ("DHA"), epoxides of the arachidonic acid ("AA"), epoxides of cis-7,10,13,16,19-docosapentaenoic acid, and mixtures thereof. In some embodiments, the agent that increases the production and/or level of epoxygenated fatty acids increases the production and/or levels of cis-epoxyeicosantrienoic acids ("EETs"). In some embodiments, the agent that increases the production and/or level of EETs is an inhibitor of soluble epoxide hydrolase ("sEH"). In some embodiments, the inhibitor of sEH comprises an inhibitory nucleic acid that specifically targets soluble epoxide hydrolase ("sEH"). In varying embodiments, the inhibitory nucleic acid is selected from the group consisting of short interfering RNA (siRNA), short hairpin RNA (shRNA), small temporal RNA (stRNA), and micro-RNA (miRNA). In varying embodiments, the inhibitor of sEH comprises a primary pharmacophore selected from the group consisting of a urea, a carbamate, and an amide. In some embodiments, the inhibitor of sEH comprises a cyclohexyl moiety, aromatic moiety, substituted aromatic moiety or alkyl moiety attached to the pharmacophore. In some embodiments, the inhibitor of sEH comprises a cyclohexyl ether moiety attached to the pharmacophore. In varying embodiments, the inhibitor of sEH comprises a phenyl ether or piperidine moiety attached to the pharmacophore. In varying embodiments, the inhibitor of sEH comprises a polyether secondary pharmacophore. In varying embodiments, the inhibitor of sEH has an IC50 of less than about 100 µM.

In varying embodiments of the oral compositions, the inhibitor of sEH is selected from the group consisting of:
a) 3-(4-chlorophenyl)-1-(3,4-dichlorphenyl)urea or 3,4,4'-trichlorocarbanilide (TCC; compound 295);
b) 12-(3-adamantan-1-yl-ureido) dodecanoic acid (AUDA; compound 700);
c) 1-adamantanyl-3-{5-[2-(2-ethoxyethoxy)ethoxy]pentyl}urea (AEPU; compound 950);
d) 1-(1-acetypiperidin-4-yl)-3-adamantanylurea (APAU; compound 1153);
e) trans-4-[4-(3-Adamantan-1-yl-ureido)-cyclohexyloxy]-benzoic acid (tAUCB; compound 1471);
f) cis-4-[4-(3-Adamantan-1-yl-ureido)-cyclohexyloxy]-benzoic acid (cAUCB; compound 1686);
g) 1-(1-methylsulfonyl-piperidin-4-yl)-3-(4-trifluoromethoxy-phenyl)-urea (TUPS; compound 1709);
h) trans-4-{4-[3-(4-Trifluoromethoxy-phenyl)-ureido]-cyclohexyloxy}-benzoic acid (tTUCB; compound 1728);
i) 1-trifluoromethoxyphenyl-3-(1-propionylpiperidin-4-yl) urea (TPPU; compound 1770);
j) 1-(1-ethylsulfonyl-piperidin-4-yl)-3-(4-trifluoromethoxy-phenyl)-urea (TUPSE; compound 2213);
k) 1-(1-(cyclopropanecarbonyl)piperidin-4-yl)-3-(4-(trifluoromethoxy)phenyl)urea (CPTU; compound 2214);
l) trans-N-methyl-4-[4-(3-Adamantan-1-yl-ureido)-cyclohexyloxy]-benzamide (tMAUCB; compound 2225);
m) trans-N-methyl-4-[4-((3-trifluoromethyl-4-chlorophenyl)-ureido)-cyclohexyloxy]-benzamide (tMTCUCB; compound 2226);
n) cis-N-methyl-4-{4-[3-(4-trifluoromethoxy-phenyl)-ureido]-cyclohexyloxy}-benzamide (cMTUCB; compound 2228);
o) 1-cycloheptyl-3-(3-(1,5-diphenyl-1H-pyrazol-3-yl)propyl)urea (HDP3U; compound 2247);
p) trans-2-(4-(4-(3-(4-trifluoromethoxy-phenyl)-ureido)-cyclohexyloxy)-benzamido)-acetic acid (compound 2283);
q) N-(methylsulfonyl)-4-(trans-4-(3-(4-trifluoromethoxy-phenyl)-ureido)-cyclohexyloxy)-benzamide (compound 2728);
r) 1-(trans-4-(4-(1H-tetrazol-5-yl)-phenoxy)-cyclohexyl)-3-(4-(trifluoromethoxy)-phenyl)-urea (compound 2806);
s) 4-(trans-4-(3-(2-fluorophenyl)-ureido)-cyclohexyloxy)-benzoic acid (compound 2736);
t) 4-(4-(3-(4-(trifluoromethoxy)-phenyl)-ureido)-phenoxy)-benzoic acid (compound 2803);
u) 4-(3-fluoro-4-(3-(4-(trifluoromethoxy)-phenyl)-ureido)-phenoxy)-benzoic acid (compound 2807);
v) N-hydroxy-4-(trans-4-(3-(4-(trifluoromethoxy)-phenyl)-ureido)-cyclohexyloxy)-benzamide (compound 2761);
w) (5-methyl-2-oxo-1,3-dioxol-4-yl)methyl 4-((1r,4r)-4-(3-(4-(trifluoromethoxy)-phenyl)-ureido)-cyclohexyloxy)-benzoate (compound 2796);
x) 1-(4-oxocyclohexyl)-3-(4-(trifluoromethoxy)-phenyl)-urea (compound 2809);
y) methyl 4-(4-(3-(4-(trifluoromethoxy)-phenyl)-ureido)-cyclohexylamino)-benzoate (compound 2804);
z) 1-(4-(pyrimidin-2-yloxy)-cyclohexyl)-3-(4-(trifluoromethoxy)-phenyl)-urea (compound 2810); and
aa) 4-(trans-4-(3-(4-(difluoromethoxy)-phenyl)-ureido)-cyclohexyloxy)-benzoic acid (compound 2805).

DEFINITIONS

Units, prefixes, and symbols are denoted in their Systeme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments, which can be had by reference to the specification as a whole. Accordingly, the terms defined immediately below are more fully defined by reference to the specification in its entirety. Terms not defined herein have their ordinary meaning as understood by a person of skill in the art.

The phrase "endoplasmic reticulum (ER) stress" refers to disruption of processes performed by the endoplasmic reticulum, including the synthesis, modification, folding and delivery of proteins to their proper target sites within the secretory pathway and the extracellular space. ER stress can be caused by, e.g., disruption of protein folding, aberrations in lipid metabolism, or disruption of cell wall biogenesis. See, e.g., Schröder and Kaufman, *Mutation Research* (2005) 569:29-63.

"cis-Epoxyeicosatrienoic acids" ("EETs") are biomediators synthesized by cytochrome P450 epoxygenases. As discussed further in a separate section below, while the use of unmodified EETs is the most preferred, derivatives of EETs, such as amides and esters (both natural and synthetic), EETs analogs, and EETs optical isomers can all be used in the methods, both in pure form and as mixtures of these forms. For convenience of reference, the term "EETs" as used herein refers to all of these forms unless otherwise required by context.

"Epoxide hydrolases" ("EH;" EC 3.3.2.3) are enzymes in the alpha beta hydrolase fold family that add water to 3-membered cyclic ethers termed epoxides.

"Soluble epoxide hydrolase" ("sEH") is an epoxide hydrolase which in endothelial and smooth muscle cells converts EETs to dihydroxy derivatives called dihydroxyeicosatrienoic acids ("DHETs"). The cloning and sequence of the murine sEH is set forth in Grant et al., J. Biol. Chem. 268(23):17628-17633 (1993). The cloning, sequence, and accession numbers of the human sEH sequence are set forth in Beetham et al., Arch. Biochem. Biophys. 305(1):197-201 (1993). The amino acid sequence of human sEH is SEQ ID NO.:1, while the nucleic acid sequence encoding the human sEH is SEQ ID NO.:2. (The sequence set forth as SEQ ID NO.:2 is the coding portion of the sequence set forth in the Beetham et al. 1993 paper and in the NCBI Entrez Nucleotide Browser at accession number L05779, which include the 5' untranslated region and the 3' untranslated region.) The evolution and nomenclature of the gene is discussed in Beetham et al., DNA Cell Biol. 14(1):61-71 (1995). Soluble epoxide hydrolase represents a single highly conserved gene product with over 90% homology between rodent and human (Arand et al., FEBS Lett., 338:251-256 (1994)). Unless otherwise specified, as used herein, the terms "soluble epoxide hydrolase" and "sEH" refer to human sEH.

Unless otherwise specified, as used herein, the term "sEH inhibitor" (also abbreviated as "sEHI") refers to an inhibitor of human sEH. Preferably, the inhibitor does not also inhibit the activity of microsomal epoxide hydrolase by more than 25% at concentrations at which the inhibitor inhibits sEH by at least 50%, and more preferably does not inhibit mEH by more than 10% at that concentration. For convenience of reference, unless otherwise required by context, the term "sEH inhibitor" as used herein encompasses prodrugs which are metabolized to active inhibitors of sEH. Further for convenience of reference, and except as otherwise required by context, reference herein to a compound as an inhibitor of sEH includes reference to derivatives of that compound (such as an ester of that compound) that retain activity as an sEH inhibitor.

Cytochrome P450 ("CYP450") metabolism produces cis-epoxydocosapentaenoic acids ("EpDPEs") and cis-epoxyeicosatetraenoic acids ("EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS- (nitric oxide) and COX-derived (prostacyclin) vasodilators. Overall cytochrome P450 (CYP450) metabolism of polyunsaturated fatty acids produces epoxides, such as EETs, which are prime candidates for the active mediator(s). 14(15)-EpETE, for example, is derived via epoxidation of the 14,15-double bond of EPA and is the ω-3 homolog of 14(15)-EpETrE ("14(15)EET") derived via epoxidation of the 14,15-double bond of arachidonic acid.

"$IC_{50}$" refers to the concentration of an agent required to inhibit enzyme activity by 50%. Similarly, "$IC_{90}$" refers to the concentration of an agent required to inhibit enzyme activity by 90%.

The term "neuroactive steroid" or "neurosteroids" interchangeably refer to steroids that rapidly alter neuronal excitability through interaction with neurotransmitter-gated ion channels, and which may also exert effects on gene expression via intracellular steroid hormone receptors. Neurosteroids have a wide range of applications from sedation to treatment of epilepsy and traumatic brain injury. Neurosteroids can act as allosteric modulators of neurotransmitter receptors, such as $GABA_A$, NMDA, and sigma receptors. Progesterone (PROG) is also a neurosteroid which activates progesterone receptors expressed in peripheral and central glial cells. Several synthetic neurosteroids have been used as sedatives for the purpose of general anaesthesia for carrying out surgical procedures. Exemplary sedating neurosteroids include without limitation alphaxolone, alphadolone, hydroxydione and minaxolone.

By "physiological conditions" is meant an extracellular milieu having conditions (e.g., temperature, pH, and osmolarity) which allows for the sustenance or growth of a cell of interest.

"Micro-RNA" ("miRNA") refers to small, noncoding RNAs of 18-25 nt in length that negatively regulate their complementary mRNAs at the posttranscriptional level in many eukaryotic organisms. See, e.g., Kurihara and Watanabe, Proc Natl Acad Sci USA 101(34):12753-12758 (2004). Micro-RNA's were first discovered in the roundworm C. elegans in the early 1990s and are now known in many species, including humans. As used herein, it refers to exogenously administered miRNA unless specifically noted or otherwise required by context.

The term "therapeutically effective amount" refers to that amount of the compound being administered sufficient to prevent or decrease the development of one or more of the symptoms of the disease, condition or disorder being treated (e.g., bone loss, osteoporosis, periodontal disease, vascular calcification, osteoclastogenesis, and/or activation and/or expression of RANK (Receptor Activator of Nuclear Factor κB), RANKL (RANK ligand) and/or monocyte chemoattractant protein-1 (MCP-1)).

The terms "prophylactically effective amount" and "amount that is effective to prevent" refer to that amount of drug that will prevent or reduce the risk of occurrence of the biological or medical event that is sought to be prevented. In many instances, the prophylactically effective amount is the same as the therapeutically effective amount.

"Subtherapeutic dose" refers to a dose of a pharmacologically active agent(s), either as an administered dose of pharmacologically active agent, or actual level of pharmacologically active agent in a subject that functionally is insufficient to elicit the intended pharmacological effect in itself (e.g., to obtain analgesic, anti-inflammatory, and/or anti-fibrotic effects), or that quantitatively is less than the established therapeutic dose for that particular pharmacological agent (e.g., as published in a reference consulted by a person of skill, for example, doses for a pharmacological agent published in the Physicians' Desk Reference, 70th Ed., 2016, PDR Network or Brunton, et al., Goodman & Gilman's The Pharmacological Basis of Therapeutics, 12th edition, 2010, McGraw-Hill Professional). A "subtherapeutic dose" can be defined in relative terms (i.e., as a percentage amount (less than 100%) of the amount of pharmacologically active agent conventionally administered). For example, a subtherapeutic dose amount can be about 1% to about 75% of the amount of pharmacologically active agent conventionally administered. In some embodiments, a subtherapeutic dose can be about 75%, 50%, 30%, 25%, 20%, 10% or less, than the amount of pharmacologically active agent conventionally administered.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in Remington: The Science and Practice of Pharmacy, University of the Sciences in Philadelphia, Eds., 21$^{st}$ Ed., Lippencott Williams & Wilkins (2005).

The terms "sustained release" and "extended release" are used in their conventional sense to refer to a drug formulation that provides for gradual release of a drug over an extended period of time, for example, 12 hours or more, and that preferably, although not necessarily, results in substantially steady-state blood levels of a drug over an extended time period.

As used herein, the term "delayed release" refers to a pharmaceutical preparation that passes through the stomach intact and dissolves in the small intestine.

As used herein, "synergy" or "synergistic" interchangeably refer to the combined effects of two active agents that are greater than their additive effects. Synergy can also be achieved by producing an efficacious effect with combined inefficacious doses of two active agents. The measure of synergy is independent of statistical significance.

The terms "systemic administration" and "systemically administered" refer to a method of administering agent (e.g., an agent that reduces or inhibits ER stress, an agent that increases epoxygenated fatty acids (e.g., an inhibitor of sEH, an EET, an epoxygenated fatty acid, and mixtures thereof), optionally with an anti-inflammatory agent and/or an analgesic agent) to a mammal so that the agent/cells is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration.

The term "co-administration" refers to the presence of both active agents/cells in the blood or body at the same time. Active agents that are co-administered can be delivered concurrently (i.e., at the same time) or sequentially.

The phrase "cause to be administered" refers to the actions taken by a medical professional (e.g., a physician), or a person controlling medical care of a subject, that control and/or permit the administration of the agent(s)/compound(s)/cell(s) at issue to the subject. Causing to be administered can involve diagnosis and/or determination of an appropriate therapeutic or prophylactic regimen, and/or prescribing particular agent(s)/compounds/cell(s) for a subject. Such prescribing can include, for example, drafting a prescription form, annotating a medical record, and the like.

The terms "patient," "subject" or "individual" interchangeably refers to a human or a non-human mammal, including primates (e.g., macaque, pan troglodyte, pongo), a domesticated mammal (e.g., felines, canines), an agricultural mammal (e.g., bovine, ovine, porcine, equine) and a laboratory mammal or rodent (e.g., *rattus*, murine, lagomorpha, hamster).

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

The terms "inhibiting," "reducing," "decreasing" refers to inhibiting the bone loss, osteoporosis, periodontal disease, vascular calcification, osteoclastogenesis, and/or activation and/or expression of RANK (Receptor Activator of Nuclear Factor κB), RANKL (RANK ligand) and/or monocyte chemoattractant protein-1 (MCP-1) in a non-human mammalian subject by a measurable amount using any method known in the art. For example, bone loss, osteoporosis, periodontal disease, vascular calcification, osteoclastogenesis, and/or activation and/or expression of RANK (Receptor Activator of Nuclear Factor κB), RANKL (RANK ligand) and/or monocyte chemoattractant protein-1 (MCP-1) is inhibited, reduced or decreased if an indicator of bone loss, osteoporosis, periodontal disease, vascular calcification, osteoclastogenesis, and/or activation and/or expression of RANK (Receptor Activator of Nuclear Factor κB), RANKL (RANK ligand) and/or monocyte chemoattractant protein-1 (MCP-1), e.g., is at least about 10%, 20%, 30%, 50%, 80%, or 100% reduced, e.g., in comparison to the same indicator of bone loss, osteoporosis, periodontal disease, vascular calcification, osteoclastogenesis, and/or activation and/or expression of RANK (Receptor Activator of Nuclear Factor κB), RANKL (RANK ligand) and/or monocyte chemoattractant protein-1 (MCP-1) prior to administration of an agent that increases epoxygenated fatty acids (e.g., an inhibitor of sEH, an EET, an epoxygenated fatty acid, and mixtures thereof). In some embodiments, the bone loss, osteoporosis, periodontal disease, vascular calcification, osteoclastogenesis, and/or activation and/or expression of RANK (Receptor Activator of Nuclear Factor κB), RANKL (RANK ligand) and/or monocyte chemoattractant protein-1 (MCP-1) is inhibited, reduced or decreased by at least about 1-fold, 2-fold, 3-fold, 4-fold, or more in comparison to the bone loss, osteoporosis, periodontal disease, vascular calcification, osteoclastogenesis, and/or activation and/or expression of RANK (Receptor Activator of Nuclear Factor κB), RANKL (RANK ligand) and/or monocyte chemoattractant protein-1 (MCP-1) prior to administration of the agent that increases epoxygenated fatty acids (e.g., an inhibitor of sEH, an EET, an epoxygenated fatty acid, and mixtures thereof). Indicators of bone loss, osteoporosis, periodontal disease, vascular calcification, osteoclastogenesis, and/or activation and/or expression of RANK (Receptor Activator of Nuclear Factor κB), RANKL (RANK ligand) and/or monocyte chemoattractant protein-1 (MCP-1) can also be qualitative.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than the listed active agents, e.g., an agent that increases epoxygenated fatty acids (e.g., an inhibitor of sEH, an EET, an epoxygenated fatty acid, and mixtures thereof) and/or an anti-inflammatory agent.

BRIEF DESCRIPTION OF THE DRAWINGS

FIGS. 2A-F illustrate that inhibition of sEH with a potent and orally available small molecule TPPU decreases bone loss. Mice were inoculated with freshly grown cultures of *A. actinomycetemcomitans* on three consecutive days as described in the methods. The vehicle PEG400, TPPU (1 mg/kg) and EET methyl esters (1 μg/kg diluted in PEG400) were orally administered daily by gavage. Treatments continued until 15th day post infection and samples were obtained on the 16th day. Distance (μm) between the cement-enamel junction and the alveolar bone crest for all experimental groups were quantified. (A) The group vehicle alone developed significant bone loss, whereas groups treated with TPPU and TPPU+EET-methyl esters displayed a marked reduction in bone loss. Mice receiving EET-methyl esters were not different than vehicle treated infected mice, suggesting the necessity of inhibiting sEH for EETs to display activity. (B-F) Panels display deboned and methylene blue stained teeth from sham (B, n=8), mice infected with *A. actinomycetemcomitans* (C, n=14), EETmethyl ester (1 μg/kg/daily) treated (D, n=12), TPPU, 1 mg/kg treated (E, n=13), and EET-methyl ester+TPPU treated groups (F, n=13). The dark stained areas indicate sites of bone loss. The results are expressed as mean±SEM (*$p<0.001$, One-Way ANOVA followed by Student Newman Keuls post-hoc all pairwise comparison).

FIGS. 4A-E illustrate that genetic inhibition of sEH by gene knockout decreases bone loss similar to chemical inhibitor. sEH−/− and wild type C57/B6 mice were from a UC Davis maintained colony. Mice at age 6 weeks were infected with *A. actinomycetemcomitans* three consecutive times as described for FIG. 1 and at the end of the treatment period distance (μm) between the cement-enamel junction and the alveolar bone crest for all experimental groups were quantified. In parallel to the results with the sEH inhibitor TPPU the genetic knockout of sEH resulted in significantly reduced bone loss. Panels display wild type sham infected (B, n=8)), sEH−/− sham infected (C, n=15), wild type mice orally infected with *A. actinomycetemcomitans* (D, n=14), and sEH−/− mice, orally infected with *A. actinomycetemcomitans* (E, n=14). The dark stained areas indicate sites of bone loss. The results are expressed as mean±SEM (*$p<0.001$, One-Way ANOVA followed by Student Newman Keuls post-hoc all pairwise comparison).

FIGS. 5A-E illustrate that the dysregulated RANK/RANKL/OPG system in periodontal disease is restored by chemical or genetic ablation of sEH. Protein expression levels of osteoclastogenesis-related factors in gingival tissues from all experimental groups were investigated by Western blotting. For quantification, band intensity was normalized to that of α-tubulin. Protein band intensity is represented as arbitrary units. Density quantification included all animals and mean±SEM of each group (n=6 per group) are displayed in the bar graphs. (A) Original blots displaying two randomly selected animals. (B) Bar graphs of mean band intensity for, RANK (B), RANKL (C), OPG (D) and MCP-1 (E) measured for all six mice. (*$p<0.001$, ‡$p<0.03$, One-Way ANOVA followed by Student Newman Keuls post-hoc all pairwise comparison).

FIGS. 6A-C illustrate that periodontal disease mediated phosphorylation of pro-inflammatory p38 and JNK1/2 is reduced by chemical or genetic ablation of sEH. Phosphorylation and activation of p38 and JNK1/2 were quantified from all groups by normalizing band intensity to that of α-tubulin. (A) Original blots displaying two randomly selected animals. (B and C) Bar graphs of phosphorylation status of p38 and JNK1/2. Mean band intensity is measured for all six mice and are represented as arbitrary units (mean±SEM). (*$p<0.001$, ‡$p=0.01$, ▼$p=0.024$, One-Way ANOVA followed by Student Newman Keuls post-hoc all pairwise comparison).

FIGS. 7A-E illustrate that ER stress sensors are activated in gingival tissues of mice with periodontal disease and reversed by inhibition of sEH (A) Original blots displaying two randomly selected animals for each group. (B to E) Bar graphs of phosphorylation status of PERK, eIF2α, IRE-1α and expression level of sXBP-1 normalized to expression of α-tubulin. Mean band intensity is measured for all six mice and are represented as arbitrary units (mean±SEM). (‡$p<0.001$, *$p<0.05$, Kruskal-Wallis One Way Analysis of Variance on Ranks followed by Tukey's all pairwise multiple comparison post-hoc test).

FIGS. 8A-B illustrate that genetic ablation or chemical inhibition of sEH reduces apoptosis in gingivial tissue of mice infected with *A. actinomycetemcomitans*. (A) Original blot displaying two randomly selected animals for each group. Expression level of c-Caspase 3 is quantified by measuring band intensity for all six mice for each group and normalized to the expression level of α-tubulin. (B) Bar graph of mean Caspase-3 band intensity, represented as arbitrary units (mean±SEM). (*$p<0.05$, Kruskal-Wallis One Way Analysis of Variance on Ranks followed by Tukey's all pairwise multiple comparison posthoc test).

DETAILED DESCRIPTION

1. Introduction

Figure 1:
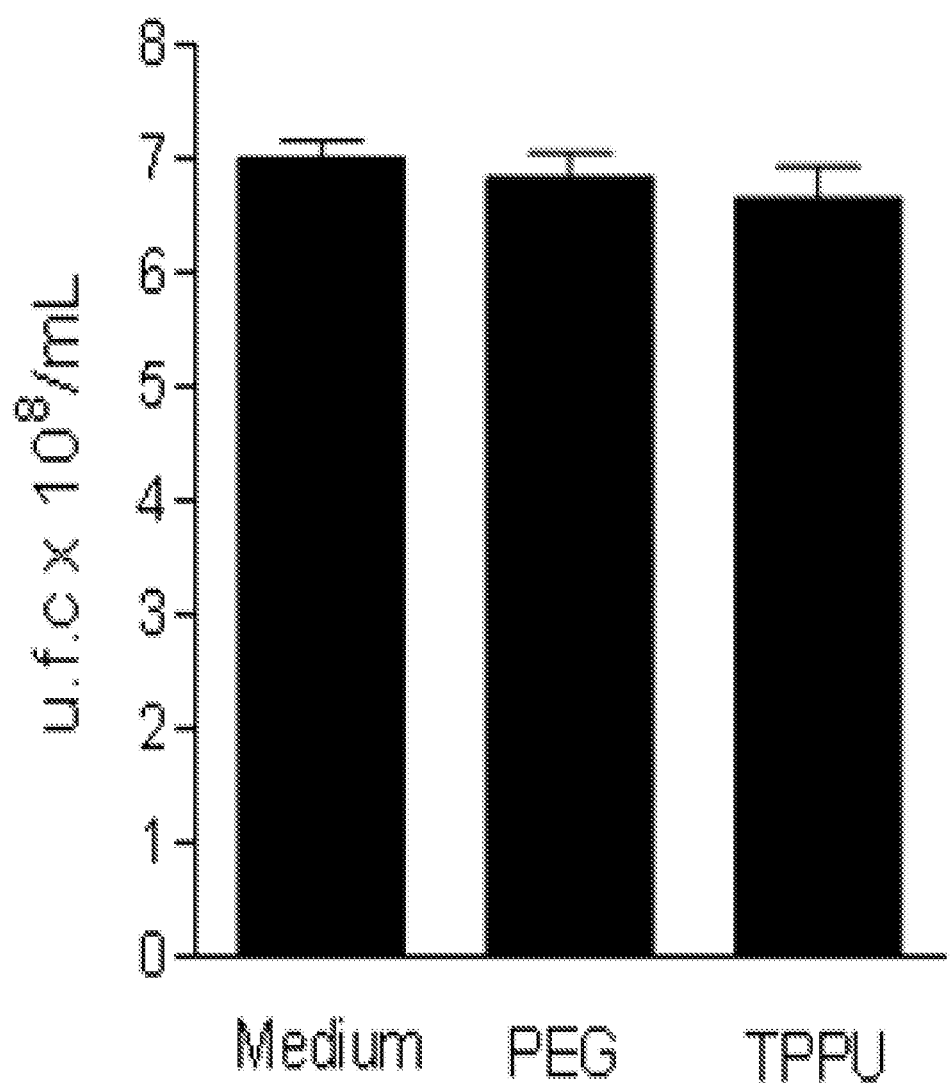
FIG. 1 illustrates that TPPU or its vehicle does not affect bacterial viability. The microbial inoculum of *A. actinomycetemcomitans* was prepared and adjusted to $5 \times 10^6$ colony forming units (CFU)/mL in tryptic soy broth. TPPU was then dissolved to a final concentration of 10 μM in 100% polyethylene glycol (PEG400; Fisher Scientific, Nidderau, Germany) and was added to the soy broth. Following incubation at 37° C. for 24 hours under anaerobic conditions, samples serially diluted and were plated on agar plates and colony forming units were counted the next day. PEG400 solution without the inhibitor was used as a control. The results are expressed as mean±SD.

Epoxyeicosatrienoic acids (EETs), metabolites of arachidonic acid derived from the cytochrome P450 (CYP450) enzymes, are mainly metabolized by soluble epoxide hydrolase (sEH) to their corresponding diols. EETs but not their diols, have anti-inflammatory properties and inhibition of sEH might provide protective effects against inflammatory bone loss. Thus, in the present study, we tested the selective sEH inhibitor, 1-trifluoromethoxyphenyl-3-(1-propionylpiperidin-4-yl) urea (TPPU) in a mouse model of periodontitis induced by infection with *A. actinomycetemcomitans*. Oral treatment of wild type mice with TPPU and sEH knockout (KO) animals showed reduced bone loss induced by *A. actinomycetemcomitans*. This was associated with decreased expression of key osteoclastogenic molecules RANK/RANKL/OPG and the chemokine MCP-1 in the gingival tissue without affecting bacterial counts. In addition, downstream kinases p38 and JNK known to be activated in response to inflammatory signals were abrogated after TPPU treatment or in sEH KO mice. Moreover, endoplasmic reticulum stress was elevated in periodontal disease but was abrogated after TPPU treatment and in sEH knockout mice. Together, these results demonstrated that sEH pharmacological inhibition is of therapeutic value in periodontitis.

The hydrolysis of EETs to DHETs by sEH was considered as an inactivation process in which bioactive metabolites were degraded to inactive products (Schmelzer et al., 2005). However, recent findings suggest that DHETs are also bioactive and are pro-inflammatory (Norwood et al., 2010), as are the diols linoleate epoxides (Viswanathan et al., 2003). Thus, sEH inhibition present a powerful approach for reducing inflammation not only by stabilizing the anti-inflammatory mediators, but also by reducing pro-inflammatory mediator production. Furthermore, sEH inhibitors act in synergy with existing anti-inflammatory drugs including COX and LOX inhibitors (Schmelzer et al., 2006; Liu et al., 2010), as well as anti-inflammatory phosphodiesterase (PDE) inhibitors (Inceoglu et al., 2011).

The current study demonstrates the utility of sEH pharmacological inhibition in periodontitis, in which we evaluated the effects of sEH inhibition and EETs on bone loss using a mouse model of bacterial periodontitis.

2. Subjects Who May Benefit—Conditions Subject to Treatment

Subjects who may benefit are exhibiting symptoms of or at risk of suffering bone loss or may benefit from promotion of bone growth or regeneration. For example, the subject may have or be suspected of having osteoporosis or periodontal disease, or may have or be suspected of having a bone fracture or broken bone. In varying embodiments, the bone loss is secondary to or caused by cancer and/or cancer chemotherapy. Symptoms of periodontal disease include without limitation, e.g., bad breath, red or swollen gums, tender or bleeding gums, painful chewing, loose teeth, sensitive teeth, receding gums and/or longer appearing teeth. Symptoms of osteoporosis include without limitation, e.g., back pain (e.g., caused by a fractured or collapsed vertebra), loss of height over time, stooped posture, and/or bone fracture(s) that occur much more easily than expected.

In varying embodiments, the subject is a child, a juvenile or an adult. In varying embodiments, the subject is a mammal, for example, human, a non-human primate, canine, feline, equine, bovine, ovine, porcine, lagomorpha, murine, or *rattus*.

3. Agents that Increase the Production and/or Level of Epoxygenated Fatty Acids

Agents that increase epoxygenated fatty acids include epoxygenated fatty acids (e.g., including EETs), and inhibitors of soluble epoxide hydrolase (sEH).

a. Inhibitors of Soluble Epoxide Hydrolase (sEH)

Scores of sEH inhibitors are known, of a variety of chemical structures. Derivatives in which the urea, carbamate or amide pharmacophore are particularly useful as sEH inhibitors. As used herein, "pharmacophore" refers to the section of the structure of a ligand that binds to the sEH. In various embodiments, the urea, carbamate or amide pharmacophore is covalently bound to both an adamantane and to a 12 carbon chain dodecane. Derivatives that are metabolically stable are preferred, as they are expected to have greater activity in vivo. Selective and competitive inhibition of sEH in vitro by a variety of urea, carbamate, and amide derivatives is taught, for example, by Morisseau et al., Proc. Natl. Acad. Sci. U.S.A, 96:8849-8854 (1999), which provides substantial guidance on designing urea derivatives that inhibit the enzyme.

Derivatives of urea are transition state mimetics that form a preferred group of sEH inhibitors. Within this group, N, N'-dodecyl-cyclohexyl urea (DCU), is preferred as an inhibitor, while N-cyclohexyl-N'-dodecylurea (CDU) is particularly preferred. Some compounds, such as dicyclohexylcarbodiimide (a lipophilic diimide), can decompose to an active urea inhibitor such as DCU. Any particular urea derivative or other compound can be easily tested for its ability to inhibit sEH by standard assays, such as those discussed herein. The production and testing of urea and carbamate derivatives as sEH inhibitors is set forth in detail in, for example, Morisseau et al., Proc Natl Acad Sci (USA) 96:8849-8854 (1999).

N-Adamantyl-N'-dodecyl urea ("ADU") is both metabolically stable and has particularly high activity on sEH. (Both the 1- and the 2-admamantyl ureas have been tested and have about the same high activity as an inhibitor of sEH. Thus, isomers of adamantyl dodecyl urea are preferred inhibitors. It is further expected that N, N'-dodecyl-cyclohexyl urea (DCU), and other inhibitors of sEH, and particularly dodecanoic acid ester derivatives of urea, are suitable for use in the methods. Preferred inhibitors include:

12-(3-Adamantan-1-yl-ureido)dodecanoic acid (AUDA),

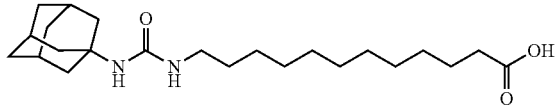 [SMILES: O=C(O)CCCCCCCCCCCNC(=O)NC12CC3CC(CC(C3)C1)C2]

12-(3-Adamantan-1-yl-ureido)dodecanoic acid butyl ester (AUDA-BE),

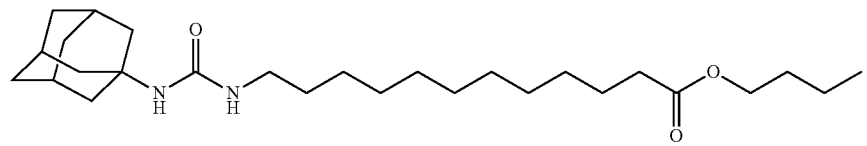 [SMILES: CCCCOC(=O)CCCCCCCCCCCNC(=O)NC12CC3CC(CC(C3)C1)C2]

Adamantan-1-yl-3-{5-[2-(2-ethoxyethoxy)ethoxy]pentyl}urea (compound 950, also referred to herein as "AEPU"), and

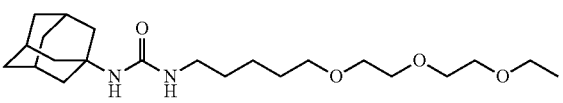 [SMILES: CCOCCOCCOCCCCCNC(=O)NC12CC3CC(CC(C3)C1)C2]

Another preferred group of inhibitors are piperidines. The following Tables sets forth some exemplar inhibitors of sEH and their ability to inhibit sEH activity of the human enzyme and sEH from equine, ovine, porcine, feline and canine, expressed as the amount needed to reduce the activity of the enzyme by 50% (expressed as "$IC_{50}$").

TABLE 1

IC$_{50}$ values for selected alkylpiperidine-based sEH inhibitors against human sEH

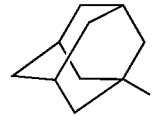

| R: | Compound (n=0) | IC$_{50}$ (μM)$^a$ | Compound (n=1) | IC$_{50}$ (μM)$^a$ |
|---|---|---|---|---|
| H | I | 0.30 | II | 4.2 |
| ethyl | 3a | 3.8 | 4.a | 3.9 |
| propyl | 3b | 0.81 | 4b | 2.6 |
| butyl | 3c | 1.2 | 4c | 0.61 |
| benzyl | 3d | 0.01 | 4d | 0.11 |

$^a$As determined via a kinetic fluorescent assay.

TABLE 2 sEH inhibitors

| Structure | Name | sEHi # |
|---|---|---|
| 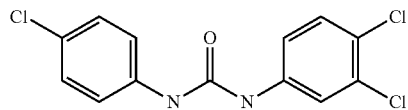 | 3-(4-chlorophenyl)-1-(3,4-dichlorphenyl)urea or 3,4,4'-trichlorocarbanilide | 295 (TCC) |
| 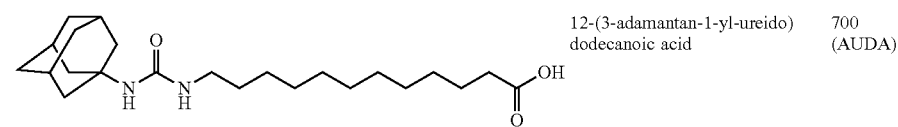 | 12-(3-adamantan-1-yl-ureido)dodecanoic acid | 700 (AUDA) |
| 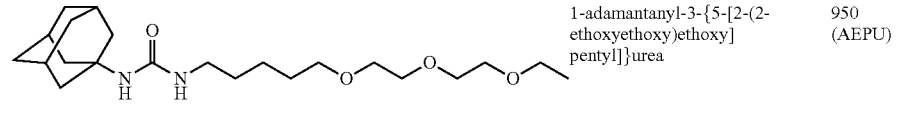 | 1-adamantanyl-3-{5-[2-(2-ethoxyethoxy)ethoxy]pentyl}urea | 950 (AEPU) |
| 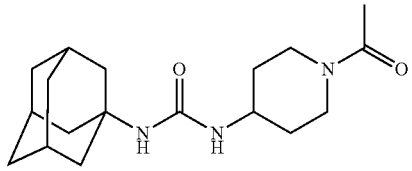 [SMILES: CC(=O)N1CCC(NC(=O)NC23CC4CC(CC(C4)C2)C3)CC1] | 1-(1-acetypiperidin-4-yl)-3-adamantanylurea | 1153 (APAU) |

TABLE 2-continued sEH inhibitors

| Structure | Name | sEHi # |
|---|---|---|
| 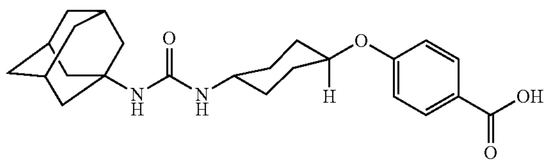 [SMILES: O=C(NC1CCC(Oc2ccc(C(=O)O)cc2)CC1)NC12CC3CC(CC(C3)C1)C2] | trans-4-[4-(3-Adamantan-1-yl-ureido)-cyclohexyloxy]-benzoic acid | 1471 (tAUCB) |
| 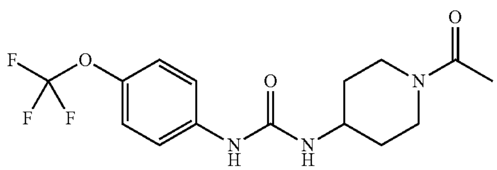 [SMILES: CC(=O)N1CCC(NC(=O)Nc2ccc(OC(F)(F)F)cc2)CC1] | 1-trifluoromethoxyphenyl-3-(1-acetylpiperidin-4-yl) urea | 1555 (TPAU) |
| 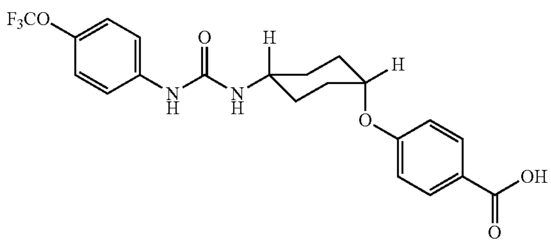 [SMILES: O=C(Nc1ccc(OC(F)(F)F)cc1)NC1CCC(Oc2ccc(C(=O)O)cc2)CC1] | cis-4-[4-(3-Adamantan-1-yl-ureido)-cyclohexyloxy]-benzoic acid | 1686 (cAUCB) |
| 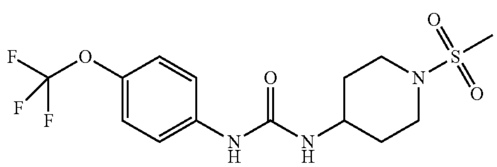 [SMILES: CS(=O)(=O)N1CCC(NC(=O)Nc2ccc(OC(F)(F)F)cc2)CC1] | 1-(1-methylsulfonyl-piperidin-4-yl)-3-(4-trifluoromethoxy-phenyl)-urea | 1709 (TUPS) |
| 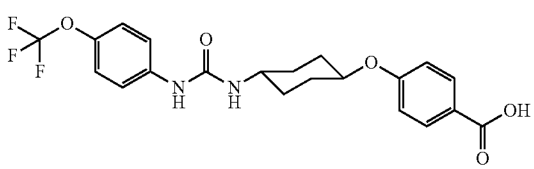 [SMILES: O=C(Nc1ccc(OC(F)(F)F)cc1)NC1CCC(Oc2ccc(C(=O)O)cc2)CC1] | trans-4-{4-[3-(4-Trifluoromethoxy-phenyl)-ureido]-cyclohexyloxy}-benzoic acid | 1728 (tTUCB) |
| | 1-trifluoromethoxyphenyl-3-(1-propionylpiperidin-4-yl) urea | 1770 (TPPU) |
| 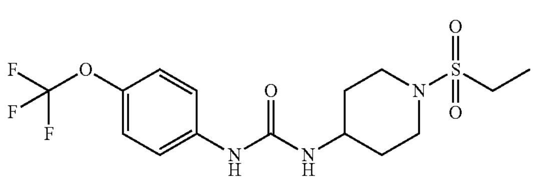 [SMILES: CCS(=O)(=O)N1CCC(NC(=O)Nc2ccc(OC(F)(F)F)cc2)CC1] | 1-(1-ethylsulfonyl-piperidin-4-yl)-3-(4-trifluoromethoxy-phenyl)-urea | 2213 (TUPSE) |
| 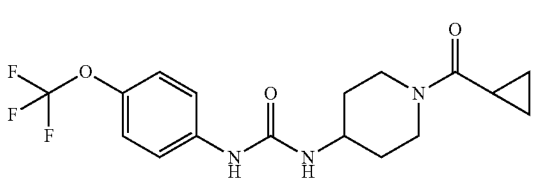 [SMILES: O=C(Nc1ccc(OC(F)(F)F)cc1)NC1CCN(C(=O)C2CC2)CC1] | 1-(1-(cyclopropanecarbonyl)piperidin-4-yl)-3-(4-(trifluoromethoxy)phenyl)urea | 2214 (CPTU) |

TABLE 2-continued sEH inhibitors

| Structure | Name | sEHi # |
|---|---|---|
| 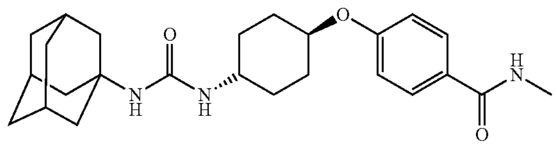 | trans-N-methyl-4-[4-(3-Adamantan-1-yl-ureido)-cyclohexyloxy]-benzamide | 2225 (tMAUCB) |
| 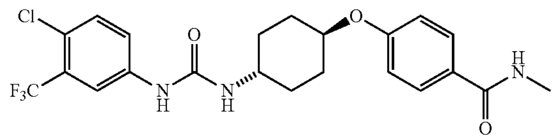 | trans-N-methyl- 4-[4-((3-trifluoromethyl-4-chlorophenyl)-ureido)-cyclohexyloxy]-benzamide | 2226 (tMTCUCB) |
| 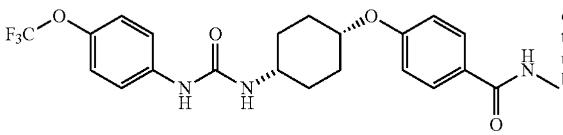 | cis-N-methyl-4-{4-[3-(4-trifluoromethoxy-phenyl)-ureido]-cyclohexyloxy}-benzamide | 2228 (cMTUCB) |
| 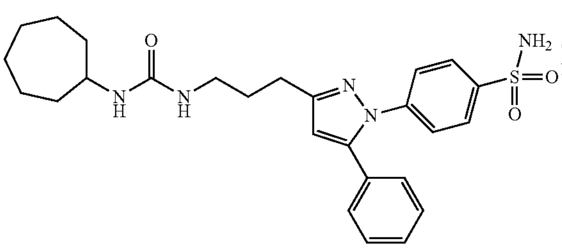 [SMILES: NS(=O)(=O)c1ccc(-n2nc(CCCNC(=O)NC3CCCCCC3)cc2-c2ccccc2)cc1] | 1-cycloheptyl-3-(3-(1,5-diphenyl-1H-pyrazol-3-yl)propyl)urea | 2247 (HDP3U) |

A number of other sEH inhibitors which can be used in the methods and compositions are set forth in co-owned applications PCT/US2013/024396, PCT/US2012/025074, PCT/US2011/064474, PCT/US2011/022901, PCT/US2008/072199, PCT/US2007/006412, PCT/US2005/038282, PCT/US2005/08765, PCT/US2004/010298 and U.S. Published Patent Application Publication Nos: 2014/0088156, 2014/0038923, 2013/0274476, 2013/0143925, 2013/0137726, 2011/0098322, 2005/0026844, each of which is hereby incorporated herein by reference in its entirety for all purposes.

U.S. Pat. No. 5,955,496 (the '496 patent) also sets forth a number of sEH inhibitors which can be used in the methods. One category of these inhibitors comprises inhibitors that mimic the substrate for the enzyme. The lipid alkoxides (e.g., the 9-methoxide of stearic acid) are an exemplar of this group of inhibitors. In addition to the inhibitors discussed in the '496 patent, a dozen or more lipid alkoxides have been tested as sEH inhibitors, including the methyl, ethyl, and propyl alkoxides of oleic acid (also known as stearic acid alkoxides), linoleic acid, and arachidonic acid, and all have been found to act as inhibitors of sEH.

In another group of embodiments, the '496 patent sets forth sEH inhibitors that provide alternate substrates for the enzyme that are turned over slowly. Exemplars of this category of inhibitors are phenyl glycidols (e.g., S, S-4-nitrophenylglycidol), and chalcone oxides. The '496 patent notes that suitable chalcone oxides include 4-phenylchalcone oxide and 4-fluourochalcone oxide. The phenyl glycidols and chalcone oxides are believed to form stable acyl enzymes.

Additional inhibitors of sEH suitable for use in the methods are set forth in U.S. Pat. No. 6,150,415 (the '415 patent) and U.S. Pat. No. 6,531,506 (the '506 patent). Two preferred classes of sEH inhibitors are compounds of Formulas 1 and 2, as described in the '415 and '506 patents. Means for preparing such compounds and assaying desired compounds for the ability to inhibit epoxide hydrolases are also described. The '506 patent, in particular, teaches scores of inhibitors of Formula 1 and some twenty sEH inhibitors of Formula 2, which were shown to inhibit human sEH at concentrations as low as 0.1 µM. Any particular sEH inhibitor can readily be tested to determine whether it will work in the methods by standard assays. Esters and salts of the various compounds discussed above or in the cited patents, for example, can be readily tested by these assays for their use in the methods.

As noted above, chalcone oxides can serve as an alternate substrate for the enzyme. While chalcone oxides have half-lives which depend in part on the particular structure, as a group the chalcone oxides tend to have relatively short half-lives (a drug's half-life is usually defined as the time for the concentration of the drug to drop to half its original value. See, e.g., Thomas, G., Medicinal Chemistry: an introduction, John Wiley & Sons Ltd. (West Sussex, England, 2000)). Since the various uses contemplate inhibition of sEH over differing periods of time which can be measured in days, weeks, or months, chalcone oxides, and other inhibitors which have a half-life whose duration is shorter than the practitioner deems desirable, are preferably administered in a manner which provides the agent over a period of time. For example, the inhibitor can be provided in materials that release the inhibitor slowly. Methods of administration that permit high local concentrations of an inhibitor over a period of time are known, and are not limited to use with inhibitors which have short half-lives although, for inhibitors with a relatively short half-life, they are a preferred method of administration.

In addition to the compounds in Formula 1 of the '506 patent, which interact with the enzyme in a reversible fashion based on the inhibitor mimicking an enzyme-substrate transition state or reaction intermediate, one can have compounds that are irreversible inhibitors of the enzyme. The active structures such as those in the Tables or Formula 1 of the '506 patent can direct the inhibitor to the enzyme where a reactive functionality in the enzyme catalytic site can form a covalent bond with the inhibitor. One group of molecules which could interact like this would have a leaving group such as a halogen or tosylate which could be attacked in an SN2 manner with a lysine or histidine. Alternatively, the reactive functionality could be an epoxide or Michael acceptor such as an α/β-unsaturated ester, aldehyde, ketone, ester, or nitrile.

Further, in addition to the Formula 1 compounds, active derivatives can be designed for practicing the invention. For example, dicyclohexyl thio urea can be oxidized to dicyclohexylcarbodiimide which, with enzyme or aqueous acid (physiological saline), will form an active dicyclohexylurea. Alternatively, the acidic protons on carbamates or ureas can be replaced with a variety of substituents which, upon oxidation, hydrolysis or attack by a nucleophile such as glutathione, will yield the corresponding parent structure. These materials are known as prodrugs or protoxins (Gilman et al., The Pharmacological Basis of Therapeutics, 7th Edition, MacMillan Publishing Company, New York, p. 16 (1985)) Esters, for example, are common prodrugs which are released to give the corresponding alcohols and acids enzymatically (Yoshigae et al., Chirality, 9:661-666 (1997)). The drugs and prodrugs can be chiral for greater specificity. These derivatives have been extensively used in medicinal and agricultural chemistry to alter the pharmacological properties of the compounds such as enhancing water solubility, improving formulation chemistry, altering tissue targeting, altering volume of distribution, and altering penetration. They also have been used to alter toxicology profiles.

There are many prodrugs possible, but replacement of one or both of the two active hydrogens in the ureas described here or the single active hydrogen present in carbamates is particularly attractive. Such derivatives have been extensively described by Fukuto and associates. These derivatives have been extensively described and are commonly used in agricultural and medicinal chemistry to alter the pharmacological properties of the compounds. (Black et al., Journal of Agricultural and Food Chemistry, 21(5):747-751 (1973); Fahmy et al, Journal of Agricultural and Food Chemistry, 26(3):550-556 (1978); Jojima et al., Journal of Agricultural and Food Chemistry, 31(3):613-620 (1983); and Fahmy et al., Journal of Agricultural and Food Chemistry, 29(3):567-572 (1981).)

Such active proinhibitor derivatives are within the scope of the present invention, and the just-cited references are incorporated herein by reference. Without being bound by theory, it is believed that suitable inhibitors mimic the enzyme transition state so that there is a stable interaction with the enzyme catalytic site. The inhibitors appear to form hydrogen bonds with the nucleophilic carboxylic acid and a polarizing tyrosine of the catalytic site.

In some embodiments, the sEH inhibitor used in the methods taught herein is a "soft drug." Soft drugs are compounds of biological activity that are rapidly inactivated by enzymes as they move from a chosen target site. EETs and simple biodegradable derivatives administered to an area of interest may be considered to be soft drugs in that they are likely to be enzymatically degraded by sEH as they diffuse away from the site of interest following administration. Some sEHI, however, may diffuse or be transported following administration to regions where their activity in inhibiting sEH may not be desired. Thus, multiple soft drugs for treatment have been prepared. These include but are not limited to carbamates, esters, carbonates and amides placed in the sEHI, approximately 7.5 angstroms from the carbonyl of the central pharmacophore. These are highly active sEHI that yield biologically inactive metabolites by the action of esterase and/or amidase. Groups such as amides and carbamates on the central pharmacophores can also be used to increase solubility for applications in which that is desirable in forming a soft drug. Similarly, easily metabolized ethers may contribute soft drug properties and also increase the solubility.

In some embodiments, sEH inhibition can include the reduction of the amount of sEH. As used herein, therefore, sEH inhibitors can therefore encompass nucleic acids that inhibit expression of a gene encoding sEH. Many methods of reducing the expression of genes, such as reduction of transcription and siRNA, are known, and are discussed in more detail below.

In various embodiments, a compound with combined functionality to concurrently inhibit sEH and COX-2 is administered. Urea-containing pyrazoles that function as dual inhibitors of cyclooxygenase-2 and soluble epoxide hydrolase are described, e.g., in Hwang, et al., *J Med Chem.* (2011) 28; 54(8):3037-50.

Preferably, the inhibitor inhibits sEH without also significantly inhibiting microsomal epoxide hydrolase ("mEH"). Preferably, at concentrations of 100 μM, the inhibitor inhibits sEH activity by at least 50% while not inhibiting mEH activity by more than 10%. Preferred compounds have an $IC_{50}$ (inhibition potency or, by definition, the concentration of inhibitor which reduces enzyme activity by 50%) of less than about 100 μM. Inhibitors with $IC_{50}$s of less than 100 μM are preferred, with $IC_{50}$s of less than 75 μM being more preferred and, in order of increasing preference, an $IC_{50}$ of 50 μM, 40 μM, 30 μM, 25 μM, 20 μM, 15 μM, 10 μM, 5 μM, 3 μM, 2 μM, 1 μM, 100 nM, 10 nM, 1.0 nM, or even less, being still more preferred. Assays for determining sEH activity are known in the art and described elsewhere herein. The $IC_{50}$ determination of the inhibitor can be made with respect to an sEH enzyme from the species subject to treatment (e.g., the subject receiving the inhibitor of sEH).

b. Cis-Epoxyeicosantrienoic Acids ("EETs")

EETs, which are epoxides of arachidonic acid, are known to be effectors of blood pressure, regulators of inflammation, and modulators of vascular permeability. Hydrolysis of the epoxides by sEH diminishes this activity. Inhibition of sEH raises the level of EETs since the rate at which the EETs are hydrolyzed into dihydroxyeicosatrienoic acids ("DHETs") is reduced.

It has long been believed that EETs administered systemically would be hydrolyzed too quickly by endogenous sEH to be helpful. For example, in one prior report of EETs administration, EETs were administered by catheters inserted into mouse aortas. The EETs were infused continuously during the course of the experiment because of concerns over the short half-life of the EETs. See, Liao and Zeldin, International Publication WO 01/10438 (hereafter "Liao and Zeldin"). It also was not known whether endogenous sEH could be inhibited sufficiently in body tissues to permit administration of exogenous EET to result in increased levels of EETs over those normally present. Further, it was thought that EETs, as epoxides, would be too labile to survive the storage and handling necessary for therapeutic use.

Studies from the laboratory of the present inventors, however, showed that systemic administration of EETs in conjunction with inhibitors of sEH had better results than did administration of sEH inhibitors alone. EETs were not administered by themselves in these studies since it was anticipated they would be degraded too quickly to have a useful effect. Additional studies from the laboratory of the present inventors have since shown, however, that administration of EETs by themselves has had therapeutic effect. Without wishing to be bound by theory, it is surmised that the exogenous EET overwhelms endogenous sEH, and allows EETs levels to be increased for a sufficient period of time to have therapeutic effect. Thus, EETs can be administered without also administering an sEHI to provide a therapeutic effect. Moreover, EETs, if not exposed to acidic conditions or to sEH are stable and can withstand reasonable storage, handling and administration.

In short, sEHI, EETs, or co-administration of sEHIs and of EETs, can be used in the methods of the present invention. In some embodiments, one or more EETs are administered to the patient without also administering an sEHI. In some embodiments, one or more EETs are administered shortly before or concurrently with administration of an sEH inhibitor to slow hydrolysis of the EET or EETs. In some embodiments, one or more EETs are administered after administration of an sEH inhibitor, but before the level of the sEHI has diminished below a level effective to slow the hydrolysis of the EETs.

EETs useful in the methods of the present invention include 14,15-EET, 8,9-EET and 11,12-EET, and 5,6 EETs. Preferably, the EETs are administered as the methyl ester, which is more stable. Persons of skill will recognize that the EETs are regioisomers, such as 8S,9R- and 14R,15S-EET. 8,9-EET, 11,12-EET, and 14R,15S-EET, are commercially available from, for example, Sigma-Aldrich (catalog nos. E5516, E5641, and E5766, respectively, Sigma-Aldrich Corp., St. Louis, Mo.).

If desired, EETs, analogs, or derivatives that retain activity can be used in place of or in combination with unmodified EETs. Liao and Zeldin, supra, define EET analogs as compounds with structural substitutions or alterations in an EET, and include structural analogs in which one or more EET olefins are removed or replaced with acetylene or cyclopropane groups, analogs in which the epoxide moiety is replaced with oxitane or furan rings and heteroatom analogs. In other analogs, the epoxide moiety is replaced with ether, alkoxides, urea, amide, carbamate, difluorocyclopropane, or carbonyl, while in others, the carboxylic acid moiety is stabilized by blocking beta oxidation or is replaced with a commonly used mimic, such as a nitrogen heterocycle, a sulfonamide, or another polar functionality. In preferred forms, the analogs or derivatives are relatively stable as compared to an unmodified EET because they are more resistant than an unmodified EET to sEH and to chemical breakdown. "Relatively stable" means the rate of hydrolysis by sEH is at least 25% less than the hydrolysis of the unmodified EET in a hydrolysis assay, and more preferably 50% or more lower than the rate of hydrolysis of an unmodified EET. Liao and Zeldin show, for example, episulfide and sulfonamide EETs derivatives. Amide and ester derivatives of EETs and that are relatively stable are preferred embodiments. Whether or not a particular EET analog or derivative has the biological activity of the unmodified EET can be readily determined by using it in standard assays, such as radio-ligand competition assays to measure binding to the relevant receptor. As mentioned in the Definition section, above, for convenience of reference, the term "EETs" as used herein refers to unmodified EETs, and EETs analogs and derivatives unless otherwise required by context.

In some embodiments, the EET or EETs are embedded or otherwise placed in a material that releases the EET over time. Materials suitable for promoting the slow release of compositions such as EETs are known in the art. Optionally, one or more sEH inhibitors may also be placed in the slow release material.

Conveniently, the EET or EETs can be administered orally. Since EETs are subject to degradation under acidic conditions, EETs intended for oral administration can be coated with a coating resistant to dissolving under acidic conditions, but which dissolve under the mildly basic conditions present in the intestines. Suitable coatings, commonly known as "enteric coatings" are widely used for products, such as aspirin, which cause gastric distress or which would undergo degradation upon exposure to gastric acid. By using coatings with an appropriate dissolution profile, the coated substance can be released in a chosen section of the intestinal tract. For example, a substance to be released in the colon is coated with a substance that dissolves at pH 6.5-7, while substances to be released in the duodenum can be coated with a coating that dissolves at pH values over 5.5. Such coatings are commercially available from, for example, Rohm Specialty Acrylics (Rohm America LLC, Piscataway, N.J.) under the trade name "Eudragit®". The choice of the particular enteric coating is not critical to the practice.

c. Phosphodiesterase Inhibitors (PDEi)

Phosphodiesterase inhibitors (PDEi) are well known anti-inflammatory agents. Many different classes of isozyme selective PDEi lead to remarkable increases in the plasma levels of a broad range of epoxy-fatty acids (EFA). The magnitude of this increase is so dramatic that PDEi can elevate epoxy-fatty acids as well as highly potent inhibitors of soluble epoxide hydrolase. Accordingly, levels of epoxygenated fatty acids (e.g., in blood, plasma, serum) can be increased by administration of a phosphodiesterase inhibitor (PDEi).

The PDEi may or may not be selective, specific or preferential for cAMP. Exemplary PDEs that degrade cAMP include without limitation PDE3, PDE4, PDE7, PDE8 and PDE10. Exemplary cAMP selective hydrolases include PDE4, 7 and 8. Exemplary PDEs that hydrolyse both cAMP and cGMP include PDE1, PDE2, PDE3, PDE10 and PDE11. Isoenzymes and isoforms of PDEs are well known in the art. See, e.g., Boswell-Smith et al., Brit. J. Pharmacol. 147: S252-257 (2006), and Reneerkens, et al., Psychopharmacology (2009) 202:419-443, the contents of which are incorporated herein by reference.

In some embodiments, the PDE inhibitor is a non-selective inhibitor of PDE. Exemplary non-selective PDE inhibitors that find use include without limitation caffeine, theophylline, isobutylmethylxanthine, aminophylline, pentoxifylline, vasoactive intestinal peptide (VIP), secretin, adrenocorticotropic hormone, pilocarpine, alpha-melanocyte stimulating hormone (MSH), beta-MSH, gamma-MSH, the ionophore A23187, prostaglandin E1.

In some embodiments, the PDE inhibitor used specifically or preferentially inhibits PDE4. Exemplary inhibitors that selectively inhibit PDE4 include without limitation rolipram, roflumilast, cilomilast, ariflo, HT0712, ibudilast and mesembrine.

In some embodiments, the PDE inhibitor used specifically or preferentially inhibits a cAMP PDE, e.g., PDE4, PDE7 or PDE8. In some embodiments, the PDE inhibitor used inhibits a cAMP PDE, e.g., PDE1, PDE2, PDE3, PDE4, PDE7, PDE8, PDE10 or PDE11. Exemplary agents that inhibit a cAMP phosphodiesterase include without limitation rolipram, roflumilast, cilomilast, ariflo, HT0712, ibudilast, mesembrine, cilostamide, enoxamone, milrinone, siguazodan and BRL-50481.

In some embodiments, the PDE inhibitor used specifically inhibits PDE5. Exemplary inhibitors that selectively inhibit PDE5 include without limitation sildenafil, zaprinast, tadalafil, udenafil, avanafil and vardenafil.

d. Assays for Epoxide Hydrolase Activity

Any of a number of standard assays for determining epoxide hydrolase activity can be used to determine inhibition of sEH. For example, suitable assays are described in Gill, et al., Anal Biochem 131:273-282 (1983); and Borhan, et al., Analytical Biochemistry 231:188-200 (1995)). Suitable in vitro assays are described in Zeldin et al., J Biol. Chem. 268:6402-6407 (1993). Suitable in vivo assays are described in Zeldin et al., Arch Biochem Biophys 330:87-96 (1996). Assays for epoxide hydrolase using both putative natural substrates and surrogate substrates have been reviewed (see, Hammock, et al. In: Methods in Enzymology, Volume III, Steroids and Isoprenoids, Part B, (Law, J. H. and H. C. Rilling, eds. 1985), Academic Press, Orlando, Fla., pp. 303-311 and Wixtrom et al., In: Biochemical Pharmacology and Toxicology, Vol. 1: Methodological Aspects of Drug Metabolizing Enzymes, (Zakim, D. and D. A. Vessey, eds. 1985), John Wiley & Sons, Inc., New York, pp. 1-93. Several spectral based assays exist based on the reactivity or tendency of the resulting diol product to hydrogen bond (see, e.g., Wixtrom, supra, and Hammock. Anal. Biochem. 174: 291-299 (1985) and Dietze, et al. Anal. Biochem. 216:176-187 (1994)).

The enzyme also can be detected based on the binding of specific ligands to the catalytic site which either immobilize the enzyme or label it with a probe such as dansyl, fluoracein, luciferase, green fluorescent protein or other reagent. The enzyme can be assayed by its hydration of EETs, its hydrolysis of an epoxide to give a colored product as described by Dietze et al., 1994, supra, or its hydrolysis of a radioactive surrogate substrate (Borhan et al., 1995, supra). The enzyme also can be detected based on the generation of fluorescent products following the hydrolysis of the epoxide. Numerous methods of epoxide hydrolase detection have been described (see, e.g., Wixtrom, supra).

The assays are normally carried out with a recombinant enzyme following affinity purification. They can be carried out in crude tissue homogenates, cell culture or even in vivo, as known in the art and described in the references cited above.

e. Other Means of Inhibiting sEH Activity

Other means of inhibiting sEH activity or gene expression can also be used in the methods. For example, a nucleic acid molecule complementary to at least a portion of the human sEH gene can be used to inhibit sEH gene expression. Means for inhibiting gene expression using short RNA molecules, for example, are known. Among these are short interfering RNA (siRNA), small temporal RNAs (stRNAs), and microRNAs (miRNAs). Short interfering RNAs silence genes through a mRNA degradation pathway, while stRNAs and miRNAs are approximately 21 or 22 nt RNAs that are processed from endogenously encoded hairpin-structured precursors, and function to silence genes via translational repression. See, e.g., McManus et al., RNA, 8(6):842-50 (2002); Morris et al., Science, 305(5688):1289-92 (2004); He and Hannon, Nat Rev Genet. 5(7):522-31 (2004).

"RNA interference," a form of post-transcriptional gene silencing ("PTGS"), describes effects that result from the introduction of double-stranded RNA into cells (reviewed in Fire, A. Trends Genet 15:358-363 (1999); Sharp, P. Genes Dev 13:139-141 (1999); Hunter, C. Curr Biol 9:R440-R442 (1999); Baulcombe. D. Curr Biol 9:R599-R601 (1999); Vaucheret et al. Plant J 16: 651-659 (1998)). RNA interference, commonly referred to as RNAi, offers a way of specifically inactivating a cloned gene, and is a powerful tool for investigating gene function.

The active agent in RNAi is a long double-stranded (antiparallel duplex) RNA, with one of the strands corresponding or complementary to the RNA which is to be inhibited. The inhibited RNA is the target RNA. The long double stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo.

In mammalian cells other than these, however, longer RNA duplexes provoked a response known as "sequence non-specific RNA interference," characterized by the non-specific inhibition of protein synthesis.

Further studies showed this effect to be induced by dsRNA of greater than about 30 base pairs, apparently due to an interferon response. It is thought that dsRNA of greater than about 30 base pairs binds and activates the protein PKR and 2',5'-oligonucleotide synthetase (2',5'-AS). Activated PKR stalls translation by phosphorylation of the translation initiation factors eIF2α, and activated 2',5'-AS causes mRNA degradation by 2',5'-oligonucleotide-activated ribonuclease L. These responses are intrinsically sequence-nonspecific to the inducing dsRNA; they also frequently result in apoptosis, or cell death. Thus, most somatic mammalian cells undergo apoptosis when exposed to the concentrations of dsRNA that induce RNAi in lower eukaryotic cells.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. Nature 411: 494-498 (2001)). In this report, siRNA were applied to cultured cells by transfection in oligofectamine micelles. These RNA duplexes were too short to elicit sequence-nonspecific responses like apoptosis, yet they efficiently initiated RNAi. Many laboratories then tested the use of siRNA to knock out target genes in mammalian cells. The results demonstrated that siRNA works quite well in most instances.

For purposes of reducing the activity of sEH, siRNAs to the gene encoding sEH can be specifically designed using computer programs. The cloning, sequence, and accession numbers of the human sEH sequence are set forth in Beetham et al., Arch. Biochem. Biophys. 305(1):197-201 (1993). An exemplary amino acid sequence of human sEH (GenBank Accession No. L05779; SEQ ID NO:1) and an exemplary nucleotide sequence encoding that amino acid sequence (GenBank Accession No. AAA02756; SEQ ID NO:2) are set forth in U.S. Pat. No. 5,445,956. The nucleic acid sequence of human sEH is also published as GenBank Accession No. NM_001979.4; the amino acid sequence of human sEH is also published as GenBank Accession No. NP_001970.2.

A program, siDESIGN from Dharmacon, Inc. (Lafayette, Colo.), permits predicting siRNAs for any nucleic acid sequence, and is available on the World Wide Web at dharmacon.com. Programs for designing siRNAs are also available from others, including Genscript (available on the Web at genscript.com/ssl-bin/app/rnai) and, to academic and non-profit researchers, from the Whitehead Institute for Biomedical Research found on the worldwide web at "jura.wi.mit.edu/pubint/http://iona.wi.mit.edu/siRNAext/."

For example, using the program available from the Whitehead Institute, the following sEH target sequences and siRNA sequences can be generated:

1) Target:
(SEQ ID NO: 3)
CAGTGTTCATTGGCCATGACTGG

Sense-siRNA:
(SEQ ID NO: 4)
5'-GUGUUCAUUGGCCAUGACUTT-3'

Antisense-siRNA:
(SEQ ID NO: 5)
5'-AGUCAUGGCCAAUGAACACTT-3'

2) Target:
(SEQ ID NO: 6)
GAAAGGCTATGGAGAGTCATCTG

Sense-siRNA:
(SEQ ID NO: 7)
5'-AAGGCUAUGGAGAGUCAUCTT-3'

Antisense-siRNA:
(SEQ ID NO: 8)
5'-GAUGACUCUCCAUAGCCUUTT-3'

3) Target:
(SEQ ID NO: 9)
AAAGGCTATGGAGAGTCATCTGC

Sense-siRNA:
(SEQ ID NO: 10)
5'-AGGCUAUGGAGAGUCAUCUTT-3'

Antisense-siRNA:
(SEQ ID NO: 11)
5'-AGAUGACUCUCCAUAGCCUTT-3'

4) Target:
(SEQ ID NO: 12)
CAAGCAGTGTTCATTGGCCATGA

Sense-siRNA:
(SEQ ID NO: 13)
5'-AGCAGUGUUCAUUGGCCAUTT-3'

Antisense-siRNA:
(SEQ ID NO: 14)
5'-AUGGCCAAUGAACACUGCUTT-3'

5) Target:
(SEQ ID NO: 15)
CAGCACATGGAGGACTGGATTCC

Sense-siRNA:
(SEQ ID NO: 16)
5'-GCACAUGGAGGACUGGAUUTT-3'

Antisense-siRNA:
(SEQ ID NO: 17)
5'-AAUCCAGUCCUCCAUGUGCTT-3'

Alternatively, siRNA can be generated using kits which generate siRNA from the gene. For example, the "Dicer siRNA Generation" kit (catalog number T510001, Gene Therapy Systems, Inc., San Diego, Calif.) uses the recombinant human enzyme "dicer" in vitro to cleave long double stranded RNA into 22 bp siRNAs. By having a mixture of siRNAs, the kit permits a high degree of success in generating siRNAs that will reduce expression of the target gene. Similarly, the Silencer™ siRNA Cocktail Kit (RNase III) (catalog no. 1625, Ambion, Inc., Austin, Tex.) generates a mixture of siRNAs from dsRNA using RNase III instead of dicer. Like dicer, RNase III cleaves dsRNA into 12-30 bp dsRNA fragments with 2 to 3 nucleotide 3' overhangs, and 5'-phosphate and 3'-hydroxyl termini. According to the manufacturer, dsRNA is produced using T7 RNA polymerase, and reaction and purification components included in the kit. The dsRNA is then digested by RNase III to create a population of siRNAs. The kit includes reagents to synthesize long dsRNAs by in vitro transcription and to digest those dsRNAs into siRNA-like molecules using RNase III. The manufacturer indicates that the user need only supply a DNA template with opposing T7 phage polymerase promoters or two separate templates with promoters on opposite ends of the region to be transcribed.

The siRNAs can also be expressed from vectors. Typically, such vectors are administered in conjunction with a second vector encoding the corresponding complementary strand. Once expressed, the two strands anneal to each other and form the functional double stranded siRNA. One exemplar vector suitable for use in the invention is pSuper, available from OligoEngine, Inc. (Seattle, Wash.). In some embodiments, the vector contains two promoters, one positioned downstream of the first and in antiparallel orientation. The first promoter is transcribed in one direction, and the second in the direction antiparallel to the first, resulting in expression of the complementary strands. In yet another set of embodiments, the promoter is followed by a first segment encoding the first strand, and a second segment encoding the second strand. The second strand is complementary to the palindrome of the first strand. Between the first and the second strands is a section of RNA serving as a linker (sometimes called a "spacer") to permit the second strand to bend around and anneal to the first strand, in a configuration known as a "hairpin."

The formation of hairpin RNAs, including use of linker sections, is well known in the art. Typically, an siRNA expression cassette is employed, using a Polymerase III promoter such as human U6, mouse U6, or human H1. The coding sequence is typically a 19-nucleotide sense siRNA sequence linked to its reverse complementary antisense siRNA sequence by a short spacer. Nine-nucleotide spacers are typical, although other spacers can be designed. For example, the Ambion website indicates that its scientists have had success with the spacer TTCAAGAGA (SEQ ID NO:18). Further, 5-6 T's are often added to the 3' end of the oligonucleotide to serve as a termination site for Polymerase III. See also, Yu et al., Mol Ther 7(2):228-36 (2003); Matsukura et al., Nucleic Acids Res 31(15):e77 (2003).

As an example, the siRNA targets identified above can be targeted by hairpin siRNA as follows. To attack the same targets by short hairpin RNAs, produced by a vector (permanent RNAi effect), sense and antisense strand can be put in a row with a loop forming sequence in between and suitable sequences for an adequate expression vector to both ends of the sequence. The following are non-limiting examples of hairpin sequences that can be cloned into the pSuper vector:

1) Target:
(SEQ ID NO: 19)
CAGTGTTCATTGGCCATGACTGG

Sense strand:
(SEQ ID NO: 20)
5'-GATCCCCGTGTTCATTGGCCATGACTTTCAAGAGAAGTCATGGCCAAT
GAACACTTTTT-3'

Antisense strand:
(SEQ ID NO: 21)
5'-AGCTAAAAAGTGTTCATTGGCCATGACTTCTCTTGAAAGTCATGGCCA
ATGAACACGGG-3'

2) Target:
(SEQ ID NO: 22)
GAAAGGCTATGGAGAGTCATCTG

Sense strand:
(SEQ ID NO: 23)
5'-GATCCCCAAGGCTATGGAGAGTCATCTTCAAGAGAGATGACTCTCCAT
AGCCTTTTTT-3'

Antisense strand:
(SEQ ID NO: 24)
5'-AGCTAAAAAAGGCTATGGAGAGTCATCTCTCTTGAAGATGACTCTCC
ATAGCCTTGGG-3'

3) Target:
(SEQ ID NO: 25)
AAAGGCTATGGAGAGTCATCTGC

Sense strand:
(SEQ ID NO: 26)
5'-GATCCCCAGGCTATGGAGAGTCATCTTTCAAGAGAAGATGACTCTCCA
TAGCCTTTTT-3'

Antisense strand:
(SEQ ID NO: 27)
5'-AGCTAAAAAAGGCTATGGAGAGTCATCATCTCTTGAAAGATGACTCTC
CATAGCCTGGG-3'

4) Target:
(SEQ ID NO: 28)
CAAGCAGTGTTCATTGGCCATGA

Sense strand:
(SEQ ID NO: 29)
5'-GATCCCCAGCAGTGTTCATTGGCCATTTCAAGAGAATGGCCAATGAAC
ACTGCTTTTT-3'

Antisense strand:
(SEQ ID NO: 30)
5'-AGCTAAAAAAGCAGTGTTCATTGGCCATTCTCTTGAAATGGCCAATGA
ACACTGCTGGG-3'

5) Target:
(SEQ ID NO: 31)
CAGCACATGGAGGACTGGATTCC

Sense strand
(SEQ ID NO: 32)
5'-GATCCCCGCACATGGAGGACTGGATTTTCAAGAGAAATCCAGTCCTCC
ATGTGCTTTTT-3'

Antisense strand:
(SEQ ID NO: 33)
5'-AGCTAAAAAAGCACATGGAGGACTGGATTTCTCTTGAAAATCCAGTCCT
CCATGTGCGGG-3'

In addition to siRNAs, other means are known in the art for inhibiting the expression of antisense molecules, ribozymes, and the like are well known to those of skill in the art. The nucleic acid molecule can be a DNA probe, a riboprobe, a peptide nucleic acid probe, a phosphorothioate probe, or a 2'-O methyl probe.

Generally, to assure specific hybridization, the antisense sequence is substantially complementary to the target sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to the sEH gene is retained as a functional property of the polynucleotide. In one embodiment, the antisense molecules form a triple helix-containing, or "triplex" nucleic acid. Triple helix formation results in inhibition of gene expression by, for example, preventing transcription of the target gene (see, e.g., Cheng et al., 1988, J. Biol. Chem. 263:15110; Ferrin and Camerini-Otero, 1991, Science 354:1494; Ramdas et al., 1989, J. Biol. Chem. 264:17395; Strobel et al., 1991, Science 254:1639; and Rigas et al., 1986, Proc. Natl. Acad. Sci. U.S.A. 83:9591)

Antisense molecules can be designed by methods known in the art. For example, Integrated DNA Technologies (Coralville, Iowa) makes available a program found on the worldwide web "biotools.idtdna.com/antisense/Anti-Sense.aspx", which will provide appropriate antisense sequences for nucleic acid sequences up to 10,000 nucleotides in length. Using this program with the sEH gene provides the following exemplar sequences:

1)
(SEQ ID NO: 34)
UGUCCAGUGCCCACAGUCCU 2)
(SEQ ID NO: 35)
UUCCCACCUGACACGACUCU 3)
(SEQ ID NO: 36)
GUUCAGCCUCAGCCACUCCU 4)
(SEQ ID NO: 37)
AGUCCUCCCGCUUCACAGA 5)
(SEQ ID NO: 38)
GCCCACUUCCAGUUCCUUUCC

In another embodiment, ribozymes can be designed to cleave the mRNA at a desired position. (See, e.g., Cech, 1995, Biotechnology 13:323; and Edgington, 1992, Biotechnology 10:256 and Hu et al., PCT Publication WO 94/03596).

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules may be prepared by de novo chemical synthesis or by cloning. For example, an antisense RNA can be made by inserting (ligating) a sEH gene sequence in reverse orientation operably linked to a promoter in a vector (e.g., plasmid). Provided that the promoter and, preferably termination and polyadenylation signals, are properly positioned, the strand of the inserted sequence corresponding to the noncoding strand are transcribed and act as an antisense oligonucleotide.

It are appreciated that the oligonucleotides can be made using nonstandard bases (e.g., other than adenine, cytidine, guanine, thymine, and uridine) or nonstandard backbone structures to provides desirable properties (e.g., increased nuclease-resistance, tighter-binding, stability or a desired Tm). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al., 1991, Science 254:1497) or incorporating 2'-O-methyl ribonucleotides, phosphorothioate nucleotides, methyl phosphonate nucleotides, phosphotriester nucleotides, phosphorothioate nucleotides, phosphoramidates.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996). Another subsequence, the h (hydrophobic) domain of signal peptides, was found to have similar cell membrane translocation characteristics (see, e.g., Lin et al., J. Biol. Chem. 270:14255-14258 (1995)). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

More recently, it has been discovered that siRNAs can be introduced into mammals without eliciting an immune response by encapsulating them in nanoparticles of cyclodextrin. Information on this method can be found on the worldwide web at "nature.com/news/2005/050418/full/050418-6.html."

In another method, the nucleic acid is introduced directly into superficial layers of the skin or into muscle cells by a jet of compressed gas or the like. Methods for administering naked polynucleotides are well known and are taught, for example, in U.S. Pat. No. 5,830,877 and International Publication Nos. WO 99/52483 and WO 94/21797. Devices for accelerating particles into body tissues using compressed gases are described in, for example, U.S. Pat. Nos. 6,592,545, 6,475,181, and 6,328,714. The nucleic acid may be lyophilized and may be complexed, for example, with polysaccharides to form a particle of appropriate size and mass for acceleration into tissue. Conveniently, the nucleic acid can be placed on a gold bead or other particle which provides suitable mass or other characteristics. Use of gold beads to carry nucleic acids into body tissues is taught in, for example, U.S. Pat. Nos. 4,945,050 and 6,194,389.

The nucleic acid can also be introduced into the body in a virus modified to serve as a vehicle without causing pathogenicity. The virus can be, for example, adenovirus, fowlpox virus or vaccinia virus.

miRNAs and siRNAs differ in several ways: miRNA derive from points in the genome different from previously recognized genes, while siRNAs derive from mRNA, viruses or transposons, miRNA derives from hairpin structures, while siRNA derives from longer duplexed RNA, miRNA is conserved among related organisms, while siRNA usually is not, and miRNA silences loci other than that from which it derives, while siRNA silences the loci from which it arises. Interestingly, miRNAs tend not to exhibit perfect complementarity to the mRNA whose expression they inhibit. See, McManus et al., supra. See also, Cheng et al., Nucleic Acids Res. 33(4):1290-7 (2005); Robins and Padgett, Proc Natl Acad Sci USA. 102(11): 4006-9 (2005); Brennecke et al., PLoS Biol. 3(3):e85 (2005). Methods of designing miRNAs are known. See, e.g., Zeng et al., Methods Enzymol. 392:371-80 (2005); Krol et al., J Biol Chem. 279(40):42230-9 (2004); Ying and Lin, Biochem Biophys Res Commun. 326(3):515-20 (2005).

In some embodiments, the endogenous polynucleotide encoding sEH in the subject can be rendered non-functional or non-expressing, e.g., by employing gene therapy methodologies. This can be accomplished using any method known in the art, including the working embodiment described herein. In varying embodiments, the endogenous gene encoding sEH in the subject is rendered non-functional or non-expressing in certain desired tissues, e.g., to bone tissues, as demonstrated herein. In varying embodiments, the endogenous gene encoding sEH in the subject is rendered non-functional or non-expressing by employing homologous recombination, mutating, replacing or eliminating the functional or expressing gene encoding sEH. Illustrative methods are known in the art and described, e.g., in Flynn, et al., *Exp Hematol*. (2015) Jun. 19. pii: 50301-472X (15)00207-6 (using CRISPR); Truong, et al, *Nucleic Acids Res*. (2015) Jun. 16. pii: gkv601 (using split-Cas9); Yang, *Mil Med Res*. (2015) May 9; 2:11 (using CRISPR-Cas9); and Imai, et al., *Intern Med*. (2004) February; 43(2):85-96.

f. Epoxygenated Fatty Acids

In some embodiments, an epoxygenated fatty acid is administered as an agent that increases epoxygenated fatty acids. Illustrative epoxygenated fatty acids include epoxides of linoleic acid, eicosapentaenoic acid ("EPA") and docosahexaenoic acid ("DHA").

The fatty acids eicosapentaenoic acid ("EPA") and docosahexaenoic acid ("DHA") have recently become recognized as having beneficial effects, and fish oil tablets, which are a good source of these fatty acids, are widely sold as supplements. In 2003, it was reported that these fatty acids reduced pain and inflammation. Sethi, S. et al., Blood 100: 1340-1346 (2002). The paper did not identify the mechanism of action, nor the agents responsible for this relief.

Cytochrome P450 ("CYP450") metabolism produces cis-epoxydocosapentaenoic acids ("EpDPEs") and cis-epoxyeicosatetraenoic acids ("EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS- (nitric oxide) and COX-derived (prostacyclin) vasodilators. Overall cytochrome P450 (CYP450) metabolism of polyunsaturated fatty acids produces epoxides, such as EETs, which are prime candidates for the active mediator(s). 14(15)-EpETE, for example, is derived via epoxidation of the 14,15-double bond of EPA and is the ω-3 homolog of 14(15)-EpETrE ("14(15)EET") derived via epoxidation of the 14,15-double bond of arachidonic acid.

As mentioned, it is beneficial to elevate the levels of EETs, which are epoxides of the fatty acid arachidonic acid. Our studies of the effects of EETs has led us to realization that the anti-inflammatory effect of EPA and DHA are likely due to increasing the levels of the epoxides of these two fatty acids. Thus, increasing the levels of epoxides of EPA, of DHA, or of both, will act to reduce pain and inflammation, and symptoms associated with diabetes and metabolic syndromes, in mammals in need thereof. This beneficial effect of the epoxides of these fatty acids has not been previously recognized. Moreover, these epoxides have not previously been administered as agents, in part because, as noted above, epoxides have generally been considered too labile to be administered.

Like EETs, the epoxides of EPA and DHA are substrates for sEH. The epoxides of EPA and DHA are produced in the body at low levels by the action of cytochrome P450s. Endogenous levels of these epoxides can be maintained or increased by the administration of sEHI. However, the endogeous production of these epoxides is low and usually occurs in relatively special circumstances, such as the resolution of inflammation. Our expectation is that administering these epoxides from exogenous sources will aid in the resolution of inflammation and in reducing pain, as well as with symptoms of diabetes and metabolic syndromes. It is further beneficial with pain or inflammation to inhibit sEH with sEHI to reduce hydrolysis of these epoxides, thereby maintaining them at relatively high levels.

EPA has five unsaturated bonds, and thus five positions at which epoxides can be formed, while DHA has six. The epoxides of EPA are typically abbreviated and referred to generically as "EpETEs", while the epoxides of DHA are typically abbreviated and referred to generically as "EpDPEs". The specific regioisomers of the epoxides of each fatty acid are set forth in the following Table 3:

TABLE 3

Regioisomers of Eicosapentaenoic acid ("EPA") epoxides:

1. Formal name: (±)5(6)-epoxy-8Z, 11Z, 14Z, 17Z-eicosatetraenoic acid,
   Synonym 5(6)-epoxy Eicosatetraenoic acid
   Abbreviation 5(6)-EpETE
2. Formal name: (±)8(9)-epoxy-5Z, 11Z, 14Z, 17Z-eicosatetraenoic acid,
   Synonym 8(9)-epoxy Eicosatetraenoic acid
   Abbreviation 8(9)-EpETE
3. Formal name: (±)11(12)-epoxy-5Z, 8Z, 14Z, 17Z-eicosatetraenoic acid,
   Synonym 11(12)-epoxy Eicosatetraenoic acid
   Abbreviation 11(12)-EpETE
4. Formal name: (±)14(15)-epoxy-5Z, 8Z, HZ, 17Z-eicosatetraenoic acid,
   Synonym 14(15)-epoxy Eicosatetraenoic acid
   Abbreviation 14(15)-EpETE
5. Formal name: (±)17(18)-epoxy-5Z, 8Z, 11Z, 14Z-eicosatetraenoic acid,
   Synonym 17(18)-epoxy Eicosatetraenoic acid
   Abbreviation 17(18)-EpETE Regioisomers of Docosahexaenoic acid ("DHA") epoxides:

1. Formal name: (±) 4(5)-epoxy-7Z, 10Z, 13Z, 16Z, 19Z-docosapentaenoic acid,
   Synonym 4(5)-epoxy Docosapentaenoic acid
   Abbreviation 4(5)-EpDPE
2. Formal name: (±) 7(8)-epoxy-4Z, 10Z, 13Z, 16Z, 19Z-docosapentaenoic acid,
   Synonym 7(8)-epoxy Docosapentaenoic acid
   Abbreviation 7(8)-EpDPE
3. Formal name: (±)10(11)-epoxy-4Z, 7Z, 13Z, 16Z, 19Z-docosapentaenoic acid,
   Synonym 10(11)-epoxy Docosapentaenoic acid
   Abbreviation 10(11)-EpDPE TABLE 3-continued 4. Formal name: (±)13(14)-epoxy-4Z, 7Z, 10Z, 16Z, 19Z-docosapentaenoic acid,
   Synonym 13(14)-epoxy Docosapentaenoic acid
   Abbreviation 13(14)-EpDPE
5. Formal name: (±) 16(17)-epoxy-4Z, 7Z, 10Z, 13Z, 19Z-docosapentaenoic acid,
   Synonym 16(17)-epoxy Docosapentaenoic acid
   Abbreviation 16(17)-EpDPE
6. Formal name: (±) 19(20)-epoxy-4Z, 7Z, 10Z, 13Z, 16Z-docosapentaenoic acid,
   Synonym 19(20)-epoxy Docosapentaenoic acid
   Abbreviation 19(20)-EpDPE Any of these epoxides, or combinations of any of these, can be administered in the compositions and methods.

4. Agents that Reduce and/or Inhibit Endoplasmic Reticular (ER) Stress

Methods and compositions described herein involve the co-formulation and/or co-administration of an agent that increases the production and/or level of epoxygenated fatty acids and an inhibitor of endoplasmic reticular (ER) stress. Any agent known in the art to reduce and/or inhibit levels of ER stress can be used. Illustrative agents that reduce and/or inhibit ER stress include without limitation, e.g., 4-phenyl butyric acid ("PBA"), butyrate, 3-phenylpropionic acid (3-PPA), 5-phenylvaleric acid (5-PVA), 6 phenylhexanoic acid (6-PHA), dimethyl-celecoxib (DMCx), tauroursode-oxycholic acid, trehalose, deuterated water, docosahexaenoic acid ("DHA"), eicosapentaenoic acid ("EPA"), vitamin C, arabitol, mannose, glycerol, betaine, sarcosine, trimethylamine-N oxide and DMSO.

5. Formulation and Administration

In various embodiments of the compositions, the agent that increases epoxygenated fatty acids (e.g., an inhibitor of sEH, an EET, an epoxygenated fatty acid, and mixtures thereof) is co-administered with the agent that reduces and/or inhibits ER stress (e.g., PBA). In some embodiments, the agent that increases epoxygenated fatty acids comprises an epoxide of EPA, an epoxide of DHA, or epoxides of both, and an sEHI.

The agent that increases epoxygenated fatty acids and the agent that inhibits and/or reduces ER stress independently can be prepared and administered in a wide variety of oral, parenteral and topical dosage forms. The agent that increases epoxygenated fatty acids and the agent that inhibits and/or reduces ER stress can be administered via the same or different routes of administration. In varying embodiments, the agent that increases epoxygenated fatty acids and the agent that inhibits and/or reduces ER stress independently can be administered orally (e.g., topically, buccally), by injection, that is, intravenously, intramuscularly, intracutaneously, subcutaneously, intraduodenally, or intraperitoneally. The agent that increases epoxygenated fatty acids and the agent that inhibits and/or reduces ER stress can also be administered by inhalation, for example, intranasally. Additionally, the agent that increases epoxygenated fatty acids and the agent that inhibits and/or reduces ER stress can be administered transdermally.

In varying embodiments, one or both of the agent that increases epoxygenated fatty acids (e.g., an sEHI or a pharmaceutically acceptable salt of the inhibitor and, optionally, one or more EETs or epoxides of EPA or of DHA, or of both), and/or the agent that reduces and/or inhibits ER stress are specifically, predominantly or preferentially targeted to bone tissue. Methods for preferentially targeting therapeutic agents to bone tissues are known in the art and find use. Illustrative methods are described, e.g., Cole, et al,

*Adv Drug Deliv Rev.* (2015) Oct. 19. pii: S0169-409X(15) 00230-6; Hirabayashi, et al., *Clin Pharmacokinet.* (2003) 42(15):1319-30; Gittens, et al, *Adv Drug Deliv Rev.* (2005) May 25; 57(7):1011-36; Uludaq, *Curr Pharm Des.* 2002; 8(21):1929-44; Jahnke, et al., *Angew Chem Int Ed Engl.* 2015 Oct. 12. doi: 10.1002/anie.201507064; Yao, et al., *Bone.* 2015 January; 70:62-5; Gu, et al., *Int J Nanomedicine.* 2013; 8:2305-17 and Yang, et al., *Expert Opin Drug Deliv.* 2009 August; 6(8):851-64.

Furthermore, the agent that increases epoxygenated fatty acids and the agent that inhibits and/or reduces ER stress can be co-formulated in a single composition or can be formulated for separate co-administration. Accordingly, in some embodiments, the methods contemplate administration of compositions comprising a pharmaceutically acceptable carrier or excipient, an agent that increases epoxygenated fatty acids (e.g., an sEHI or a pharmaceutically acceptable salt of the inhibitor and, optionally, one or more EETs or epoxides of EPA or of DHA, or of both), and optionally an agent that reduces and/or inhibits ER stress. In some embodiments, the methods comprise administration of an sEHI and one or more epoxides of EPA or of DHA, or of both.

For preparing the pharmaceutical compositions, the pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active components in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

A variety of solid, semisolid and liquid vehicles have been known in the art for years for topical application of agents to the skin. Such vehicles include creams, lotions, gels, balms, oils, ointments and sprays. See, e.g., Provost C. "Transparent oil-water gels: a review," Int J Cosmet Sci. 8:233-247 (1986), Katz and Poulsen, Concepts in biochemical pharmacology, part I. In: Brodie B B, Gilette J R, eds. Handbook of Experimental Pharmacology. Vol. 28. New York, N.Y.: Springer; 107-174 (1971), and Hadgcraft, "Recent progress in the formulation of vehicles for topical applications," Br J Dermatol., 81:386-389 (1972). A number of topical formulations of analgesics, including capsaicin (e.g., Capsin®), so-called "counter-irritants" (e.g., Icy-Hot®, substances such as menthol, oil of wintergreen, camphor, or eucalyptus oil compounds which, when applied to skin over an area presumably alter or off-set pain in joints or muscles served by the same nerves) and salicylates (e.g. BenGay®), are known and can be readily adapted for topical administration of sEHI by replacing the active ingredient or ingredient with an sEHI, with or without EETs. It is presumed that the person of skill is familiar with these various vehicles and preparations and they need not be described in detail herein.

The agent that increases epoxygenated fatty acids (e.g., an inhibitor of sEH, an EET, an epoxygenated fatty acid, and mixtures thereof), optionally mixed with an anti-inflammatory and/or analgesic agent, can be mixed into such modalities (creams, lotions, gels, etc.) for topical administration. In general, the concentration of the agents provides a gradient which drives the agent into the skin. Standard ways of determining flux of drugs into the skin, as well as for modifying agents to speed or slow their delivery into the skin are well known in the art and taught, for example, in Osborne and Amann, eds., Topical Drug Delivery Formulations, Marcel Dekker, 1989. The use of dermal drug delivery agents in particular is taught in, for example, Ghosh et al., eds., Transdermal and Topical Drug Delivery Systems, CRC Press, (Boca Raton, Fla., 1997).

In some embodiments, the agents are in a cream. Typically, the cream comprises one or more hydrophobic lipids, with other agents to improve the "feel" of the cream or to provide other useful characteristics. In one embodiment, for example, a cream may contain 0.01 mg to 10 mg of sEHI, with or without one or more EETs, per gram of cream in a white to off-white, opaque cream base of purified water USP, white petrolatum USP, stearyl alcohol NF, propylene glycol USP, polysorbate 60 NF, cetyl alcohol NF, and benzoic acid USP 0.2% as a preservative. In various embodiments, an agent that increases epoxygenated fatty acids (e.g., an sEHI or a pharmaceutically acceptable salt of the inhibitor and, optionally, one or more EETs or epoxides of EPA or of DHA, or of both), and/or an agent that reduces and/or inhibits ER stress can be mixed into a commercially available cream, Vanicream® (Pharmaceutical Specialties, Inc., Rochester, Minn.) comprising purified water, white petrolatum, cetearyl alcohol and ceteareth-20, sorbitol solution, propylene glycol, simethicone, glyceryl monostearate, polyethylene glycol monostearate, sorbic acid and BHT.

In other embodiments, the agent or agents are in a lotion. Typical lotions comprise, for example, water, mineral oil, petrolatum, sorbitol solution, stearic acid, lanolin, lanolin alcohol, cetyl alcohol, glyceryl stearate/PEG-100 stearate, triethanolamine, dimethicone, propylene glycol, microcrystalline wax, tri (PPG-3 myristyl ether) citrate, disodium EDTA, methylparaben, ethylparaben, propylparaben, xanthan gum, butylparaben, and methyldibromo glutaronitrile.

In some embodiments, the agent is, or agents are, in an oil, such as jojoba oil. In some embodiments, the agent is, or agents are, in an ointment, which may, for example, white petrolatum, hydrophilic petrolatum, anhydrous lanolin, hydrous lanolin, or polyethylene glycol. In some embodiments, the agent is, or agents are, in a spray, which typically comprise an alcohol and a propellant. If absorption through the skin needs to be enhanced, the spray may optionally contain, for example, isopropyl myristate.

In varying embodiments, the agent or agents are formulated as oral compositions for delivery to the oral cavity of a mammal, e.g., in the form of toothpastes, mouth washes, oral gels, oral varnishes, and oral mucoadhesives. Illustrative excipients for use in oral compositions include without limitation, polyethylene glycols, humectants, vegetable oils, medium chain mono, di and triglycerides, lecithin, waxes, hydrogenated vegetable oils, colloidal silicon dioxide, polyvinylpyrrolidone (PVP) ("povidone"), celluloses, CARBOPOL™ polymers (Lubrizol Advanced Materials, Inc.) (i.e. crosslinked acrylic acid-based polymers), acrylate polymers, other hydrogel forming polymers, plasticizers, crystallization inhibitors, bulk filling agents, solubilizers, bioavailability enhancers and combinations thereof. In one embodiment, the agent or agents are formulated in a mucosal bioadhesive slow release carrier in the form of a mucoadhesive tablet. The mucosal bioadhesive slow release carrier comprises the agent or agents as the active ingredient, at least one diluent, at least one bioadhesive agent and at least one sustained release agent that provides sustained release of the active ingredient. This mucosal bioadhesive slow release carrier can also comprise a flowing agent, a wetting agent, a coloring agent, a flavouring agent and a binding agent. In varying embodiments, the bioadhesive agent can be a synthetic or a natural protein or a polysaccharide. The natural protein can be of vegetal or animal origin. It can be selected from the group of natural pea proteins, natural wheat proteins and gliadin proteins. In another aspect the natural protein can be from a milk protein concentrate. Proteins of natural origin of vegetal origin of use include those described in EP 07006042.1. Examples include natural pea proteins, natural wheat proteins and gliadin proteins and mixtures thereof. The method for producing pea proteins is described in WO 2007/017571. Polysaccharides useful in the formulation of oral mucosal bioadhesives include chitosan, alginate, carboxymethyl cellulose, hydroxypropyl methyl cellulose, hydroxyethyl cellulose, hydroxypropyl cellulose, cyclodextrin, sodium hyaluronate and xanthum gum. In another embodiment the protein of natural origin includes milk protein concentrate, e.g., by titrating a minimum of 85% of proteins, e.g., such as Prosobel L85, milk protein concentrate or, Promilk 852A sold by Armor Proteins, or from the Alaplex range (4850, 1180, 1380 or 1395) from NZMP. In varying embodiments, the relative concentration of the milk natural proteins in the bioadhesive tablet of the invention can be 15% to 50% by weight, preferably 20% to 30% by weight. In addition to the natural proteins, the mucosal bioadhesive slow release carrier contains at least one sustained release agent that provides sustained release of the active ingredient. This mucosal bioadhesive slow release carrier can also comprise a flowing agent, a wetting agent, a coloring agent, a flavouring agent and a binding agent.

Whatever the form in which the agents that inhibit sEH are topically administered (that is, whether by solid, liquid, lotion, gel, spray, etc.), in various embodiments they are administered at a dosage of about 0.01 mg to 10 mg per 10 $cm^2$. An exemplary dose for systemic administration of an inhibitor of sEH is from about 0.001 µg/kg to about 100 mg/kg body weight of the mammal. In various embodiments, dose and frequency of administration of an sEH inhibitor are selected to produce plasma concentrations within the range of 2.5 µM and 30 nM.

The agent that increases epoxygenated fatty acids (e.g., an inhibitor of sEH, an EET, an epoxygenated fatty acid, and mixtures thereof), optionally mixed with an anti-inflammatory and/or analgesic agent, can be introduced into the bowel by use of a suppository. As is known in the art, suppositories are solid compositions of various sizes and shapes intended for introduction into body cavities. Typically, the suppository comprises a medication, which is released into the immediate area from the suppository. Typically, suppositories are made using a fatty base, such as cocoa butter, that melts at body temperature, or a water-soluble or miscible base, such as glycerinated gelatin or polyethylene glycol.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification.

A therapeutically effective amount or a sub-therapeutic amount of the agent that increases epoxygenated fatty acids can be co-administered with the agent that reduces and/or inhibits ER stress (e.g., PBA). The dosage of the specific compounds depends on many factors that are well known to those skilled in the art. They include for example, the route of administration and the potency of the particular compound. An exemplary dose is from about 0.001 µg/kg to about 100 mg/kg body weight of the mammal. Determination of an effective amount is well within the capability of those skilled in the art, especially in light of the detailed disclosure provided herein. Generally, an efficacious or effective amount of a combination of one or more polypeptides of the present invention is determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in *Goodman and Gilman's The Pharmacological Basis of Therapeutics,* 12th Edition, 2010, McGraw-Hill Professional; in a Physicians' Desk Reference (PDR), 70$^{th}$ Edition, 2016, PDR Network; in *Remington: The Science and Practice of Pharmacy,* 21$^{st}$ Ed., 2005, supra; and in *Martindale: The Complete Drug Reference,* Sweetman, 2005, London: Pharmaceutical Press., and in Martindale, *Martindale: The Extra Pharmacopoeia,* 31st Edition., 1996, Amer Pharmaceutical Assn, each of which are hereby incorporated herein by reference.

EETs, EpDPEs, or EpETEs are unstable, and can be converted to the corresponding diols, in acidic conditions, such as those in the stomach. To avoid this, EETs, EpDPEs, or EpETEs can be administered intravenously or by injection. EETs, EpDPEs, or EpETEs intended for oral administration can be encapsulated in a coating that protects the compounds during passage through the stomach. For example, the EETs, EpDPEs, or EpETEs can be provided with a so-called "enteric" coating, such as those used for some brands of aspirin, or embedded in a formulation. Such enteric coatings and formulations are well known in the art. In some formulations, the compositions are embedded in a slow-release formulation to facilitate administration of the agents over time.

It is understood that, like all drugs, sEHIs have half-lives defined by the rate at which they are metabolized by or excreted from the body, and that the sEHIs will have a period following administration during which they are present in amounts sufficient to be effective. If EETs, EpDPEs, or EpETEs are administered after the sEHI is administered, therefore, it is desirable that the EETs, EpDPEs, or EpETEs be administered during the period during which the sEHI are present in amounts to be effective in delaying hydrolysis of the EETs, EpDPEs, or EpETEs. Typically, the EETs, EpDPEs, or EpETEs are administered within 48 hours of administering an sEH inhibitor. Preferably, the EETs, EpDPEs, or EpETEs are administered within 24 hours of the sEHI, and even more preferably within 12 hours. In increasing order of desirability, the EETs, EpDPEs, or EpETEs are administered within 10, 8, 6, 4, 2, hours, 1 hour, or one half hour after administration of the inhibitor. When co-administered, the EETs, EpDPEs, or EpETEs are preferably administered concurrently with the sEHI.

6. Methods of Monitoring

Clinical efficacy can be monitored using any method known in the art.

Measurable parameters to monitor efficacy will depend on the condition being treated. For monitoring the status or improvement of one or more symptoms associated with bone loss and/or periodontitis (e.g., bone density, bone mass, gum inflammation; gum recession), both subjective parameters (e.g., patient reporting, pain, inflammation, posture) and objective parameters (e.g., bone mineral density (BMD), bone mass, blood and/or urine markers indicative of bone metabolism, including without limitation N-telopeptide; NTx; C-telopeptide; CTx; Deoxypyridinoline; DPD; Pyridinium Crosslinks; Tartrate-resistant Acid Phosphatase; TRAP; Bone-specific Alkaline Phosphatase; Osteocalcin; P1NP; Procollagen Type 1 N-Terminal Propeptide, calcium, phosphorus, parathyroid hormone and alkaline phosphatase). Additional measurable parameters include without limitation visual inspection of amelioration of inflammatory lesions in the oral cavity, e.g., maxillary buccal mucosa, mandibular buccal mucosa, maxillary attached gingiva, mandibular attached gingiva, molar salivary gland, areas lateral to palatoglossal folds, oropharyngeal tissue, lingual and/or sublingual tissues). Applicable assays for the monitoring of bone density, bone mass and bone metabolism are known in the art. Behavioral changes in the subject (e.g., exhibition of pain in walking, standing, sitting or chewing, posture) are also relevant to all diseases and disease conditions associated with and/or caused at least in part by bone loss. These parameters can be measured using any methods known in the art. In varying embodiments, the different parameters can be assigned a score. Further, the scores of two or more parameters can be combined to provide an index for the subject.

Observation of the stabilization, improvement and/or reversal of one or more symptoms or parameters by a measurable amount indicates that the treatment or prevention regime is efficacious. Observation of the progression, increase or exacerbation of one or more symptoms indicates that the treatment or prevention regime is not efficacious. For example, observation of the improvement of one or both of subjective parameters (e.g., patient reporting, pain, inflammation, posture) and objective parameters (e.g., gum inflammation, gum recession, inflammatory lesions in the oral cavity, bone mineral density (BMD), bone mass, blood and/or urine markers indicative of bone metabolism, including without limitation N-telopeptide; NTx; C-telopeptide; CTx; Deoxypyridinoline; DPD; Pyridinium Crosslinks; Tartrate-resistant Acid Phosphatase; TRAP; Bone-specific Alkaline Phosphatase; Osteocalcin; P1NP; Procollagen Type 1 N-Terminal Propeptide, calcium, phosphorus, parathyroid hormone and alkaline phosphatase) and/or behavioral changes in the subject (e.g., decreased pain, improved posture, increased bone density and mass) after one or more administrations of agent that increases epoxygenated fatty acids (e.g., an inhibitor of sEH) indicates that the treatment or prevention regime is efficacious. Likewise, observation of reduction or decline or lack of improvement, or worsening of one or both of subjective parameters (e.g., patient reporting, pain, inflammation, posture) and objective parameters (e.g., gum inflammation, gum recession, inflammatory lesions in the oral cavity, bone mineral density (BMD), bone mass, blood and/or urine markers indicative of bone metabolism, including without limitation N-telopeptide; NTx; C-telopeptide; CTx; Deoxypyridinoline; DPD; Pyridinium Crosslinks; Tartrate-resistant Acid Phosphatase; TRAP; Bone-specific Alkaline Phosphatase; Osteocalcin; P1NP; Procollagen Type 1 N-Terminal Propeptide, calcium, phosphorus, parathyroid hormone and alkaline phosphatase), and/or behavioral changes in the subject (e.g., exhibition of pain in walking, standing, sitting or chewing, posture) after one or more administrations of the agent that increases epoxygenated fatty acids (e.g., an inhibitor of sEH) indicates that the treatment or prevention regime is not efficacious. Similarly, observation of the amelioration of one or more inflammatory lesions in the oral cavity, e.g., maxillary buccal mucosa, mandibular buccal mucosa, maxillary attached gingiva, mandibular attached gingiva, molar salivary gland, areas lateral to palatoglossal folds, oropharyngeal tissue, lingual and/or sublingual tissues) after one or more administrations of the agent that increases epoxygenated fatty acids (e.g., an inhibitor of sEH) indicates that the treatment or prevention regime is efficacious. Observation of increased numbers or severity of inflammatory lesions in the oral cavity, e.g., maxillary buccal mucosa, mandibular buccal mucosa, maxillary attached gingiva, mandibular attached gingiva, molar salivary gland, areas lateral to palatoglossal folds, oropharyngeal tissue, lingual and/or sublingual tissues) after one or more administrations of the agent that increases epoxygenated fatty acids (e.g., an inhibitor of sEH) indicates that the treatment or prevention regime was not efficacious.

In certain embodiments, the monitoring methods can entail determining a baseline value of a measurable biomarker or disease parameter in a subject before administering a dosage of the one or more active agents described herein, and comparing this with a value for the same measurable biomarker or parameter after a course of treatment.

In other methods, a control value (i.e., a mean and standard deviation) of the measurable biomarker or parameter is determined for a control population. In certain embodiments, the individuals in the control population have not received prior treatment and do not have the disease condition subject to treatment (e.g., osteoporosis, periodontal disease, osteoclastogenesis), nor are at risk of developing the disease condition subject to treatment (e.g osteoporosis, periodontal disease, osteoclastogenesis). In such cases, if the value of the measurable biomarker or clinical parameter approaches the control value, then treatment is considered efficacious. In other embodiments, the individuals in the control population have not received prior treatment and have been diagnosed with the disease condition subject to treatment (e.g., osteoporosis, periodontal disease, osteoclastogenesis). In such cases, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and need not be resumed. In all of these cases, a significant difference relative to the control level (i.e., more than a standard deviation) is an indicator that treatment should be resumed in the subject.

7. Compositions

Further provided are compositions comprising one or more agents that increase the production and/or level of epoxygenated fatty acids formulated for delivery to the oral cavity of a mammal, as described above and herein. Such compositions include without limitation toothpastes, mouth washes, oral gels, oral varnishes, and oral mucoadhesives. In varying embodiments, the orally formulated compositions comprise one or more agents that increase the production and/or level of epoxygenated fatty acids and one or more inhibitors of endoplasmic reticular stress. Embodiments of the agents that increase the production and/or level of epoxygenated fatty acids and embodiments of inhibitors of endoplasmic reticular stress are as described above and herein. Embodiments of formulations of the agents are as described above and herein.

EXAMPLES

The following examples are offered to illustrate, but not to limit the claimed invention.

Example 1

Soluble Epoxide Hydrolase Pharmacological Inhibition Decreases Alveolar Bone Loss by Modulating Host Inflammatory Response, RANK-Related Signaling, ER Stress and Apoptosis Materials and Methods

*Aggregatibacter actinomycetemcomitans* (JP2) was purchased from ATCC (Manassas, Va.) and cultured in-house under anaerobic conditions to ensure viability and virulance.

Chemicals:

The sEH inhibitor 1-(1-propanoylpiperidin-4-yl)-3-[4-(trifluoromethoxy)phenyl]urea was synthesized in-house, purified and chemically characterized as described earlier (Rose et al., 2010). The methyl ester of arachidonic acid was from NuChek Prep Inc (Elysian, Minn.). Chromatography grade solvents for HPLC were obtained from Fisher Scientific (Pittsburgh, Pa.). Standards for LCMS/MS analysis were purchased from Cayman Chemical (Ann Arbor, Mich.). The EET methyl esters were synthesized, purified and characterized in-house using procedures published previously (Morisseau et al., 2010). The final regioisomeric mixture was analyzed using LC-MS/MS to ensure purity and regioisomeric ratio which was 2.2:1.6:1.1:1, for 14, 15-:11, 12-: 8, 9-: 5, 6-EpETrE, respectively).

Bacterial Viability:

The potential bacteriostatic or bactericidal effects of TPPU at the administered dose were tested in vitro. The microbial inoculum of *A. actinomycetemcomitans* was prepared and adjusted to $5\times10^6$ colony forming units (CFU)/mL in tryptic soy broth. TPPU was then dissolved to a final concentration of 10 µM in polyethylene glycol (PEG400; Fisher Scientific, Nidderau, Germany) and was added and incubated at 37° C. for 24 hours anaerobically. PEG400 solution without the inhibitor was used as a control. Experiments were performed in duplicates on three different days.

Animals and Animal Care:

C57BL/6 (WT, wild type) and sEH−/− (KO, knockout) male mice were maintained under standard conditions, 23±1° C., 12-h light-dark cycle, ad libitum food and water in housing facilities at UC Davis. Animals were age-matched and each group consisted of 8 mice, 6-7 week old and weighing 20-25 g. All procedures were in agreement with standards for the care of laboratory animals as outlined in the NIH Guide for the Care and Use of Laboratory Animals. All procedures were performed according to institutional guidelines for animal experimentation and were approved by the Animal Resource Services of the University of California, Davis, which is accredited by the American Association for the Accreditation of Laboratory Animal Care.

Periodontitis Model and Treatments:

Animals orally received $1\times10^9$ CFU/ml of a diluted culture of freshly grown *A. actinomycetemcomitans* JP2, in a volume of 100 µl PBS containing 2% carboxymethylcellulose. The solution was placed into the oral cavity with a micropipette, and the procedure was repeated at 48 and 96 h after the first inoculation. Treatment with TPPU and EETs was initiated after the third inoculation of bacteria. The inhibitor was dissolved in PEG400 and administered at 1 mg/kg/day by oral gavage. For the treatment with EETs, we attempted to apply viscous solution of mixture of EET-methyl ester regioisomers dissolved in PEG400 to the gum tissue using a fine pipette at a dose of 1 µg/kg/day. The mice received the entire EET dose. This was done immediately before the oral gavage with both groups of mice receiving TPPU or mice receiving vehicle alone. Because EETs are unstable in stomach acid we assume exposure is largely topical or buccal. All treatments continued for 15 days. The plasma and blood concentration of TPPU was quantified as previously described by LC-MS analysis (Ostermann et al., 2015). The negative control group consisted of uninfected mice (sham-infected), the positive control group was infected and received the vehicle only. One day after the treatment period (16th day), animals were sacrificed by cardiac puncture after anesthesia with xylazine/ketamine. Plasma and whole blood were sampled and frozen until analysis.

Quantification of Alveolar Bone Loss:

Evaluation of alveolar bone loss was performed as described previously (Napimoga et al., 2013). Sixteen days after the third inoculation, animals were sacrificed, the jaws were removed, and defleshed, then immersed overnight in 3% hydrogen peroxide, and stained with 1% methylene blue in PBS. Horizontal bone loss was assessed morphometrically by measuring the distance between the cement-enamel junction and the alveolar bone crest of the first and second molars. Measurements at 14 buccal sites per mouse (7 sites each on the left and right maxillary molars) were made under a microscope, pictures were taken and bone measurements were analyzed using the Image J software suit. Random and blinded measurements were taken by the same calibrated person (C.A.T.d.S.). Intraexaminer reproducibility of the measurements achieved >90%.

Western Blotting:

Western blotting was performed as described earlier (Bettaieb et al., 2013). Briefly, tissues were lysed first and clarified by centrifugation and protein concentrations were determined using the bicinchoninic acid protein assay kit (ThermoFisher Scientific, Waltham Mass.). Equal amounts of protein (20 µg) from the gingival tissue were resolved by SDS-PAGE and transferred to PVDF membranes. Immunoblotting of lysates was performed with antibodies for MCP1 (Biolegend; San Diego, Calif.), pp38 (Thr180/Tyr182), p38, pJNK (Thr183/Tyr185), JNK or cCasp3 (Cell Signaling Technology; Beverly, Mass.), RANK, RANKL, OPG or α-Tubulin (Santa Cruz Biotechnology; Santa Cruz, Calif.). Antibodies for sEH were generated in-house using recombinantly expressed mouse sEH following affinity purification. After incubation with the appropriate secondary antibodies, proteins were visualized using Luminata™ Fort Western HRP substrate (Millipore). Pixel intensities of immunoreactive bands were quantitated using FluorChem Q Imaging software (Alpha Innotech). For phosphorylated proteins data were presented as phosphorylation level normalized to total protein expression and for non-phosphorylated proteins as total protein expression normalized to α-Tubulin.

Statistical Analysis:

The statistical analyses were performed using Prism 5.0 or the SigmaPlot Software Suit. The data were first examined for normality using the Kolmogorov-Smirnov test, and then analyzed using one-way ANOVA. If there was a significant among-subjects main effect for the treatment group following one-way ANOVA, or one way ANOVA on ranks, post-hoc contrasts, using the Student Newman Keuls multiple comparison or Tukey's all pairwise post-hoc tests. Data are presented as mean±S.E.M.

Results

TPPU does not Affect Bacterial Viability.

In the present study we tested the potential effects of TPPU, a potent and selective pharmacological inhibitor of sEH, to inhibit bone loss caused by periodontal disease in mouse-induced periodontitis model. TPPU or its vehicle did not have bacteriostatic or bactericidal effect on the cultures used to induce the periodontal disease. As demonstrated in FIG. 1, no change in the growth of the *A. actinomycetemcomitans* was observed in the presence or absence of TPPU.

Chemical Inhibition of sEH Reduces Bone Loss.

Figure 3:
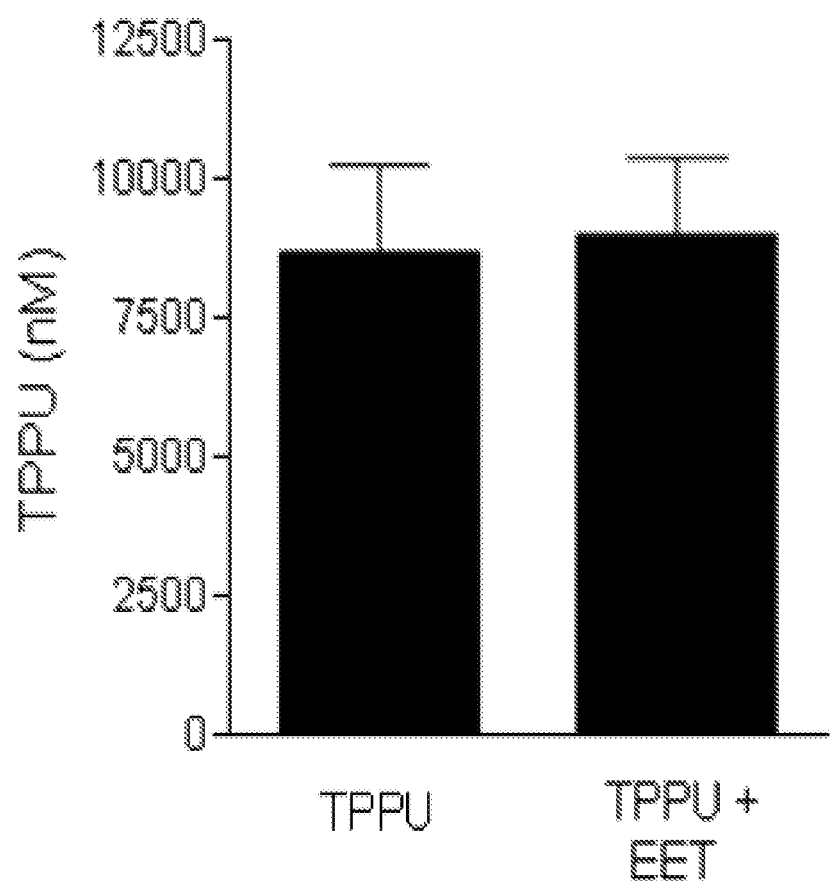
FIG. 3 illustrates blood concentration of TPPU. At the end of the 15 day treatment period we quantified blood levels of TPPU from TPPU and TPPU+EET-methyl ester treated groups. The samples were taken at 24 h after the last oral gavage treatment. In both treatment groups TPPU levels were well above the theoretical $IC_{90}$ levels by a large margin suggesting strong and systemic inhibition of sEH activity. The results are expressed as mean±SD from six mice per group.

There were no *A. actinomycetemcomitans* in the oral cavities of mice prior to deliberate infection. On the other hand, persistent oral colonization by the pathogen was confirmed in all infected animals on the last day. Next, bone loss was quantified in all mice (FIG. 2A). Sham-infected animals presented the lowest distance between CEJ (cement-enamel junction) and ABC (alveolar bone crest) during the experimental period (FIG. 2B). On the other hand, animals orally infected with *A. actinomycetemcomitans*, but received no treatment, showed significantly greater bone loss when compared to the uninfected animals (FIG. 2C). Animals infected and orally treated with EET-methyl esters at a dose of 1 µg/kg/day did not display a significant reduction in bone loss (FIG. 2D). In contrast, mice treated with TPPU had significantly lower bone loss than the untreated infected animals and was comparable to the levels of uninfected animals (FIG. 2E). Moreover, consistent with this observation the mice that received combination of TPPU and EET-methyl esters had significantly lower bone loss compared to untreated infected animals (FIG. 2F). However, this decrease was not significantly more than the TPPU group (p=0.53). Using this dosing scheme, one would expect a near complete and sustained inhibition of sEH activity. Blood concentration of TPPU at the end of the experiment also supports the argument that the target enzyme is significantly inhibited. Groups of mice that received TPPU and TPPU+EET-methyl esters had more than 8 µg/mL of TPPU detected in the blood, even after 24 h of the last oral administration (FIG. 3). There were no differences regarding the blood TPPU concentration in the group that received TPPU+EET-methyl esters. These levels reiterate the argument that the target enzyme is significantly inhibited (Liu et al., 2009; Liu et al., 2010; Rose et al., 2010). Thus, in these studies TPPU was sufficiently stable in vivo to provide effective concentrations throughout the course of the experiment.

Genetic Ablation of sEH Recapitulates the Effects of sEH Inhibitor on Bone Loss.

To support the results of sEH pharmacological inhibition, we performed similar experiment using sEH global knockout mice. Consistent with the results obtained earlier, wild type mice infected with *A. actinomycetemcomitans*, showed significantly greater bone loss when compared to the uninfected animals (FIG. 4). Remarkably, infected sEH knockout mice displayed highly significant reduction in bone loss, similar to the levels of uninfected group (FIGS. 4D and 4E). Findings using sEH knockout mice recapitulate observations from sEH pharmacological inhibition using TPPU.

Inhibition of sEH Alters Key Regulators of Bone Remodeling.

To understand the basis of these effects we determined the levels of key regulators of bone remodeling, a highly dynamic process. The RANK/RANKL/OPG system is generally accepted as a master regulator of bone loss and regeneration (Lacey et al., 1998). RANKL synthesized by osteoblasts, cells that synthesize new bone, targets RANK on the osteoclasts, cells that resorb bone.

This stimulates bone loss by activating osteoclasts. The third arm of the system is osteoblast derived OPG, which is a soluble decoy receptor for RANKL and prevents its binding to RANK and thereby fine tuning bone remodeling. As expected, in infected control mice, levels of RANK, RANKL, OPG and MCP-1 in the gum tissue were increased, compared to uninfected animals (FIG. 5). This reiterates the imbalance in bone remodeling process as well as increased infiltration of cells that mediate inflammation, arguments supported by data presented here. In contrast, TPPU treatment significantly reduced the expression of these biomarkers. Consistent with the TPPU group, animals treated with TPPU+EET-methyl esters (1 µg/kg) displayed a nearly identical profile in the expression of all four proteins quantified (FIG. 5). Equally importantly, in sEH KO mice infected with *A. actinomycetemcomitans*, the effects of TPPU treatment were recapitulated. More specifically, in sEH KO mice levels of RANK, RANKL, and MCP-1 were similar to TPPU treated group, while they displayed slightly higher levels of OPG (FIG. 5B-E). However, the higher levels of OPG could be seen as an advantage since this would lead to less bone loss. Overall, these results underline the accelerated and incongruent bone remodeling in periodontal disease and that these pathological changes can be re-calibrated by sEH deletion or pharmacological inhibition.

The significant reduction in MCP-1 expression is suggestive of a decrease in inflammatory cell migration and therefore inflammation. Therefore, we further monitored key downstream kinases known to be phosphorylated in response to inflammatory signals. Two stress kinases, p38 and JNK activate their respective signaling cascades, increase inflammation, cytokine synthesis and apoptosis.

In the gingival tissue of infected mice, levels of pJNK (phosphorylated JNK) and pp38 (phosphorylated p38) were largely increased supporting the idea that dysregulated host responses have a pivotal role in periodontal disease. In contrast, treatment with TPPU, TPPU+EET-methyl esters or in sEH KO mice infected with *A. actinomycetemcomitans*, phosphorylation of both kinases were greatly reduced (FIG. 6). These observations are consistent with the argument that sEH inhibition dampens inflammatory response in periodontal disease.

The sEH is a significant regulator of endoplasmic reticulum (ER) stress response (Bettaieb et al., 2013; Bettaieb et al., 2015; Harris et al., 2015). Therefore, we evaluated whether ER stressmediated pathways are active in periodontal disease and if sEH deletion or pharmacological inhibition attenuate ER stress response. We observed the activation of the two major branches of the ER stress signaling cascade in the gingival tissue samples. While the levels of phosphorylated pPERK and pIRE1α were below the detection limit in untreated wild type and sEH knockout mice, they were significantly elevated in the gum tissue of mice infected with *A. actinomycetemcomitans* (FIG. 7). Consistent with their phosphorylation, downstream targets for each ER stress sensor (eIF2α and spliced) (BPI) were significantly elevated in infected mice. Phosphorylated eIF2α and spliced X-box binding protein 1 (sXbp1), were below the level of detection in healthy tissues but were significantly increased in mice with periodontal disease. Notably, sEH knockout mice infected with *A. actinomycetemcomitans* displayed significantly lower ER stress compared to wild type animals infected with *A. actinomycetemcomitans*. However, markers of ER stress were higher in knockout mice compared to TPPU treated wild type animals. This observation suggests that chemical inhibition of sEH was more efficacious in attenuating ER stress. On the other hand, there was no difference between TPPU alone or in the presence of EET-methyl esters at the concentrations tested ($p>0.05$).

A consequence of activation of ER stress sensors is a decrease in general protein synthesis and an increase in components that assist in overcoming stress. However, if these compensatory mechanisms fail to restore/maintain homeostasis then the cells will engage apoptosis. To determine if periodontal disease leads to intense inflammatory conditions and ER stress that compel the cells to activate apoptotic cascades we monitored the levels of cleaved Caspase-3 (FIG. 8). Caspase-3 is activated by upstream caspases, and is an integrator and marker of activation of the apoptotic signaling pathway. c-Caspase-3 expression was exceedingly low under normal conditions, much like the other markers used in this study. However, infection by *A. actinomycetemcomitans* significantly increased the levels of c-Caspase-3 in all mice, but most remarkably in the vehicle control group (FIG. 8). This supports the hypothesis that activated ER stress in periodontal disease is linked to cell death. In contrast, mice treated with TPPU, TPPU+EET-methyl esters or the sEH knockout mice displayed significantly lower levels of c-Caspase-3. This observation suggests that inhibition of sEH was largely able to reduce ER stress and the ensuing apoptosis. However, given the remaining 10-fold increase in c-Caspase-3 in treated groups, other inflammation associated apoptotic signaling cascades may not have been targeted by inhibition of sEH.

Discussion

The pathogenesis of periodontal disease is recognized as infection-induced inflammatory tissue destruction. At the site of tissue destruction, cytokines, and inflammatory mediators are elevated. The prevalence of periodontitis in the US adult population is estimated at over 47%. In adults aged 65 and older, 64% had either moderate or severe stages of periodontal disease (Eke et al., 2012). This prevalence rate highlights the uniqueness of periodontal disease among other conditions. Therefore, efforts to understand the pathophysiology of the disease as well as different approaches to control it should result in tremendous health benefits. In the present study, we demonstrated that an inhibitor of sEH largely abrogates bone loss caused by periodontal disease. This seems to be based on the effects of inhibition of sEH to decrease key osteoclastogenic molecules, as well as lowering inflammation triggered ER stress and associated apoptosis in the gingival tissue.

Epoxy fatty acid generation from ARA and other unsaturated fatty acids is the third and latest major branch of the ARA cascade. The epoxyeicosatrienoic acids seem to have mostly antiinflammatory functions that are in contrast to pro-inflammatory products of the other two branches (Capdevila et al., 1981). Multiple cytochrome P450s form epoxy fatty acids and ARA for example is converted into 5,6-EET, 8,9-EET, 11,12-EET, and 14,15-EET, all of which have biological activity.

Early evidence on the anti-inflammatory effects of 11,12-EET by preventing tumor necrosis factor-α (TNF-α)-induced activation of NF-κB and the subsequent increase in VCAM-1 (vascular cell adhesion molecule-1) expression in mice is recently supported by other studies(Node et al., 1999; Chiamvimonvat et al., 2007). However, in vivo, all EET regioisomers are degraded quickly by sEH, leading to the production of metabolites known as dihydroxyeicosatrienoic acids (DHETs). Thus, in the absence of a sEH inhibitor most of the biological effects of EETs are difficult to observe. The potent inhibitor of sEH TPPU stabilizes the EETs and other epoxy fatty acids in vivo and promotes anti-inflammatory processes. The presumed mechanism of the therapeutic effect seems to involve homeostatic regulation of the RANK, RANKL and OPG system, a master regulator of osteoclastogenesis. Furthermore, inhibition of sEH also decreases the chemokine MCP-1 as would be expected from the anti-inflammatory effects of sEH inhibition. Overall results are nearly identical across chemical inhibitor and global knockout mice, highly supportive of the idea that inhibition of sEH rather than inhibitor structure specific pharmacological efficacy.

Another line of evidence reported recently also argues for the activity of EETs to prevent bone loss in a different experimental paradigm (Guan et al., 2015). In an ovariectomy induced mouse model of bone loss, administration of EETs seem to prevent bone loss through a similar mechanism in which EETs normalize the plasma RANKL to OPG ratio, while RANK levels were not reported. Instead, authors demonstrate suppression of RANK by the free acid forms of EETs, in bone marrow mononuclear cells and the RAW264.7 cell line when induced by treating the cells with RANKL. In the ovariectomized mice, the prominent mechanism of bone loss seems to be driven by decrease in OPG. In contrast, we report the levels of RANK, RANKL and OPG are all increased in gingival tissue by approximately 6-fold in response to inflammation. These differences highlight the mechanistic distinction between the ovariectomy and periodontal disease induced bone loss models. Remarkably, in TPPU treated and sEH knockout mice in our study, RANK, RANKL and OPG were normalized to nearly pre-infection levels suggesting a potential therapeutic effect. This is of course an expected difference from the earlier study given that EETs have short in vivo half-lives and inhibition of sEH stabilizes these molecules by preventing their degradation by the sEH enzymatic activity. TPPU is easy to administer orally or in drinking water, yields high exposure and is a potent inhibitor of sEH (Rose et al., 2010). It is also important to highlight that in our study, administration of EET-methyl esters alone topically and directly onto the periodontal tissue did not prevent the inflammatory periodontal bone loss. However, the EET-methyl esters in the presence of TPPU displayed detectable changes in markers of ER stress (FIG. 7). Overall, the findings demonstrate that inhibition of sEH is a viable approach to treat complex conditions that include progressive bone loss.

An active periodontal lesion is characterized by the prominent infiltration of B and T cells (Okada et al., 1983). Adoptive transfer of RANKL+, antigen-specific T cells induce bone loss in rat periodontal tissue that received local injection of the T-cell antigen. Furthermore, T and B cells are likely the major sources of RANKL in the inflamed gingival tissues (Kawai et al., 2006). A benefit of inhibiting the sEH in this study was the sharp decrease in tissue MCP-1 (CCL-2) level. The potent chemoattractant MCP-1 is largely seen as the driver of monocyte infiltration into the gingival tissue. Thus it is plausible that administration of TPPU or in the sEH knockout mice lower levels of MCP-1 decreased the infiltration of inflammatory cells and thereby led to the downregulation of the RANK-RANKL-OPG axis. However, it seems more likely that EETs also had a direct effect on the RANK/RANKL-OPG axis because while markers of ER stress were mostly normalized, expression of RANK, RANKL and OPG were fully restored to pre-infection levels. This observation suggests that decreased inflammatory cell infiltration is a distinct effect of sEH inhibition and is an additional benefit.

Deletion of sEH and its pharmacological inhibition lead to attenuation of the ER stress response in several experimental models (Bettaieb et al., 2013; Harris et al., 2015; Inceoglu et al., 2015). This homeostatic mechanism is involved in numerous pathological conditions including viral and bacterial infection and neurodegenerative diseases (Cao et al., 2016). The ER stress system is typically activated in response to stressors including excessive amounts of unfolded proteins in the endoplasmic reticulum. ER stress response in periodontal disease was recently reported (Domon et al., 2009; Kung et al., 2015; Yamada et al., 2015). These authors suggested that modulation of the ER stress system could have therapeutic effects. Consistent with their prediction, in this study we detected the activation of ER stress in the gingival tissue suggesting that, at the least, ER stress contributed to the development and progression of periodontal disease. The markers of activated ER stress were attenuated by sEH pharmacological inhibition and deletion. Activated ER stress signaling may lead to apoptosis when cells are unable to maintain homeostasis. This was reported in the gingival tissue of diabetic rats with periodontal disease (Kang et al., 2012). Here, we demonstrate the activation of apoptosis in conjunction with ER stress. However, blocking ER stress and inflammation with TPPU was sufficient to prevent apoptosis and this was consistently observed in sEH−/− mice inoculated with *A. actinomycetemcomitans*. These findings are consistent with those reported earlier for periodontal disease models. Specifically, in diabetic rats, *A. actinomycetemcomitans* induced a caspase3-dependent response and led to increased number of cells going through apoptosis in the gingival epithelial and connective tissues and increased bone loss (Kang et al., 2012).

Overall, the results reiterate the importance of the RANK/RANKL/OPG system and its crosstalk with ER stress signaling in periodontal disease. These interactions ultimately give rise to increased apoptosis in the gingival tissue and bone loss. Given the importance and the epidemiology of gingival diseases, therapeutics that selectively targets the elements of the host inflammatory responses should prove useful to improve oral health. Our findings strongly indicate that inhibition of sEH is one such therapeutic approach. Nearly identical results from a small molecule inhibitor of sEH and the mice with genetic knockout of sEH support the idea that positively altering the bioactive lipid mediators including EETs is a viable approach to dampen destructive inflammation, apoptosis and bone loss in periodontal disease.

REFERENCES

Bartold P M and Van Dyke T E (2013) Periodontitis: a host-mediated disruption of microbial homeostasis. Unlearning learned concepts. Periodontol 2000 62:203-217.

Bettaieb A, Chahed S, Bachaalany S, Griffey S, Hammock B D and Haj F G (2015) Soluble Epoxide Hydrolase Pharmacological Inhibition Ameliorates Experimental Acute Pancreatitis in Mice. Mol Pharmacol 88:281-290.

Bettaieb A, Nagata N, AbouBechara D, Chahed S, Morisseau C, Hammock B D and Haj F G (2013) Soluble epoxide hydrolase deficiency or inhibition attenuates diet-induced endoplasmic reticulum stress in liver and adipose tissue. J Biol Chem 288:14189-14199.

Cao S S, Luo K L and Shi L (2016) Endoplasmic Reticulum Stress Interacts With Inflammation in Human Diseases. J Cell Physiol 231:288-294.

Capdevila J, Chacos N, Werringloer J, Prough R A and Estabrook R W (1981) Liver microsomal cytochrome P-450 and the oxidative metabolism of arachidonic acid. Proc Natl Acad Sci USA 78:5362-5366.

Chacos N, Capdevila J, Falck J R, Manna S, Martin-Wixtrom C, Gill S S, Hammock B D and Estabrook R W (1983) The reaction of arachidonic acid epoxides (epoxyeicosatrienoic acids) with a cytosolic epoxide hydrolase. Archives of Biochemistry and Biophysics 223:639-648.

Chiamvimonvat N, Ho C M, Tsai H J and Hammock B D (2007) The soluble epoxide hydrolase as a pharmaceutical target for hypertension. J Cardiovasc Pharmacol 50:225-237.

Domon H, Takahashi N, Honda T, Nakajima T, Tabeta K, Abiko Y and Yamazaki K (2009) Upregulation of the endoplasmic reticulum stress-response in periodontal disease. Clin Chim Acta 401:134-140.

Eke P I, Dye B A, Wei L, Thornton-Evans G O and Genco R J (2012) Prevalence of periodontitis in adults in the United States: 2009 and 2010. J Dent Res 91:914-920.

Flemmig T F (1999) Periodontitis. Ann Periodontol 4:32-38.

Guan H, Zhao L, Cao H, Chen A and Xiao J (2015) Epoxyeicosanoids suppress osteoclastogenesis and prevent ovariectomy-induced bone loss. Faseb J 29:1092-1101.

Haeggstrom J Z, Rinaldo-Matthis A, Wheelock C E and Wetterholm A (2010) Advances in eicosanoid research, novel therapeutic implications. Biochemical and Biophysical Research Communications 396:135-139.

Hajishengallis G, Darveau R P and Curtis M A (2012) The keystone-pathogen hypothesis. Nat Rev Microbiol 10:717-725.

Harris T R, Bettaieb A, Kodani S, Dong H, Myers R, Chiamvimonvat N, Haj F G and Hammock B D (2015) Inhibition of soluble epoxide hydrolase attenuates hepatic fibrosis and endoplasmic reticulum stress induced by carbon tetrachloride in mice. Toxicol Appl Pharmacol 286:102111.

Hasturk H, Kantarci A, Goguet-Surmenian E, Blackwood A, Andry C, Serhan C N and Van Dyke T E (2007) Resolvin E1 regulates inflammation at the cellular and tissue level and restores tissue homeostasis in vivo. J Immunol 179:7021-7029.

Imig J D (2012) Epoxides and soluble epoxide hydrolase in cardiovascular physiology. Physiol Rev 92:101-130.

Inceoglu B, Bettaieb A, Trindade da Silva C A, Lee K S, Haj F G and Hammock B D (2015) Endoplasmic reticulum stress in the peripheral nervous system is a significant driver of neuropathic pain. Proc Natl Acad Sci USA 112:9082-9087.

Inceoglu B, Wagner K, Schebb N H, Morisseau C, Jinks S L, Ulu A, Hegedus C, Rose T, Brosnan R and Hammock B D (2011) Analgesia mediated by soluble epoxide hydrolase inhibitors is dependent on cAMP. Proc Natl Acad Sci USA 108:5093-5097.

Kang J, de Brito Bezerra B, Pacios S, Andriankaja O, Li Y, Tsiagbe V, Schreiner H, Fine D H and Graves D T (2012) Aggregatibacter actinomycetemcomitans infection enhances apoptosis in vivo through a caspase-3-dependent mechanism in experimental periodontitis. Infect Immun 80:2247-2256.

Kawai T, Matsuyama T, Hosokawa Y, Makihira S, Seki M, Karimbux N Y, Goncalves R B, Valverde P, Dibart S, Li Y P, Miranda L A, Ernst C W, Izumi Y and Taubman M A (2006) B and T lymphocytes are the primary sources of RANKL in the bone resorptive lesion of periodontal disease. Am J Pathol 169:987-998.

Kung L H, Rajpar M H, Preziosi R, Briggs M D and Boot-Handford R P (2015) Increased classical endoplasmic reticulum stress is sufficient to reduce chondrocyte proliferation rate in the growth plate and decrease bone growth. PLoS One 10:e0117016.

Lacey D L, Timms E, Tan H L, Kelley M J, Dunstan C R, Burgess T, Elliott R, Colombero A, Elliott G, Scully S, Hsu H, Sullivan J, Hawkins N, Davy E, Capparelli C, Eli A, Qian Y X, Kaufman S, Sarosi I, Shalhoub V, Senaldi G, Guo J, Delaney J and Boyle W J (1998) Osteoprotegerin ligand is a cytokine that regulates osteoclast differentiation and activation. Cell 93:165-176.

Levy B D, Vachier I and Serhan C N (2012) Resolution of inflammation in asthma. Clin Chest Med 33:559-570.

Liu J Y, Tsai H J, Hwang S H, Jones P D, Morisseau C and Hammock B D (2009) Pharmacokinetic optimization of four soluble epoxide hydrolase inhibitors for use in a murine model of inflammation. Br J Pharmacol 156:284-296.

Liu J Y, Yang J, Inceoglu B, Qiu H, Ulu A, Hwang S H, Chiamvimonvat N and Hammock B D (2010) Inhibition of soluble epoxide hydrolase enhances the anti-inflammatory effects of aspirin and 5-lipoxygenase activation protein inhibitor in a murine model. Biochem Pharmacol 79:880-887.

Marnett L J (2009) The COXIB experience: a look in the rearview mirror. Annual Review of Pharmacology and Toxicology 49:265-290.

Morisseau C, Goodrow M H, Dowdy D, Zheng J, Greene J F, Sanborn J R and Hammock B D (1999) Potent urea and carbamate inhibitors of soluble epoxide hydrolases. Proc Natl Acad Sci USA 96:8849-8854.

Morisseau C and Hammock B D (2013) Impact of soluble epoxide hydrolase and epoxyeicosanoids on human health. Annual Review of Pharmacology and Toxicology 53:37-58.

Morisseau C, Inceoglu B, Schmelzer K, Tsai H J, Jinks S L, Hegedus C M and Hammock B D (2010) Naturally occurring monoepoxides of eicosapentaenoic acid and docosahexaenoic acid are bioactive antihyperalgesic lipids. J Lipid Res 51:3481-3490.

Napimoga M R, Clemente-Napimoga J T, Macedo C G, Freitas F F, Stipp R N, Pinho-Ribeiro F A, Casagrande R and Verri W A, Jr. (2013) Quercetin inhibits inflammatory bone resorption in a mouse periodontitis model. J Nat Prod 76:2316-2321.

Napimoga M H, da Silva C A, Carregaro V, Farnesi-de-Assuncao T S, Duarte P M, de Melo N F and Fraceto L F (2012) Exogenous administration of 15d-PGJ2-loaded nanocapsules inhibits bone resorption in a mouse periodontitis model. J Immunol 189:1043-1052.

Node K, Huo Y, Ruan X, Yang B, Spiecker M, Ley K, Zeldin D C and Liao J K (1999) Antiinflammatory properties of cytochrome P450 epoxygenase-derived eicosanoids. Science 285:1276-1279.

Norwood S, Liao J, Hammock B D and Yang G Y (2010) Epoxyeicosatrienoic acids and soluble epoxide hydrolase: potential therapeutic targets for inflammation and its induced carcinogenesis. Am J Transl Res 2:447-457.

Okada H, Kida T and Yamagami H (1983) Identification and distribution of immunocompetent cells in inflamed gingiva of human chronic periodontitis. Infect Immun 41:365-374.

Ortega-Gomez A, Perretti M and Soehnlein O (2013) Resolution of inflammation: an integrated view. EMBO Mol Med 5:661-674.

Ostermann A I, Herbers J, Willenberg I, Chen R, Hwang S H, Greite R, Morisseau C, Gueler F, Hammock B D and Schebb N H (2015) Oral treatment of rodents with soluble epoxide hydrolase inhibitor 1-(1-propanoylpiperidin-4-yl)-3-[4-(trifluoromethoxy)phenyl]urea (TPPU): Resulting drug levels and modulation of oxylipin pattern. Prostaglandins Other Lipid Mediat 121:131-137.

Rose T E, Morisseau C, Liu J Y, Inceoglu B, Jones P D, Sanborn J R and Hammock B D (2010) 1-Aryl-3-(1-acylpiperidin-4-yl)urea inhibitors of human and murine soluble epoxide hydrolase: structure-activity relationships, pharmacokinetics, and reduction of inflammatory pain. J Med Chem 53:7067-7075.

Schmelzer K R, Inceoglu B, Kubala L, Kim I H, Jinks S L, Eiserich J P and Hammock B D (2006) Enhancement of antinociception by coadministration of nonsteroidal anti-inflammatory drugs and soluble epoxide hydrolase inhibitors. Proc Natl Acad Sci USA 103:13646-13651.

Schmelzer K R, Kubala L, Newman J W, Kim I H, Eiserich J P and Hammock B D (2005) Soluble epoxide hydrolase is a therapeutic target for acute inflammation. Proc Natl Acad Sci USA 102:9772-9777.

Serhan C N, Krishnamoorthy S, Recchiuti A and Chiang N (2011) Novel anti-inflammatory-proresolving mediators and their receptors. Curr Top Med Chem 11:629-647.

Spector A A (2009) Arachidonic acid cytochrome P450 epoxygenase pathway. J Lipid Res 50 Suppl:S52-56.

Van Dyke T E (2011) Proresolving lipid mediators: potential for prevention and treatment of periodontitis. J Clin Periodontol 38 Suppl 11:119-125.

Viswanathan S, Hammock B D, Newman J W, Meerarani P, Toborek M and Hennig B (2003) Involvement of CYP 2C9 in mediating the proinflammatory effects of linoleic acid in vascular endothelial cells. J Am Coll Nutr 22:502-510.

Williams J M, Murphy S, Burke M and Roman R J (2010) 20-hydroxyeicosatetraeonic acid: a new target for the treatment of hypertension. J Cardiovasc Pharmacol 56:336-344.

Yamada H, Nakajima T, Domon H, Honda T and Yamazaki K (2015) Endoplasmic reticulum stress response and bone loss in experimental periodontitis in mice. J Periodontal Res 50:500-508.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of preventing, mitigating, decreasing, inhibiting and/or reversing periodontal disease in a subject in need thereof, comprising administering to the subject an effective amount of an inhibitor of soluble epoxide hydrolase (sEH).

2. The method of claim 1, wherein the inhibitor of sEH comprises an inhibitory nucleic acid that inhibits expression of a gene encoding sEH.

3. The method of claim 2, wherein the inhibitory nucleic acid is selected from the group consisting of short interfering RNA (siRNA), short hairpin RNA (shRNA), small temporal RNA (stRNA), and micro-RNA (miRNA).

4. The method of claim 1, wherein the inhibitor of sEH comprises a primary pharmacophore selected from the group consisting of a urea, a carbamate, and an amide.

5. The method of claim 4, wherein the inhibitor of sEH comprises a cyclohexyl moiety, aromatic moiety, substituted aromatic moiety or alkyl moiety attached to the pharmacophore.

6. The method of claim 4, wherein the inhibitor of sEH comprises a cyclohexyl ether moiety attached to the pharmacophore.

7. The method of claim 4, wherein the inhibitor of sEH comprises a phenyl ether or piperidine moiety attached to the pharmacophore.

8. The method of claim 4, wherein the inhibitor of sEH comprises a polyether secondary pharmacophore.

9. The method of claim 4, wherein the inhibitor of sEH has an IC50 of less than about 100 μM.

10. The method of claim 4, wherein the inhibitor of sEH is selected from the group consisting of:
  a) 3-(4-chlorophenyl)-1-(3,4-dichlorphenyl)urea or 3,4,4'-trichlorocarbanilide (TCC; compound 295);
  b) 12-(3-adamantan-1-yl-ureido) dodecanoic acid (AUDA; compound 700);
  c) 1-adamantanyl-3-{5-[2-(2-ethoxyethoxy)ethoxy]pentyl]}urea (AEPU; compound 950);
  d) 1-(1-acetypiperidin-4-yl)-3-adamantanylurea (APAU; compound 1153);
  e) trans-4-[4-(3-Adamantan-1-yl-ureido)-cyclohexyloxy]-benzoic acid (tAUCB; compound 1471);
  f) cis-4-[4-(3-Adamantan-1-yl-ureido)-cyclohexyloxy]-benzoic acid (cAUCB; compound 1686);
  g) 1-(1-methylsulfonyl-piperidin-4-yl)-3-(4-trifluoromethoxy-phenyl)-urea (TUPS; compound 1709);
  h) trans-4-{4-[3-(4-Trifluoromethoxy-phenyl)-ureido]-cyclohexyloxy}-benzoic acid (tTUCB; compound 1728);
  i) 1-trifluoromethoxyphenyl-3-(1-propionylpiperidin-4-yl) urea (TPPU; compound 1770);
  j) 1-(1-ethylsulfonyl-piperidin-4-yl)-3-(4-trifluoromethoxy-phenyl)-urea (TUPSE; compound 2213);
  k) 1-(1-(cyclopropanecarbonyl)piperidin-4-yl)-3-(4-(trifluoromethoxy)phenyl)urea (CPTU; compound 2214);
  l) Trans-N-methyl-4-[4-(3-Adamantan-1-yl-ureido)-cyclohexyloxy]-benzamide (tMAUCB; compound 2225);
  m) trans-N-methyl-4-[4-((3-trifluoromethyl-4-chlorophenyl)-ureido)-cyclohexyloxy]-benzamide (tMTCUCB; compound 2226);
  n) cis-N-methyl-4-{4-[3-(4-trifluoromethoxy-phenyl)-ureido]-cyclohexyloxy}-benzamide (cMTUCB; compound 2228);
  o) 1-cycloheptyl-3-(3-(1,5-diphenyl-1H-pyrazol-3-yl) propyl)urea (HDP$_3$U; compound 2247);
  p) trans-2-(4-(4-(3-(4-trifluoromethoxy-phenyl)-ureido)-cyclohexyloxy)-benzamido)-acetic acid (compound 2283);
  q) N-(methylsulfonyl)-4-(trans-4-(3-(4-trifluoromethoxy-phenyl)-ureido)-cyclohexyloxy)-benzamide (compound 2728);
  r) 1-(trans-4-(4-(1H-tetrazol-5-yl)-phenoxy)-cyclohexyl)-3-(4-(trifluoromethoxy)-phenyl)-urea (compound 2806);
  s) 4-(trans-4-(3-(2-fluorophenyl)-ureido)-cyclohexyloxy)-benzoic acid (compound 2736);
  t) 4-(4-(3-(4-(trifluoromethoxy)-phenyl)-ureido)-phenoxy)-benzoic acid (compound 2803);
  u) 4-(3-fluoro-4-(3-(4-(trifluoromethoxy)-phenyl)-ureido)-phenoxy)-benzoic acid (compound 2807);
  v) N-hydroxy-4-(trans-4-(3-(4-(trifluoromethoxy)-phenyl)-ureido)-cyclohexyloxy)-benzamide (compound 2761);
  w) (5-methyl-2-oxo-1,3-dioxol-4-yl)methyl 4-((1r,4r)-4-(3-(4-(trifluoromethoxy)-phenyl)-ureido)-cyclohexyloxy)-benzoate (compound 2796);
  x) 1-(4-oxocyclohexyl)-3-(4-(trifluoromethoxy)-phenyl)-urea (compound 2809);
  y) methyl 4-(4-(3-(4-(trifluoromethoxy)-phenyl)-ureido)-cyclohexyl amino)-benzoate (compound 2804);
  z) 1-(4-(pyrimidin-2-yloxy)-cyclohexyl)-3-(4-(trifluoromethoxy)-phenyl)-urea (compound 2810); and
  aa) 4-(trans-4-(3-(4-(difluoromethoxy)-phenyl)-ureido)-cyclohexyloxy)-benzoic acid (compound 2805).

11. The method of claim 1, wherein the subject is a human, a canine or a feline.

12. The method of claim 1, wherein the inhibitor of sEH is administered orally, buccally, transmucosally or topically.

13. The method of claim 1, further comprising co-administering an inhibitor of endoplasmic reticular (ER) stress.

14. The method of claim 13, wherein the inhibitor of ER stress acts as a molecular chaperone that facilitates correct protein folding and/or prevents protein aggregation and/or acts to enhance autophagy.

15. The method of claim 13, wherein the inhibitor of ER stress modifies protein folding, regulates glucose homeostasis and/or reduces lipid overload.

16. The method of claim 13, wherein the inhibitor of endoplasmic reticular stress performs one or more of the following:
a) prevents, reduces and/or inhibits phosphorylation of PERK (Thr980), Ire1α (Ser727), eIF2α (Ser51), p38 and/or JNK1/2;
b) prevents, reduces and/or inhibits cleavage of ATF6 and/or XBP1; and/or
c) prevents, reduces and/or inhibits mRNA expression of BiP, ATF4 and/or XBP1.

17. The method of claim 13, wherein the inhibitor of endoplasmic reticular stress is selected from the group consisting of 4-phenyl butyric acid (4-PBA), 3-phenylpropionic acid (3-PPA), 5-phenylvaleric acid (5-PVA), 6-phenylhexanoic acid (6-PHA), butyrate, tauroursodeoxycholic acid, trehalose, deuterated water, docosahexaenoic acid ("DHA"), eicosapentaenoic acid ("EPA"), vitamin C, arabitol, mannose, glycerol, betaine, sarcosine, trimethylamine-N oxide, DMSO and mixtures thereof.

18. The method of claim 13, wherein the inhibitor of endoplasmic reticular stress is selected from the group consisting of 4-phenyl butyric acid (4-PBA), 3-phenylpropionic acid (3-PPA), 5-phenylvaleric acid (5-PVA), 6-phenylhexanoic acid (6-PHA), esters thereof, pharmaceutically acceptable salts thereof, and mixtures thereof.

19. The method of claim 13, wherein one or both of the inhibitor of sEH and the inhibitor of endoplasmic reticular stress are administered at a subtherapeutic dose.

20. The method of claim 1, wherein the inhibitor of sEH is a compound of Formula (II)

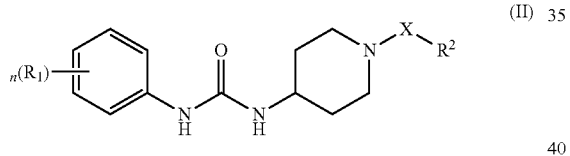

(II)

wherein

X is C(O) or S(O)$_2$;

each $R^1$ is selected from the group consisting of H, halogen, $C_{1-6}$ alkyl, $C_{1-6}$ alkoxy, $C_{1-6}$ haloalkyl, $C_{1-6}$ haloalkoxy, —O-aryl, heterocycloalkyl having 5-6 ring members and at least 1 N heteroatom, —OH, —NO$_2$, and —C(O)OR$^3$, wherein at least 1 $R^1$ is other than H;

$R^2$ is selected from the group consisting of $C_{1-6}$ alkyl optionally substituted with hydroxyl, $C_{1-6}$ haloalkyl, cycloalkyl having 3-6 ring members, and $C_{1-6}$ alkyl-heterocycloalkyl having from 5-6 ring members and at least 2 N heteroatoms as ring members;

$R^3$ is H or $C_{1-6}$ alkyl; and subscript n is an integrer from 1 to 5.

21. The method of claim 20, wherein

X is C(O);

each $R^1$ is selected from the group consisting of H, halogen, $C_{1-6}$ alkyl, $C_{1-6}$ alkoxy, $C_{1-6}$ haloalkyl, $C_{1-6}$ haloalkoxy, wherein at least 1 $R^1$ is other than H;

$R^2$ is $C_{1-6}$ alkyl optionally substituted with hydroxyl or $C_{1-6}$ haloalkyl; and subscript n is an integrer from 1 to 5.

22. The method of claim 20, wherein

X is C(O);

each $R^1$ is selected from the group consisting of H, halogen, $C_{1-6}$ alkyl, $C_{1-6}$ alkoxy, $C_{1-6}$ haloalkyl, $C_{1-6}$ haloalkoxy, wherein at least 1 $R^1$ is other than H;

$R^2$ is $C_{1-6}$ alkyl or $C_{1-6}$ haloalkyl; and subscript n is an integrer from 1 to 5.

23. The method of claim 20, wherein

X is C(O);

each $R^1$ is selected from the group consisting of halogen, and $C_{1-6}$ haloalkoxy;

$R^2$ is $C_{1-6}$ alkyl; and subscript n is an integrer from 1 to 2.

* * * * *

SEQUENCE LISTING

```
<160> NUMBER OF SEQ ID NOS: 38

<210> SEQ ID NO 1
<211> LENGTH: 554
<212> TYPE: PRT
<213> ORGANISM: Homo sapiens

<400> SEQUENCE: 1

Met Thr Leu Arg Gly Ala Val Phe Asp Leu Asp Gly Val Leu Ala Leu
1               5                   10                  15

Pro Ala Val Phe Gly Val Leu Gly Arg Thr Glu Glu Ala Leu Ala Leu
            20                  25                  30

Pro Arg Gly Leu Leu Asn Asp Ala Phe Gln Lys Gly Gly Pro Glu Gly
        35                  40                  45

Ala Thr Thr Arg Leu Met Lys Gly Glu Ile Thr Leu Ser Gln Trp Ile
    50                  55                  60

Pro Leu Met Glu Glu Asn Cys Arg Lys Cys Ser Glu Thr Ala Lys Val
65                  70                  75                  80

Cys Leu Pro Lys Asn Phe Ser Ile Lys Glu Ile Phe Asp Lys Ala Ile
                85                  90                  95

Ser Ala Arg Lys Ile Asn Arg Pro Met Leu Gln Ala Ala Leu Met Leu
            100                 105                 110

Arg Lys Lys Gly Phe Thr Thr Ala Ile Leu Thr Asn Thr Trp Leu Asp
        115                 120                 125

Asp Arg Ala Glu Arg Asp Gly Leu Ala Gln Leu Met Cys Glu Leu Lys
    130                 135                 140

Met His Phe Asp Phe Leu Ile Glu Ser Cys Gln Val Gly Met Val Lys
145                 150                 155                 160

Pro Glu Pro Gln Ile Tyr Lys Phe Leu Leu Asp Thr Leu Lys Ala Ser
                165                 170                 175

Pro Ser Glu Val Val Phe Leu Asp Asp Ile Gly Ala Asn Leu Lys Pro
            180                 185                 190
```

Ala Arg Asp Leu Gly Met Val Thr Ile Leu Val Gln Asp Thr Asp Thr
                195                 200                 205

Ala Leu Lys Glu Leu Glu Lys Val Thr Gly Ile Gln Leu Leu Asn Thr
        210                 215                 220

Pro Ala Pro Leu Pro Thr Ser Cys Asn Pro Ser Asp Met Ser His Gly
225                 230                 235                 240

Tyr Val Thr Val Lys Pro Arg Val Arg Leu His Phe Val Glu Leu Gly
                245                 250                 255

Trp Pro Ala Val Cys Leu Cys His Gly Phe Pro Glu Ser Trp Tyr Ser
            260                 265                 270

Trp Arg Tyr Gln Ile Pro Ala Leu Ala Gln Ala Gly Tyr Arg Val Leu
        275                 280                 285

Ala Met Asp Met Lys Gly Tyr Gly Glu Ser Ser Ala Pro Pro Glu Ile
    290                 295                 300

Glu Glu Tyr Cys Met Glu Val Leu Cys Lys Glu Met Val Thr Phe Leu
305                 310                 315                 320

Asp Lys Leu Gly Leu Ser Gln Ala Val Phe Ile Gly His Asp Trp Gly
                325                 330                 335

Gly Met Leu Val Trp Tyr Met Ala Leu Phe Tyr Pro Glu Arg Val Arg
            340                 345                 350

Ala Val Ala Ser Leu Asn Thr Pro Phe Ile Pro Ala Asn Pro Asn Met
        355                 360                 365

Ser Pro Leu Glu Ser Ile Lys Ala Asn Pro Val Phe Asp Tyr Gln Leu
    370                 375                 380

Tyr Phe Gln Glu Pro Gly Val Ala Glu Ala Glu Leu Glu Gln Asn Leu
385                 390                 395                 400

Ser Arg Thr Phe Lys Ser Leu Phe Arg Ala Ser Asp Glu Ser Val Leu
                405                 410                 415

Ser Met His Lys Val Cys Glu Ala Gly Gly Leu Phe Val Asn Ser Pro
            420                 425                 430

Glu Glu Pro Ser Leu Ser Arg Met Val Thr Glu Glu Ile Gln Phe
        435                 440                 445

Tyr Val Gln Gln Phe Lys Lys Ser Gly Phe Arg Gly Pro Leu Asn Trp
450                 455                 460

Tyr Arg Asn Met Glu Arg Asn Trp Lys Trp Ala Cys Lys Ser Leu Gly
465                 470                 475                 480

Arg Lys Ile Leu Ile Pro Ala Leu Met Val Thr Ala Glu Lys Asp Phe
                485                 490                 495

Val Leu Val Pro Gln Met Ser Gln His Met Glu Asp Trp Ile Pro His
            500                 505                 510

Leu Lys Arg Gly His Ile Glu Asp Cys Gly His Trp Thr Gln Met Asp
        515                 520                 525

Lys Pro Thr Glu Val Asn Gln Ile Leu Ile Lys Trp Leu Asp Ser Asp
    530                 535                 540

Ala Arg Asn Pro Pro Val Val Ser Lys Met
545                 550

<210> SEQ ID NO 2
<211> LENGTH: 2100
<212> TYPE: DNA
<213> ORGANISM: Homo sapiens

<400> SEQUENCE: 2
ggcacgagct ctctctctct ctctctctct ctctcgccgc catgacgctg cgcggcgccg    60

| | |
|---|---|
| tcttcgacct tgacggggtg ctggcgctgc cagcggtgtt cggcgtcctc ggccgcacgg | 120 |
| aggaggccct ggcgctgccc agaggacttc tgaatgatgc tttccagaaa ggggggaccag | 180 |
| agggtgccac tacccggctt atgaaaggag agatcacact ttcccagtgg ataccactca | 240 |
| tggaagaaaa ctgcaggaag tgctccgaga ccgctaaagt ctgcctcccc aagaatttct | 300 |
| ccataaaaga aatctttgac aaggcgattt cagccagaaa gatcaaccgc ccatgctcc | 360 |
| aggcagctct catgctcagg aagaaaggat tcactactgc catcctcacc aacacctggc | 420 |
| tggacgaccg tgctgagaga gatggcctgg cccagctgat gtgtgagctg aagatgcact | 480 |
| ttgacttcct gatagagtcg tgtcaggtgg aatggtcaa acctgaacct cagatctaca | 540 |
| agtttctgct ggacaccctg aaggccagcc ccagtgaggt cgttttttttg gatgacatcg | 600 |
| gggctaatct gaagccagcc cgtgacttgg aatggtcac catcctggtc caggacactg | 660 |
| acacggccct gaaagaactg agaaagtga ccggaatcca gcttctcaat accccggccc | 720 |
| ctctgccgac ctcttgcaat ccaagtgaca tgagccatgg gtacgtgaca gtaaagccca | 780 |
| gggtccgtct gcattttgtg gagctgggct ggcctgctgt gtgcctctgc catggatttc | 840 |
| ccgagagttg gtattcttgg aggtaccaga tccctgctct ggcccaggca ggttaccggg | 900 |
| tcctagctat ggacatgaaa ggctatggag agtcatctgc tcctcccgaa atagaagaat | 960 |
| attgcatgga agtgttatgt aaggagatgg taaccttcct ggataaactg ggcctctctc | 1020 |
| aagcagtgtt cattggccat gactgggggtg gcatgctggt gtggtacatg gctctcttct | 1080 |
| accccgagag agtgagggcg gtggccagtt tgaatactcc cttcatacca gcaaatccca | 1140 |
| acatgtcccc tttggagagt atcaaagcca acccagtatt tgattaccag ctctacttcc | 1200 |
| aagaaccagg agtggctgag gctgaactgg aacagaacct gagtcggact ttcaaaagcc | 1260 |
| tcttcagagc aagcgatgag agtgtttttat ccatgcataa agtctgtgaa gcggggaggac | 1320 |
| tttttgtaaa tagcccagaa gagcccagcc tcagcaggat ggtcactgag gaggaaatcc | 1380 |
| agttctatgt gcagcagttc aagaagtctg gtttcagagg tcctctaaac tggtaccgaa | 1440 |
| acatggaaag gaactggaag tgggcttgca aaagcttggg acggaagatc ctgattccgg | 1500 |
| ccctgatggt cacggcggag aaggacttcg tgctcgttcc tcagatgtcc cagcacatgg | 1560 |
| aggactggat tccccacctg aaaaggggac acattgagga ctgtgggcac tggacacaga | 1620 |
| tggacaagcc aaccgaggtg aatcagatcc tcattaagtg gctggattct gatgcccgga | 1680 |
| acccaccggt ggtctcaaag atgtagaacg cagcgtagtg cccacgctca gcaggtgtgc | 1740 |
| catccttcca cctgctgggg caccattctt agtatacaga ggtggcctta cacacatctt | 1800 |
| gcatggatgg cagcattgtt ctgaaggggt ttgcagaaaa aaaagatttt ctttacataa | 1860 |
| agtgaatcaa attgacatt attttagatc ccagagaaat caggtgtgat tagttctcca | 1920 |
| ggcatgaatg catcgtccct ttatctgtaa gaacccttag tgtcctgtag ggggacagaa | 1980 |
| tggggtggcc aggtggtgat ttctctttga ccaatgcata gtttggcaga aaaatcagcc | 2040 |
| gttcatttag aagaatctta gcagagattg ggatgcctta ctcaataaag ctaagatgac | 2100 |

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cagtgttcat tggccatgac tgg                                               23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
guguucauug gccaugacut t                                                 21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
agucauggcc aaugaacact t                                                 21

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gaaaggctat ggagagtcat ctg                                               23

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
aaggcuaugg agagucauct t                                                 21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
gaugacucuc cauagccuut t                                                 21

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aaaggctatg gagagtcatc tgc                                              23

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
aggcuaugga gucaucut t                                                  21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
agaugacucu ccauagccut t                                                21

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
caagcagtgt tcattggcca tga                                              23

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
agcaguguuc auuggccaut t                                                21

<210> SEQ ID NO 14
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
auggccaaug aacacugcut t                                              21

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cagcacatgg aggactggat tcc                                            23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
gcacauggag gacuggauut t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
aauccagucc uccaugugct t                                              21

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18 ttcaagaga                                                             9

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
```

```
cagtgttcat tggccatgac tgg                                              23
```

<210> SEQ ID NO 20
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

```
gatccccgtg ttcattggcc atgactttca agagaagtca tggccaatga acactttt      59
```

<210> SEQ ID NO 21
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

```
agctaaaaag tgttcattgg ccatgacttc tcttgaaagt catggccaat gaacacggg     59
```

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

```
gaaaggctat ggagagtcat ctg                                              23
```

<210> SEQ ID NO 23
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

```
gatccccaag gctatggaga gtcatcttca agagagatga ctctccatag ccttttttt     59
```

<210> SEQ ID NO 24
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24

```
agctaaaaaa aggctatgga gagtcatctc tcttgaagat gactctccat agccttggg     59
```

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aaaggctatg gagagtcatc tgc                                          23

<210> SEQ ID NO 26
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gatccccagg ctatggagag tcatctttca agagaagatg actctccata gccttttt    59

<210> SEQ ID NO 27
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
agctaaaaaa ggctatggag agtcatcatc tcttgaaaga tgactctcca tagcctggg    59

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
caagcagtgt tcattggcca tga                                          23

<210> SEQ ID NO 29
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gatccccagc agtgttcatt ggccatttca agagaatggc caatgaacac tgcttttt    59

<210> SEQ ID NO 30
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
agctaaaaaa gcagtgttca ttggccattc tcttgaaatg gccaatgaac actgctggg    59

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cagcacatgg aggactggat tcc                                          23

<210> SEQ ID NO 32
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gatccccgca catggaggac tggattttca agagaaatcc agtcctccat gtgctttttt      59

<210> SEQ ID NO 33
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
agctaaaaag cacatggagg actggatttc tcttgaaaat ccagtcctcc atgtgcggg       59

<210> SEQ ID NO 34
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
uguccagugc ccacaguccu                                                  20

<210> SEQ ID NO 35
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
uucccaccug acacgacucu                                                  20

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
guucagccuc agccacuccu                                                  20

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
aguccucccg cuucacaga                                                   19

```
<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
gcccacuucc aguuccuuuc c                                              21
```